US005885797A

United States Patent [19]
Chen et al.

[11] Patent Number: 5,885,797
[45] Date of Patent: Mar. 23, 1999

[54] POLYNUCLEOTIDE SEQUENCES ENCODING PROTEINS INVOLVED IN MYOGENESIS

[75] Inventors: C. M. Amy Chen, Brookline, Mass.; Norbert Kraut; Mark Groudine, both of Seattle, Wash.; Harold Weintraub, deceased, late of Seattle, Wash., by Nancy Weintraub, legal representative

[73] Assignee: Fred Hutchinson Cancer Research Center, Seattle, Wash.

[21] Appl. No.: 704,931

[22] Filed: Aug. 27, 1996

[51] Int. Cl.$^6$ ................................................ C12P 21/06
[52] U.S. Cl. .................. 435/69.1; 435/255.1; 435/320.1; 435/325; 536/23.5
[58] Field of Search .......................... 536/23.5; 435/325, 43569.1, 255.1, 320.1

[56] References Cited

U.S. PATENT DOCUMENTS 5,283,173  2/1994  Fields et al. .

OTHER PUBLICATIONS

Koh et al., Biochem & Biophys Res. Com., vol. 216:34–41, Nov. 2, 1995.
Marino et al., J. Biol. Chem., vol. 266: 6133–6136, May 1991.
Gersten et al., J. Cell. Biochemistry, vol. 16D, p. 170, Mar. 1992.
Fields et al., "A Novel Genetic System to Detect Protein––Protein Interactions," *Nature*, 340:245–246 (Jul. 20, 1989).
Weintraub et al., "Activation of Muscle–Specific Genes in Pigment, Nerve, Fat, Liver, and Fibroblast Cell Lines by Forced Expression of MyoD," *Proc. Natl. Acad. Sci. USA*, 86:5434–5438 (Jul. 1989).
Weintraub et al., "The myoD Gene Family: Nodal Point During Specification of the Muscle Cell Lineage," *Science*, 251:761–766 (1991).
Weintraub et al., "Muscle–Specific Transcriptional Activation by MyoD," *Genes Dev.* 5:1377–1386 (1991).
Kadesch, "Helix–loop–helix Proteins in the Regulation of Immunoglobulin Gene Transcription," *Immunol. Today*, 13:31–36 (1992).
Vojtek et al., "Mammalian Ras Interacts Directly with the Serine/Threonine Kinase Raf," *Cell*, 74:205–214 (1993).
Fields et al., "The Two–Hybrid System: An Assay for Protein–Protein Interaction," *Trends in Genetics*, 10:286–292 (1994).
Johnson et al., "Ectopic Expression of Sonic Hedgehog Alters Dorsal–Ventral Patterning of Somites," *Cell*, 79:1165–1173 (1994).
Hollenberg et al., "Identification of a New Family of Tissue–Specific Basic Helix–Loop–Helix Proteins with a Two––Hybrid System," *Mol. Cell. Biol.*, 15:3813–3822 (1995).
Mundlos et al., "Genetic Mapping of Cleidocranial Dysplasia and Evidence of a Microdeletion in One Family," *Hum. Mol. Gen.* 4:71–75 (1995).

*Primary Examiner*—Christina Chan
*Assistant Examiner*—Patrick Nolan
*Attorney, Agent, or Firm*—Townsend and Townsend and Crew

[57] ABSTRACT

A novel gene, Inhibitor of MyoD Family (I-mf), is provided which encodes novel proteins, I-mfa, I-mfb and I-mfc, involved in regulation of myogenesis during vertebrate development. I-mf is highly expressed in the sclerotome of developing vertebrates and is postulated to play an important role in patterning of the somite and determination sclerotomal cell fate. A unique, C-terminal interactional domain of the I-mf protein mediates physical interactions between I-mfa and members of the MyoD family of transcriptional activators and functions to inhibit transactivation of muscle specific genes by MyoD family members, thereby repressing myogenesis. Further characterization of I-mf activity shows that I-mf associates with MyoD family member proteins and retains them in the cytoplasm by masking their nuclear localization signals. Based on the I-mf genes and proteins disclosed herein, a variety methods and compositions are provided for screening, isolating, and characterizing endogenous and exogenous factors, drugs and therapeutic agents useful to evaluate and/or control myogenesis normal and abnormal development and cell differentiation.

9 Claims, 1 Drawing Sheet

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 1360 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Mus musculus ( v i i ) IMMEDIATE SOURCE:
        ( B ) CLONE: I-mfa ( i x ) FEATURE:
        ( A ) NAME/KEY: CDS
        ( B ) LOCATION: 31..771

( x i ) SEQUENCE DESCRIPTION: SEQ ID NO:1:

```
GAATTCAAGC  GGGCGATCGG  TCCCAGGCCG  ATG  TCC  CAG  GTG  AGC  GGT  CAG  TGC          54
                                    Met  Ser  Gln  Val  Ser  Gly  Gln  Cys
                                     1                  5

CCT  TCT  CGC  TGC  GAC  GCG  CCT  CAT  GGA  GTC  CCC  AGC  GCT  GCC  CTG  GAC    102
Pro  Ser  Arg  Cys  Asp  Ala  Pro  His  Gly  Val  Pro  Ser  Ala  Ala  Leu  Asp
          10                       15                      20

CCA  GCC  CAG  ACC  ATG  TCC  CTC  CTC  CCT  GGG  CTG  GAG  GTA  GCA  AGA  TCC    150
Pro  Ala  Gln  Thr  Met  Ser  Leu  Leu  Pro  Gly  Leu  Glu  Val  Ala  Arg  Ser
 25                      30                      35                      40

ACT  CAC  CCT  GTA  GAG  GCA  TCT  TCT  GAA  GAG  GGC  TTC  CCG  GAG  GAG  GCG    198
Thr  His  Pro  Val  Glu  Ala  Ser  Ser  Glu  Glu  Gly  Phe  Pro  Glu  Glu  Ala
                     45                      50                      55

GCA  CCC  TCC  ATG  CCC  CAT  GAC  AGT  GGT  CTC  CGG  GCT  CAG  CAG  GCT  CTG    246
Ala  Pro  Ser  Met  Pro  His  Asp  Ser  Gly  Leu  Arg  Ala  Gln  Gln  Ala  Leu
               60                      65                      70

AAC  AGC  ATT  GAC  CTC  GAT  GTC  CCC  ACA  GAA  GCT  GTG  ACG  TGC  CAG  CCT    294
Asn  Ser  Ile  Asp  Leu  Asp  Val  Pro  Thr  Glu  Ala  Val  Thr  Cys  Gln  Pro
          75                      80                      85
```

```
CAA  GGG  AAC  CCC  CAA  GGC  TGC  ACC  CCA  CTA  CTG  CCA  AAT  GGC  TCC  AGC        342
Gln  Gly  Asn  Pro  Gln  Gly  Cys  Thr  Pro  Leu  Leu  Pro  Asn  Gly  Ser  Ser
          90                      95                     100

CAC  GAC  CAC  CTC  TCA  GAA  CCG  GGC  AGT  GCA  GGG  CAT  GCG  GGG  AAC  GGT        390
His  Asp  His  Leu  Ser  Glu  Pro  Gly  Ser  Ala  Gly  His  Ala  Gly  Asn  Gly
105                      110                     115                     120

GCT  CTG  GGC  GGG  TCC  AAG  GCC  CAC  CGG  AAG  TTG  CAG  ACG  CAT  CCA  TCT        438
Ala  Leu  Gly  Gly  Ser  Lys  Ala  His  Arg  Lys  Leu  Gln  Thr  His  Pro  Ser
                    125                     130                     135

CTG  GGC  AGC  CAG  GCT  GGA  AGG  AAA  AGC  AGA  GGC  AGC  GCC  CGG  TCA  GCC        486
Leu  Gly  Ser  Gln  Ala  Gly  Arg  Lys  Ser  Arg  Gly  Ser  Ala  Arg  Ser  Ala
               140                     145                     150

TCA  CAG  GTC  CCT  CTC  CAG  GCA  CAG  GAA  GAT  TGC  TGC  GTC  CAC  TGC  ATA        534
Ser  Gln  Val  Pro  Leu  Gln  Ala  Gln  Glu  Asp  Cys  Cys  Val  His  Cys  Ile
          155                     160                     165

CTG  TCC  TGT  CTA  TTC  TGT  GAG  TTC  CTG  ACG  CTC  TGT  AAC  ATC  CTC  CTG        582
Leu  Ser  Cys  Leu  Phe  Cys  Glu  Phe  Leu  Thr  Leu  Cys  Asn  Ile  Leu  Leu
     170                     175                     180

GAC  TGC  GCC  ACC  TGT  GGC  TCC  TGC  AGC  TCT  GAG  GAC  TCC  TGC  CTC  TGC        630
Asp  Cys  Ala  Thr  Cys  Gly  Ser  Cys  Ser  Ser  Glu  Asp  Ser  Cys  Leu  Cys
185                     190                     195                     200

TGC  TGC  TGC  TGT  GGG  TCC  GGC  GAG  TGC  GCG  GAC  TGT  GAC  CTG  CCC  TGC        678
Cys  Cys  Cys  Cys  Gly  Ser  Gly  Glu  Cys  Ala  Asp  Cys  Asp  Leu  Pro  Cys
                    205                     210                     215

GAC  CTG  GAC  TGC  GGC  ATC  GTG  GAT  GCC  TGC  TGC  GAG  TCC  GCA  GAC  TGC        726
Asp  Leu  Asp  Cys  Gly  Ile  Val  Asp  Ala  Cys  Cys  Glu  Ser  Ala  Asp  Cys
               220                     225                     230

TTG  GAG  ATA  TGC  ATG  GAG  TGC  TGT  GGA  CTC  TGT  TTC  TCC  TCC  TGATGCCATG     778
Leu  Glu  Ile  Cys  Met  Glu  Cys  Cys  Gly  Leu  Cys  Phe  Ser  Ser
          235                     240                     245

GGGTGGCCCC  AGAGCTACCG  CACAAAGCTT  GACGCCTCCC  CTGACCCCGG  GCCGCCCCCT                838

CAGAATCCCA  ACCCAGATGT  GAGAAGGTGG  GACGCTCAGA  GGGGCCACCT  CAGCCACCGA                898

ACAGGTCTGC  TTTCAGACGC  GTAGCCTGGT  CCCCTCCACG  GGTGACCAGG  AACACGGCAT                958

CTAGAGCCTG  GTAGGACAGA  ACCAGTTAGC  TGCCATAACT  CAGAACACTG  TGAACGGTAG               1018

GGGAGGGGCC  AGGAGTGGGA  GGGGCCAGGA  ATGGGAGGCC  CGTGTCCTTC  TCTACCTCTG               1078

CTCCAGGTGC  CTGCCTCCCT  CAGCGCTTAC  CCCAGCTTTG  AGGACAGAAA  ATGTGAAAAG               1138

GCCTCTGCCC  CGCCCACTGC  CAGGCCCCCA  CTCTCCTCCC  CAGCTCATTT  CCTGGGCTCT               1198

TGTGGGGGGC  CTAACCCATA  GAGTGACCCA  AGAGGATGGG  GTTTCGGGTG  GGGGTGGGTG               1258

GGAGGGGCGC  AATATGGAAA  AGACTGGAAG  GGGGTAGAGG  GAGGGTCTGT  TCGATTCATT               1318

ACTGTAAATA  AAGACATCCG  TTCAAGCTCC  AAAAAAAAGC  TT                                   1360
```

( 2 ) INFORMATION FOR SEQ ID NO:2:

( i ) SEQUENCE CHARACTERISTICS:
        ( A ) LENGTH: 246 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Gln  Val  Ser  Gly  Gln  Cys  Pro  Ser  Arg  Cys  Asp  Ala  Pro  His
  1                 5                    10                     15

Gly  Val  Pro  Ser  Ala  Ala  Leu  Asp  Pro  Ala  Gln  Thr  Met  Ser  Leu  Leu
               20                     25                     30

Pro  Gly  Leu  Glu  Val  Ala  Arg  Ser  Thr  His  Pro  Val  Glu  Ala  Ser  Ser
```

```
                    3 5                           4 0                           4 5
Glu  Glu  Gly  Phe  Pro  Glu  Glu  Ala  Ala  Pro  Ser  Met  Pro  His  Asp  Ser
          50                            55                       60

Gly  Leu  Arg  Ala  Gln  Gln  Ala  Leu  Asn  Ser  Ile  Asp  Leu  Asp  Val  Pro
65                            70                       75                       80

Thr  Glu  Ala  Val  Thr  Cys  Gln  Pro  Gln  Gly  Asn  Pro  Gln  Gly  Cys  Thr
                         85                            90                  95

Pro  Leu  Leu  Pro  Asn  Gly  Ser  Ser  His  Asp  His  Leu  Ser  Glu  Pro  Gly
               100                      105                      110

Ser  Ala  Gly  His  Ala  Gly  Asn  Gly  Ala  Leu  Gly  Gly  Ser  Lys  Ala  His
          115                      120                      125

Arg  Lys  Leu  Gln  Thr  His  Pro  Ser  Leu  Gly  Ser  Gln  Ala  Gly  Arg  Lys
     130                      135                      140

Ser  Arg  Gly  Ser  Ala  Arg  Ser  Ala  Ser  Gln  Val  Pro  Leu  Gln  Ala  Gln
145                      150                      155                      160

Glu  Asp  Cys  Cys  Val  His  Cys  Ile  Leu  Ser  Cys  Leu  Phe  Cys  Glu  Phe
                    165                      170                      175

Leu  Thr  Leu  Cys  Asn  Ile  Leu  Leu  Asp  Cys  Ala  Thr  Cys  Gly  Ser  Cys
               180                      185                      190

Ser  Ser  Glu  Asp  Ser  Cys  Leu  Cys  Cys  Cys  Cys  Gly  Ser  Gly  Glu
          195                      200                      205

Cys  Ala  Asp  Cys  Asp  Leu  Pro  Cys  Asp  Leu  Asp  Cys  Gly  Ile  Val  Asp
     210                      215                      220

Ala  Cys  Cys  Glu  Ser  Ala  Asp  Cys  Leu  Glu  Ile  Cys  Met  Glu  Cys  Cys
225                      230                      235                      240

Gly  Leu  Cys  Phe  Ser  Ser
                    245
```

( 2 ) INFORMATION FOR SEQ ID NO:3:

( i ) SEQUENCE CHARACTERISTICS:
        ( A ) LENGTH: 1530 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Mus musculus ( v i i ) IMMEDIATE SOURCE:
        ( B ) CLONE: I-mfb ( i x ) FEATURE:
        ( A ) NAME/KEY: CDS
        ( B ) LOCATION: 29..784

( x i ) SEQUENCE DESCRIPTION: SEQ ID NO:3:

```
GAAGGAAGGG  GCGATCGGTC  CCAGGCCG  ATG  TCC  CAG  GTG  AGC  GGT  CAG  TGC         52
                                 Met  Ser  Gln  Val  Ser  Gly  Gln  Cys
                                  1                    5

CCT  TCT  CGC  TGC  GAC  GCG  CCT  CAT  GGA  GTC  CCC  AGC  GCT  GCC  CTG  GAC  100
Pro  Ser  Arg  Cys  Asp  Ala  Pro  His  Gly  Val  Pro  Ser  Ala  Ala  Leu  Asp
          10                       15                       20

CCA  GCC  CAG  ACC  ATG  TCC  CTC  CTC  CCT  GGG  CTG  GAG  GTA  GCA  AGA  TCC  148
Pro  Ala  Gln  Thr  Met  Ser  Leu  Leu  Pro  Gly  Leu  Glu  Val  Ala  Arg  Ser
25                       30                       35                       40

ACT  CAC  CCT  GTA  GAG  GCA  TCT  TCT  GAA  GAG  GGC  TTC  CCG  GAG  GAG  GCG  196
Thr  His  Pro  Val  Glu  Ala  Ser  Ser  Glu  Glu  Gly  Phe  Pro  Glu  Glu  Ala
                    45                       50                       55
```

```
GCA CCC TCC ATG CCC CAT GAC AGT GGT CTC CGG GCT CAG CAG GCT CTG    244
Ala Pro Ser Met Pro His Asp Ser Gly Leu Arg Ala Gln Gln Ala Leu
            60                  65                  70

AAC AGC ATT GAC CTC GAT GTC CCC ACA GAA GCT GTG ACG TGC CAG CCT    292
Asn Ser Ile Asp Leu Asp Val Pro Thr Glu Ala Val Thr Cys Gln Pro
        75                  80                  85

CAA GGG AAC CCC CAA GGC TGC ACC CCA CTA CTG CCA AAT GGC TCC AGC    340
Gln Gly Asn Pro Gln Gly Cys Thr Pro Leu Leu Pro Asn Gly Ser Ser
    90                  95                  100

CAC GAC CAC CTC TCA GAA CCG GGC AGT GCA GGG CAT GCG GGG AAC GGT    388
His Asp His Leu Ser Glu Pro Gly Ser Ala Gly His Ala Gly Asn Gly
105             110                 115                 120

GCT CTG GGC GGG TCC AAG GCC CAC CGG AAG TTG CAG ACG CAT CCA TCT    436
Ala Leu Gly Gly Ser Lys Ala His Arg Lys Leu Gln Thr His Pro Ser
                125                 130                 135

CTG GGC AGC CAG GCT GGA AGG AAA AGC AGA GGC AGC GCC CGG TCA GCC    484
Leu Gly Ser Gln Ala Gly Arg Lys Ser Arg Gly Ser Ala Arg Ser Ala
            140                 145                 150

TCA CAG GTC CCT CTC CAG GCA CAG GAA GGT AAG GCC CCT GCT GTC CGC    532
Ser Gln Val Pro Leu Gln Ala Gln Glu Gly Lys Ala Pro Ala Val Arg
        155                 160                 165

ATC CAC AGA CAG ACA GCA TCA CCA ACT TGC TGC TTA AGA AAT GCA CAA    580
Ile His Arg Gln Thr Ala Ser Pro Thr Cys Cys Leu Arg Asn Ala Gln
170             175                 180

CTC AGT GGA ACA GCA CTT AGG AGC TGA GGC TGA GAG TCA AGG CAT    628
Leu Ser Gly Thr Ala Leu Arg Ser Leu Arg Leu Glu Ser Gln Gly His
185             190                 195                 200

CGT GAG CTA AAT AAC AAG ACC CTG TCG CAA AGC AAT AAC AAG AAA CCA    676
Arg Glu Leu Asn Asn Lys Thr Leu Ser Gln Ser Asn Asn Lys Lys Pro
                205                 210                 215

GGT GTG GCG GCG CAC GCA GCT ATA ATC CCA GCA CTC ACG AGG CCC AAG    724
Gly Val Ala Ala His Ala Ala Ile Ile Pro Ala Leu Thr Arg Pro Lys
            220                 225                 230

CAG AAT TGC CAC GAC CCG AGT TTG CTC CCT GGT ACC CAC GGG GTG GGA    772
Gln Asn Cys His Asp Pro Ser Leu Leu Pro Gly Thr His Gly Val Gly
        235                 240                 245

AAA GAG TTC TAACTCCAAT AAGTTGTCCT CTGACCTCCA CATATATGTG    821
Lys Glu Phe
250

GGATGGTGTC TTAGCAGTTC AATAGCTGAA ACAAAAACAC CATGACTAAA AAGCACGTTG    881

GGGAAGAAAA GGTTTATTTG GCTTACACTT CCAGATCACA GCCCATCATC AAAGGAAGTC    941

AGGACAGGAA CCCAAGCAAT GCAGGCTCCT GGAGGCAGGA GCTGACGCAG AGGCCATGGA   1001

GGAGTGCTGC TTGCTGGTCT GCTTCGCATG ACTTGCTCAG CCAGCTTTTT TATAGAACTC   1061

AGGACCACCA GCCCAGGGGT GGCCCCACCC ACAATGGGCG GGACCCTTCC CCATTCTCCA   1121

CTAATTGAGA AAATACCCTA CAACTGGATC TCATGGAGGC ATTTCCCCAA CTGAGGCTCC   1181

TTCCTCTCTG ATGACTCTGG CTTGTGTCAA ATTGACACAC AAACCAGCCA GTACATGTGT   1241

ATAGAAAGGT AGGCCTCCAG CTCCAGTGAA TCATTCAGGG ACCATGGGGA AAAAACCGCT   1301

AGAGGCGAAG CAGAAGCTAA GGTGAAAGGT AACGGAGAAG ACTCAGTGTG AGCCTGGACC   1361

CCTTGGACCT TGCTATCCCA TTCCACTTAG TAAACCATGC AAAGTTCGTC TGGGCTGATC   1421

CAGAGTAAGC TACCTTATTT CCAGAATCAG AAATTTTCCA CAAGGGGGTT GTGGGGTGTG   1481

TGCTTAACAT GTGATGGCTT TCTATCCCCA GAACCAAAAA TAAAAAAAA             1530
```

( 2 ) INFORMATION FOR SEQ ID NO:4:

( i ) SEQUENCE CHARACTERISTICS:

( A ) LENGTH: 251 amino acids
( B ) TYPE: amino acid
( D ) TOPOLOGY: linear ( i i ) MOLECULE TYPE: protein ( x i ) SEQUENCE DESCRIPTION: SEQ ID NO:4:

| Met | Ser | Gln | Val | Ser | Gly | Gln | Cys | Pro | Ser | Arg | Cys | Asp | Ala | Pro | His |
|---|---|---|---|---|---|---|---|---|---|---|---|---|---|---|---|
| 1 | | | | 5 | | | | | 10 | | | | | 15 | |
| Gly | Val | Pro | Ser | Ala | Ala | Leu | Asp | Pro | Ala | Gln | Thr | Met | Ser | Leu | Leu |
| | | | 20 | | | | 25 | | | | | | 30 | | |
| Pro | Gly | Leu | Glu | Val | Ala | Arg | Ser | Thr | His | Pro | Val | Glu | Ala | Ser | Ser |
| | | 35 | | | | | 40 | | | | | 45 | | | |
| Glu | Glu | Gly | Phe | Pro | Glu | Glu | Ala | Ala | Pro | Ser | Met | Pro | His | Asp | Ser |
| | 50 | | | | | 55 | | | | | 60 | | | | |
| Gly | Leu | Arg | Ala | Gln | Gln | Ala | Leu | Asn | Ser | Ile | Asp | Leu | Asp | Val | Pro |
| 65 | | | | | 70 | | | | | 75 | | | | | 80 |
| Thr | Glu | Ala | Val | Thr | Cys | Gln | Pro | Gln | Gly | Asn | Pro | Gln | Gly | Cys | Thr |
| | | | | 85 | | | | | 90 | | | | | 95 | |
| Pro | Leu | Leu | Pro | Asn | Gly | Ser | Ser | His | Asp | His | Leu | Ser | Glu | Pro | Gly |
| | | | 100 | | | | | 105 | | | | | 110 | | |
| Ser | Ala | Gly | His | Ala | Gly | Asn | Gly | Ala | Leu | Gly | Gly | Ser | Lys | Ala | His |
| | | 115 | | | | | 120 | | | | | 125 | | | |
| Arg | Lys | Leu | Gln | Thr | His | Pro | Ser | Leu | Gly | Ser | Gln | Ala | Gly | Arg | Lys |
| | 130 | | | | | 135 | | | | | 140 | | | | |
| Ser | Arg | Gly | Ser | Ala | Arg | Ser | Ala | Ser | Gln | Val | Pro | Leu | Gln | Ala | Gln |
| 145 | | | | | 150 | | | | | 155 | | | | | 160 |
| Glu | Gly | Lys | Ala | Pro | Ala | Val | Arg | Ile | His | Arg | Gln | Thr | Ala | Ser | Pro |
| | | | | 165 | | | | | 170 | | | | | 175 | |
| Thr | Cys | Cys | Leu | Arg | Asn | Ala | Gln | Leu | Ser | Gly | Thr | Ala | Leu | Arg | Ser |
| | | | 180 | | | | | 185 | | | | | 190 | | |
| Leu | Arg | Leu | Glu | Ser | Gln | Gly | His | Arg | Glu | Leu | Asn | Asn | Lys | Thr | Leu |
| | | 195 | | | | | 200 | | | | | 205 | | | |
| Ser | Gln | Ser | Asn | Asn | Lys | Lys | Pro | Gly | Val | Ala | Ala | His | Ala | Ala | Ile |
| | 210 | | | | | 215 | | | | | 220 | | | | |
| Ile | Pro | Ala | Leu | Thr | Arg | Pro | Lys | Gln | Asn | Cys | His | Asp | Pro | Ser | Leu |
| 225 | | | | | 230 | | | | | 235 | | | | | 240 |
| Leu | Pro | Gly | Thr | His | Gly | Val | Gly | Lys | Glu | Phe |
| | | | | 245 | | | | | 250 | |

( 2 ) INFORMATION FOR SEQ ID NO:5:

( i ) SEQUENCE CHARACTERISTICS:
( A ) LENGTH: 1089 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Mus musculus ( v i i ) IMMEDIATE SOURCE:
( B ) CLONE: I-mfc ( i x ) FEATURE:
( A ) NAME/KEY: CDS
( B ) LOCATION: 211..702

( x i ) SEQUENCE DESCRIPTION: SEQ ID NO:5:

GAATTCAAGC GGAGCCAAGA GCGAGTGAGC GGGGAGGGGG CGCGGGCGAC ACCCAGGTGT 60

```
CGCATGGCGG  GGTCCACGAG  GTGACCTGCC  TAGGCCAGCA  GCGCGCAGCT  TGCACGAGTA        120

TGCGCTAGGG  CACCCACTCC  GTTTCCCCAC  GCACACGCGA  GGGAGGCCTG  CCCCGCCCGC        180

TGAGCGCTGT  TTTCTCCAGG  TCCCAGGCCG  ATG  TCC  CAG  GTG  AGC  GGT  CAG  TGC    234
                                     Met  Ser  Gln  Val  Ser  Gly  Gln  Cys
                                      1              5

CCT  TCT  CGC  TGC  GAC  GCG  CCT  CAT  GGA  GTC  CCC  AGC  GCT  GCC  CTG  GAC   282
Pro  Ser  Arg  Cys  Asp  Ala  Pro  His  Gly  Val  Pro  Ser  Ala  Ala  Leu  Asp
          10                       15                       20

CCA  GCC  CAG  ACC  ATG  TCC  CTC  CTC  CCT  GGG  CTG  GAG  GTA  GCA  AGA  TCC   330
Pro  Ala  Gln  Thr  Met  Ser  Leu  Leu  Pro  Gly  Leu  Glu  Val  Ala  Arg  Ser
 25                      30                       35                       40

ACT  CAC  CCT  GTA  GAG  GCA  TCT  TCT  GAA  GAG  GGC  TTC  CCG  GAG  GAG  GCG   378
Thr  His  Pro  Val  Glu  Ala  Ser  Ser  Glu  Glu  Gly  Phe  Pro  Glu  Glu  Ala
                     45                      50                       55

GCA  CCC  TCC  ATG  CCC  CAT  GAC  AGT  GGT  CTC  CGG  GCT  CAG  CAG  GCT  CTG   426
Ala  Pro  Ser  Met  Pro  His  Asp  Ser  Gly  Leu  Arg  Ala  Gln  Gln  Ala  Leu
               60                       65                       70

AAC  AGC  ATT  GAC  CTC  GAT  GTC  CCC  ACA  GAA  GCT  GTG  ACG  TGC  CAG  CCT   474
Asn  Ser  Ile  Asp  Leu  Asp  Val  Pro  Thr  Glu  Ala  Val  Thr  Cys  Gln  Pro
               75                       80                       85

CAA  GGG  AAC  CCC  CAA  GGC  TGC  ACC  CCA  CTA  CTG  CCA  AAT  GGC  TCC  AGC   522
Gln  Gly  Asn  Pro  Gln  Gly  Cys  Thr  Pro  Leu  Leu  Pro  Asn  Gly  Ser  Ser
      90                       95                      100

CAC  GAC  CAC  CTC  TCA  GAA  CCG  GGC  AGT  GCA  GGG  CAT  GCG  GGG  AAC  GGT   570
His  Asp  His  Leu  Ser  Glu  Pro  Gly  Ser  Ala  Gly  His  Ala  Gly  Asn  Gly
105                      110                      115                      120

GCT  CTG  GGC  GGG  TCC  AAG  GCC  CAC  CGG  AAG  TTG  CAG  ACG  CAT  CCA  CCT   618
Ala  Leu  Gly  Gly  Ser  Lys  Ala  His  Arg  Lys  Leu  Gln  Thr  His  Pro  Pro
                    125                      130                      135

CAG  CCA  CCG  AAC  AGG  TCT  GCT  TTC  AGA  CGC  GTA  GCC  TGG  TCC  CCT  CCA   666
Gln  Pro  Pro  Asn  Arg  Ser  Ala  Phe  Arg  Arg  Val  Ala  Trp  Ser  Pro  Pro
               140                      145                      150

CGG  GTG  ACC  AGG  AAC  ACG  GCA  TCT  AGA  GCC  TGG  TAGGACAGAA  CCAGTTAGCT    719
Arg  Val  Thr  Arg  Asn  Thr  Ala  Ser  Arg  Ala  Trp
               155                      160

GCCATAACTC  AGAACACTGT  GAACGGTAGG  GGAGGGGCCA  GGAGTGGGAG  GGGCCAGGAA        779

TGGGAGGCCC  GTGTCCTTCT  CTACCTCTGC  TCCAGGTGCC  TGCCTCCCTC  AGCGCTTACC        839

CCAGCTTTGA  GGACAGAAAA  TGTGAAAAGG  CCTCTGCCCC  GCCCACTGCC  AGGCCCCCAC        899

TCTCCTCCCC  AGCTCATTTC  CTGGGCTCTT  GTGGGGGGCC  TAACCCATAG  AGTGACCCAA        959

GAGGATGGGG  TTTCGGGTGG  GGTGGGTGG   GAGGGGCGCA  ATATGGAAAA  GACTGGAAGG       1019

GGGTAGAGGG  AGGGTCTGTT  CGATTCATTA  CTGTAAATAA  AGACATCCGT  TCAAGCTCCA       1079

AAAAAAAAA                                                                   1089
```

(2) INFORMATION FOR SEQ ID NO:6:

(i) SEQUENCE CHARACTERISTICS:
        (A) LENGTH: 163 amino acids
        (B) TYPE: amino acid
        (D) TOPOLOGY: linear (ii) MOLECULE TYPE: protein (xi) SEQUENCE DESCRIPTION: SEQ ID NO:6:

```
Met  Ser  Gln  Val  Ser  Gly  Gln  Cys  Pro  Ser  Arg  Cys  Asp  Ala  Pro  His
 1              5                       10                      15

Gly  Val  Pro  Ser  Ala  Ala  Leu  Asp  Pro  Ala  Gln  Thr  Met  Ser  Leu  Leu
               20                       25                      30
```

```
Pro  Gly  Leu  Glu  Val  Ala  Arg  Ser  Thr  His  Pro  Val  Glu  Ala  Ser  Ser
          35                       40                  45

Glu  Glu  Gly  Phe  Pro  Glu  Glu  Ala  Ala  Pro  Ser  Met  Pro  His  Asp  Ser
     50                       55                  60

Gly  Leu  Arg  Ala  Gln  Gln  Ala  Leu  Asn  Ser  Ile  Asp  Leu  Asp  Val  Pro
65                       70                  75                            80

Thr  Glu  Ala  Val  Thr  Cys  Gln  Pro  Gln  Gly  Asn  Pro  Gln  Gly  Cys  Thr
               85                       90                            95

Pro  Leu  Leu  Pro  Asn  Gly  Ser  Ser  His  Asp  His  Leu  Ser  Glu  Pro  Gly
          100                      105                      110

Ser  Ala  Gly  His  Ala  Gly  Asn  Gly  Ala  Leu  Gly  Gly  Ser  Lys  Ala  His
          115                      120                      125

Arg  Lys  Leu  Gln  Thr  His  Pro  Pro  Gln  Pro  Pro  Asn  Arg  Ser  Ala  Phe
     130                      135                      140

Arg  Arg  Val  Ala  Trp  Ser  Pro  Pro  Arg  Val  Thr  Arg  Asn  Thr  Ala  Ser
145                      150                      155                      160

Arg  Ala  Trp
```

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

ACGAATTCCC AGGCCGATGT CCCAG                                                                      25

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GTGCTCGAGC ACCCCATGGC ATCAGGG                                                                    27

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GTCCTCGAGG ACAACTTATT GGAGTTA                                                                    27

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:10:

TAGCTCGAGC TAACTGGTTC TGTCCTA 27

(2) INFORMATION FOR SEQ ID NO:11:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:11:

CTGAATTCCA GGAACTGGGA TATG 24

(2) INFORMATION FOR SEQ ID NO:12:

(i) SEQUENCE CHARACTERISTICS:
  (A) LENGTH: 29 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:12:

GTTGGATCCT CAAAGCACCT GATAAATCG 29

(2) INFORMATION FOR SEQ ID NO:13:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:13:

ACGGATCCCA GGCCGATGTC CCAG 24

(2) INFORMATION FOR SEQ ID NO:14:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:14:

CTCTCGAGTC AGCAGCAGCA GAGGCAGGAG 30

(2) INFORMATION FOR SEQ ID NO:15:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:15:

```
ACGGATCCCC AGACCATGTC CCTCCTC                                                              27
```

( 2 ) INFORMATION FOR SEQ ID NO:16:

( i ) SEQUENCE CHARACTERISTICS:
          ( A ) LENGTH: 27 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:16:

```
GTGCTCGAGC ACCCCATGGC ATCAGGA                                                              27
```

( 2 ) INFORMATION FOR SEQ ID NO:17:

( i ) SEQUENCE CHARACTERISTICS:
          ( A ) LENGTH: 27 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:17:

```
CAGAATTCAC AGCCTCAAGG GAACCCC                                                              27
```

( 2 ) INFORMATION FOR SEQ ID NO:18:

( i ) SEQUENCE CHARACTERISTICS:
          ( A ) LENGTH: 27 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:18:

```
GTGAATTCAG ATTGCTGCGT CCACTGC                                                              27
```

( 2 ) INFORMATION FOR SEQ ID NO:19:

( i ) SEQUENCE CHARACTERISTICS:
          ( A ) LENGTH: 27 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:19:

```
GTGAATTCCT GCTGTGGGTC CGGCGAG                                                              27
```

( 2 ) INFORMATION FOR SEQ ID NO:20:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( i i ) MOLECULE TYPE: cDNA ( v i i ) IMMEDIATE SOURCE:
          ( B ) CLONE: NK2

( x i ) SEQUENCE DESCRIPTION: SEQ ID NO:20:

```
CATCTAGGAA TGAAGTAAGC AGGA                                                                 24
```

( 2 ) INFORMATION FOR SEQ ID NO:21:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: AC48

( x i ) SEQUENCE DESCRIPTION: SEQ ID NO:21:

GCAAGTTGGT GATGCTGTCT GTCTGTGGAT GCG 33

( 2 ) INFORMATION FOR SEQ ID NO:22:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: NK3rev ( x i ) SEQUENCE DESCRIPTION: SEQ ID NO:22:

AATCAATGTG CCTCCTAGAT CTCTAGCC 28

( 2 ) INFORMATION FOR SEQ ID NO:23:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: YZ29

( x i ) SEQUENCE DESCRIPTION: SEQ ID NO:23:

TCGCAGCGCA TCGCCTTCCT A 21

POLYNUCLEOTIDE SEQUENCES ENCODING PROTEINS INVOLVED IN MYOGENESIS

GOVERNMENT SUPPORT

This invention was made with government support under grant numbers GM29176 and R35CA42506 awarded by the National Institutes of Health. The government has certain rights in the invention. Additional support for this invention was provided by a grant from the Human Frontier Science Program.

BACKGROUND OF THE INVENTION

During early development in vertebrates, including humans, determination and differentiation of axial skeletal muscles and vertebral elements is controlled by complex processes of embryonic pattern formation. As part of these pattern forming processes, primordial cells flanking the neural tube and notochord, called the presomitic mesoderm, mature into early segmental structures called the somites. During somite maturation the presomitic mesoderm buds into segments to form the epithelial somites, this process proceeds in a cranio-caudal direction according to an intrinsic developmental timetable (reviewed by Keynes and Stern, *Development* 103: 413–429, 1989; Tam and Traynor, *Anat. Embryol.* 189: 275–305, 1994). After the somites are formed, the ventral-medial parts of the somites delaminate to form the sclerotome, while the dorsal-lateral component of the somite forms the dermomyotome. Prior to this stage of development, the fate of cells in the epithelial somites is plastic, or "undetermined," whereas after this stage the sclerotome cells are "committed" to differentiate into the vertebral column and ribs, and dermomyotome cells are committed to form dermis and axial skeletal muscle.

Accumulating evidence suggests that the patterning of somites into sclerotomal and dermomyotomal compartments depends on inductive signals from other cells, particularly cells forming the notochord and floor plate. A key inductive signal in this regard may be provided by the gene Sonic hedgehog, which has been shown to enhance sclerotomal marker expression and repress dermomyotomal marker expression when the gene is expressed ectopically or in heterologous cells (Johnson et al., *Cell* 79: 1165–1173, 1994; Fan et al., *Cell* 79: 1175–1186, 1994). Another important set of determinants is the MyoD family of myogenic factors which appear to act "downstream" (i.e., subordinately in a developmental regulatory hierarchy) of Sonic hedgehog in determining somite cell fate. The MyoD family of genes includes myoD, myf5, myogenin and MRF4, which each encode muscle specific transcriptional regulatory factors belonging to the basic-helix-loop-helix (bHLH) class of DNA binding proteins (see reviews by Emerson, *Curr. Biol.* 2: 1065–1075, 1990; Weintraub, et al., *Science* 251: 761–766, 1991).

All of the MyoD family of myogenic factors share the remarkable property of being able to convert cells into a myogenic differentiation pathway when the cells are transfected with a MyoD family member gene. For example, primary fibroblasts of different species transfected with the myoD gene are induced to express muscle specific genes, and in many cases form muscle fibers and differentiate into myoblasts or myotubes (see for example, Weintraub et al., *Proc. Natl. Acad. Sci. USA* 86: 5434–5438, 1989). The myogenic activity of the MyoD family genes is explained in part by their conservative, bHLH domains, which includes a basic region required for DNA binding, and an HLH region required for dimerization (see for example, Davis et al., *Cell* 60: 733–746, 1990). Further explanation for the myogenic activity of MyoD family genes includes their ability to heterodimerize with "E proteins" and the ability of these heterodimeric complexes to bind to the "E box" sequence motif, CANNTG, of many muscle specific genes and transactivate their expression (reviewed by Kadesh, *Imm. Today* 13: 31–36, 1992).

The fact that cell commitment toward skeletal muscle differentiation is determined cell-autonomously by myoD, myf5, myogenin and MRF4 raises important questions concerning the "upstream" control of MyoD genes and/or their encoded transcription factors. The ability of MyoD family genes to overcome preexisting cell fates when expressed ectopically indicates that precise regulatory control of the MyoD genes is essential for normal development. This regulation likely includes mechanisms that inhibit expression and/or function of MyoD family genes and/or their products in the sclerotome, because cells in this embryonic compartment are derived from the same precursors as the myotome but do not undergo myogenesis. Such negative regulatory mechanisms controlling MyoD family gene expression, and/or MyoD myogenic factor activity have heretofore remained largely unexplored, and many fundamental questions remain concerning this aspect of myogenic regulation.

Accordingly, there is a general need in the art for further discovery and characterization of myogenic regulatory factors affecting normal and abnormal development in vertebrates. In particular, a general need exists for discovery and characterization of factors involved in regulating the expression and/or activity of MyoD family genes and/or the myogenic factors they encode. In addition to these fundamental needs, there also remain more specific needs in the art to develop effective tools to model, diagnose and treat defects in myogenesis responsible for abnormal development and disease conditions in mammals, including humans.

SUMMARY OF THE INVENTION

It is therefore an object of the present invention to identify and characterize factors involved in myogenesis affecting normal and abnormal vertebrate development and myogenesis.

It is a further object of the invention to develop and characterize effective tools to model, diagnose and treat defects in myogenesis responsible for abnormal development and disease conditions in mammals, including humans.

The invention achieves these objects and other objects and advantages which will become apparent from the description which follows by providing novel polynucleotide sequences, including a novel mammalian gene, Inhibitor of MyoD family (I-mf), and a number of corresponding cDNAs encoding myogenic regulatory proteins, I-mfa, I-mfb and I-mfc. The I-mf-encoding polynucleotides and regulatory proteins provided herein possess novel structural, biochemical and cell biological properties rendering these polynucleotides and proteins useful in the study and/or control of a variety of myogenic regulatory processes. In addition, the I-mf polynucleotides and proteins disclosed herein are useful for generating, isolating, and characterizing additional endogenous regulatory factors, as well as I-mf analogs, drugs and other agents useful for evaluating and/or controlling myogenic processes in normal and abnormal vertebrate development and myogenesis. Reflective of these uses, the invention provides several methods and tools specifically directed to the diagnosis and treatment of disease conditions involving defective myogenic processes in mammals.

Within one aspect of the invention, purified and isolated polynucleotides are provided that encode a native I-mf protein. Examples of these polynucleotides include three, full-length I-mf cDNA clones isolated from murine embryonic cDNA libraries. Other polynucleotides encoding native I-mf proteins are provided that have variations in amino acid sequence compared to the exemplary murine cDNA clones described herein, such as variations due to allelic variations and genetic differences between species. These additional, native I-mf-encoding polynucleotides hybridize under moderate to high stringency conditions to one or more of the aforementioned cDNAs, and encode biologically active products having at least 80% amino acid identity with one or more of the native murine I-mf proteins, I-mfa, I-mfb and I-mfc, or with a corresponding functional domain or peptide fragment of I-mfa, I-mfb and I-mfc.

In related aspects of the invention, purified and isolated I-mf analog-encoding polynucleotides are provided that encode I-mf analogs. These I-mf analogs include genetically engineered, synthetic or otherwise artificially derived polynucleotides that hybridize under moderate to high stringency conditions to one or more of the aforementioned native cDNAs and encode functional I-mf analogs having at least 80% amino acid identity with one or more of the native murine I-mf proteins, I-mfa, I-mfb and I-mfc, or with a corresponding functional domain or peptide fragment of I-mfa, I-mfb and I-mfc. I-mf analogs include mutant I-mf proteins generated by recombinant or synthetic methods, peptide fragments of I-mf, fusion proteins and the like incorporating only a portion of a native I-mf protein, and up to a full length, native I-mf protein. Preferred I-mf analog-encoding polynucleotides in this context encode I-mf analogs possessing normally functional or hyperfunctional biological activity compared to a corresponding native I-mf protein, functional domain or peptide fragment. For example, I-mfa analog-encoding polynucleotides are provided that encode I-mf analogs having functional or hyperfunctional anti-myogenic activity compared to the anti-myogenic activity of corresponding native I-mfa in an in-vitro or in-vivo assay. Particularly preferred I-mf analog-encoding polynucleotides encode I-mf analogs comprising discrete functional domains of a native I-mf protein, for example an I-mfa carboxyl terminal interactional domain ("I-mfa interactional domain"), which is sufficient to mediate interactions with the MyoD family of myogenic factors. Alternative preferred embodiments within this aspect of the invention include mutant polynucleotides that encode hypofunctional analogs of I-mf proteins, or of selected functional domains of I-mf such as the I-mfa interactional domain, which exhibit impaired, null or hypomorphic biological activity compared to native I-mf proteins or I-mf functional domains.

Within additional aspects of the invention, polynucleotide expression constructs are provided for transforming or transfecting a suitable host cell to express an I-mf protein or I-mf analog. These expression constructs include a polynucleotide expression vector operably coupled with a polynucleotide encoding an I-mf protein or I-mf analog to form an expression construct capable of directing the expression of the I-mf protein or I-mf functional analog by the host cell following introduction of the expression construct into the cell. Exemplary I-mf based polynucleotide expression constructs of the invention incorporate a cDNA encoding I-mfa, I-mfb or I-mfc. Additional examples incorporate I-mf analog-encoding polynucleotides which hybridize under moderate to high stringency conditions to one or more of the aforementioned cDNAs encoding native I-mfa, I-mfb or I-mfc. Suitable vectors for use within the polynucleotide expression constructs of the invention include DNA plasmid, DNA viral expression vectors, RNA viral expression vectors and the like. Preferably, the expression vector includes one or more elements that facilitate or control expression of I-mf protein or I-mf functional analog from the construct, such as an inducible promoter or enhancer sequence, a selectable marker sequence, a heterologous reporter sequence, a sequence encoding a retroviral trans-acting factor or the like.

In additional aspects of the invention, methods are provided for expressing an I-mf protein or I-mf analog in a host cell. A suitable host cell is selected, and a polynucleotide expression construct incorporating an I-mf based polynucleotide encoding an I-mf protein or I-mf analog is introduced into the host cell. The expression construct is operable to transform the host cell by directing expression of the I-mf protein or I-mf functional analog in the cell. The cell thus transformed is incubated in a suitable incubation medium under physiological conditions to promote expression of the I-mf protein or I-mf analog by the cell. In related methods, the I-mf protein or I-mf analog is isolated from the host cell or conditioned medium after its expression by the cell. Within other related embodiments, I-mf based expression constructs are employed in methods for modulating (i.e. enhancing or inhibiting) expression or activity of endogenous MyoD family proteins or I-mf proteins in host cells transformed or transfected with the construct. For example, I-mf based expression constructs are used in methods to induce ectopic expression of I-mfa or an I-mfa analog thereby inhibiting a myogenic activity of a MyoD family gene or its expression product. The I-mf based expression construct is introduced into a selected host cell by microinjection, transformation, transfection, electroporation or other suitable method to achieve introduction of the construct into the host cell. The transformed or transfected host cell is cultured, transplanted or left in situ under suitable conditions to permit the host cell to express the I-mf protein or I-off analog. Suitable host cells for use within these methods include a variety of known and readily available fungal, bacterial and mammalian cells routinely selectable to express the I-mf proteins and I-mf analogs of the invention. In yet additional related embodiments of the invention, transformed host cells transformed according the above methods are provided as novel compositions of matter, and as useful tools within yet additional methods of the invention, described herein.

Within another aspect of the invention, substantially pure, native I-mf proteins, including full length I-mfa, I-mfb and I-mfc, and products of interspecific homologs and intraspecific allelic variants of the I-mf gene, are provided. Also provided are I-mf analogs, including mutant I-mf proteins generated by recombinant or synthetic methods, peptide fragments of I-mf, fusion proteins and the like incorporating only a portion of a native I-mf protein and up to a full length, native I-mf protein. Preferred I-mf analogs include functional or hyperfunctional I-mf analogs possessing detectable biological activity of a native I-mf protein. For example, I-mfa analog-encoding polynucleotides are provided that encode I-mf analogs having detectable anti-myogenic activity in an in-vitro or in-vivo assay. These anti-myogenically active I-mf analogs, alone or in the form of a fusion protein, exhibit one or more detectable anti-myogenic activities, which include: binding to a myogenic factor, inhibiting nuclear localization of a myogenic factor, inhibiting DNA binding of a myogenic factor, inhibiting transcriptional activation of muscle specific genes by a myogenic factor, and inhibiting myogenic differentiation of muscle phenotypes in mammalian cells. Particularly preferred anti-myogenic I-mf analogs comprise discrete functional domains of a native I-mf protein, for example the I-mfa interactional domain. Alternative preferred embodiments within this aspect of the invention include hypofunctional analogs of I-mf proteins, or of selected functional domains of I-mf such as the I-mfa interactional domain, which exhibit impaired, null, or hypomorphic anti-myogenic activity compared to native I-mf proteins or I-mf functional domains. Also provided within this aspect of the invention are mutant analogs of I-mf proteins, or of selected functional domains of an I-mf protein, such as the I-mfa interactional domain, which exhibit modified biological activity compared to native I-mf proteins or I-mf functional domains.

Within related aspects of the invention, immunoreagents such as antibodies, antibody derivatives, chimeric antibodies and antibody conjugates are provided that bind specifically to one or more of the native I-mf proteins, peptides, and I-mf analogs disclosed herein. Exemplary immunoreagents include labeled antibodies, antibody derivatives and chimeric antibodies that bind specifically to one or more of the native I-mf proteins and I-mf analogs disclosed herein, thereby providing labeled probes to facilitate detection of antibody-I-mf complexes in a sample suspected of containing I-mf. The immunoreagents of the invention can be used within the methods of the invention as effective tools for detecting and/or quantifying the expression, localization and/or activity of I-mf proteins, peptides or I-mf analogs, and can be incorporated in a wide variety of assays and screening methods disclosed herein. In addition, anti-I-mf immunoreagents can themselves be used as agonists or antagonists of I-mf activity, for example by interfering with binding between I-mf and a myogenic factor such as MyoD or myf5 and thereby preventing or reducing anti-myogenic activity of I-mf in the presence of the antibody. Likewise, anti-I-mf antibody conjugates can be used as targeting agents for delivery of compounds of therapeutic interest. Particularly preferred immunoreagents provided and used within the invention include monoclonal antibodies, which provide the advantages of ease of production and lower antibody titers necessary to achieve a detectable or therapeutically effective level of antibody-target complex formation. However, in other aspects of the invention bi-functional antibodies and panels of antibodies are preferred which are designed or selected to have multiple specificities for a plurality of targets, wherein at least one of these targets is an I-mf protein or I-mf analog.

The general methods and compositions disclosed herein for detecting and/or quantifying levels or activity of I-mf, I-mf analogs and other subject proteins and peptides of the invention provides the bases for a variety of methods to diagnose and treat aberrant myogenic conditions and processes associated with abnormal development and disease. In addition, these methods and compositions provide powerful tools to screen for agonists and antagonists of specific I-mf activities involved in such processes. A particularly useful set of tools in this context includes the various antibodies provided within the invention for detecting I-mf expression, activity and localization. These antibodies can be used in a wide variety of screening and diagnostic methods, as will be apparent to the ordinarily skilled artisan. In addition, the polynucleotide molecules, proteins, peptides and fusion proteins of the present invention are also useful in diagnostic and therapeutic methods and to screen for compounds capable of modulating the activity or expression of I-mf and related compounds. Within such assays, test compounds may be assessed for their ability to increase or decrease I-mf activity or expression, which assays exploit the binding of I-mf to different binding partners, such as MyoD family transcription factors.

In yet additional aspects of the invention, animals, such as mice, and cell lines may be constructed that are heterozygous or homozygous for deletions of the I-mf genes. Such "knock-out" animals and cell lines may be useful as disease models and as test systems for therapeutics capable of overcoming the I-mf deletion. In one aspect of the invention, I-mf is deleted in knock-out mice.

Also provided within the present invention are kits and multicontainer units comprising reagents and components for practicing the assay, screening, diagnostic and treatment methods of the invention. These kits may include, for example, probes for detecting and/or quantifying I-mf, I-mf binding partners, I-mf transcripts and the like.

BRIEF DESCRIPTION OF THE DRAWING

The FIGURE schematically depicts the genomic organization of the I-mf gene. The overlapping genomic clones 11 and 12 are depicted by shaded lines. A partial restriction map of the 31.9 kb genomic region covered by the clone is shown (RI refers to the restriction endonuclease Eco RI, H3 refers to the restriction endonuclease Hind III). Exons are depicted as striped (Exon I) or black (Exons 2–5) boxes.

DETAILED DESCRIPTION OF THE INVENTION

Figure 1:
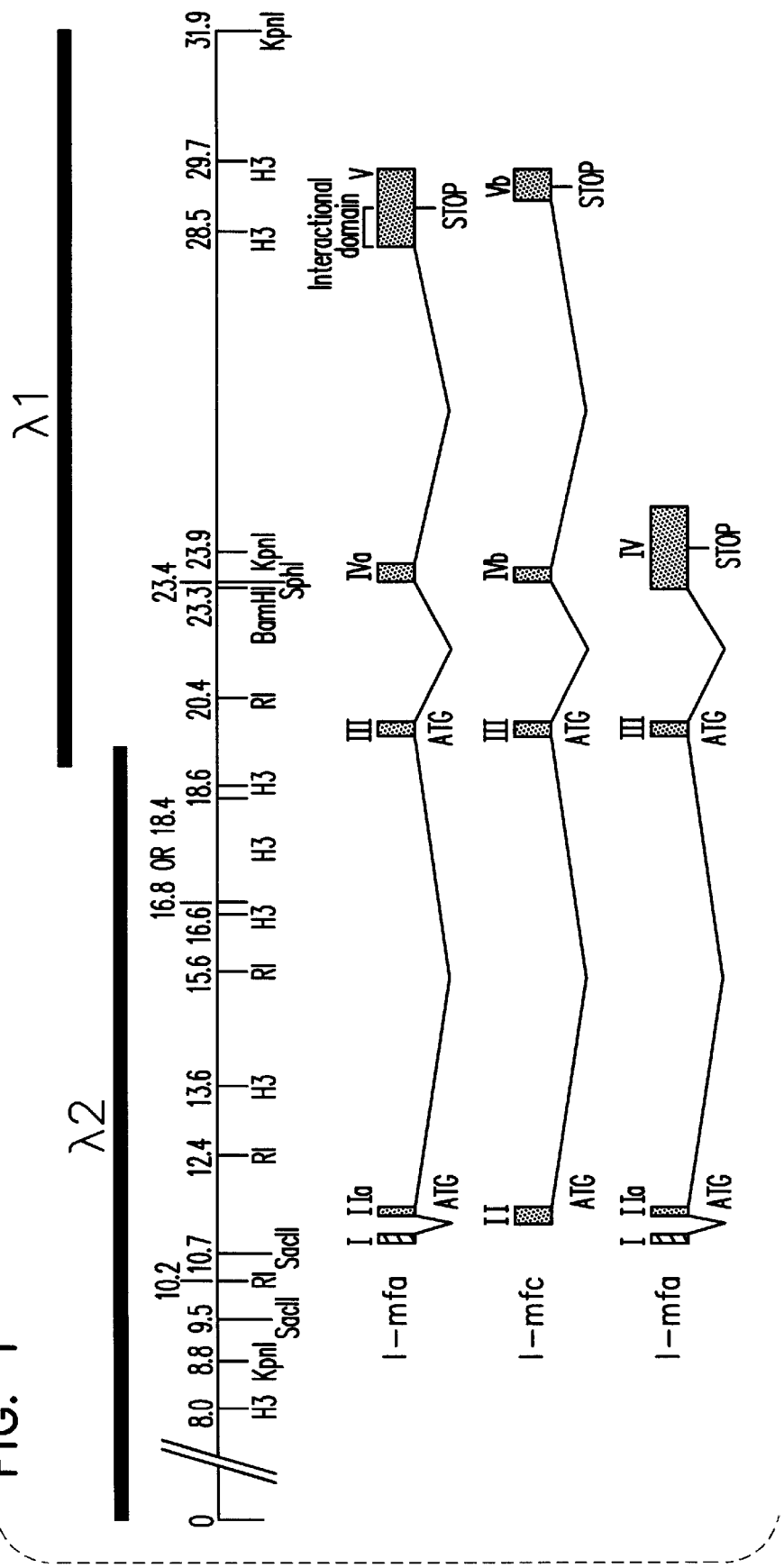

The invention provides a novel vertebrate gene, Inhibitor of MyoD family (I-mf), and a number of corresponding polynucleotides encoding native myogenic regulatory proteins, including I-mfa, I-mfb and I-mfc. These I-mf-encoding polynucleotides and their protein products exhibit novel structural, biochemical and cell biological properties rendering them particularly useful in the study and/or control of a variety of myogenic regulatory processes. In addition, they are useful in assays and screens for generating, isolating, and characterizing functional I-mf analogs, drugs and other agents useful for evaluating and/or controlling myogenic processes in normal and abnormal vertebrate development and disease conditions, as well as for identifying, isolating and characterizing as yet unknown endogenous regulatory factors involved in myogenesis.

Within one aspect of the invention, purified and isolated polynucleotides are provided that encode a native I-mf protein. Examples of these polynucleotides include three, full-length I-mf cDNA clones designated I-mfa, I-mfb and I-mfc. Other polynucleotides encoding native, vertebrate I-mf proteins are also provided that have variations in amino acid sequence compared to the exemplary cDNA clones described herein, such as variations among interspecific homologs and intraspecific allelic variants of the I-mf gene.

As used herein, "native I-mf-encoding polynucleotide" refers to a polynucleotide derived from a natural source, such as a genomic or cDNA library, that hybridizes under moderate to high stringency conditions to one or more of the aforementioned full length murine cDNAs (SEQ ID NOS:1, 3 and 5). As further defined herein, "native I-mf-encoding polynucleotides" encode products having at least 80% amino acid identity with one or more native murine I-mf proteins encoded by (SEQ ID NOS:1, 3 and 5), namely I-mfa, I-mfb and I-mfc (SEQ ID NOS:2, 4 and 6, respectively), or with a corresponding functional domain or peptide fragment of I-mfa, I-mfb and I-mfc, and exhibit one or more biological activities characteristic of one of these native I-mf proteins.

Alignment of amino acid sequences and calculation of percent identity between the aligned sequences is routine in the art. Such routine alignments include the introduction of gaps and employ other widely known conventions to account for sequence additions, deletions conservative substitutions, etc. Briefly, conventional sequence comparison methods involve alignment of the compared sequences to yield the highest possible alignment score, which is readily calculated based on the number of amino acid or nucleotide matches. Once optimal alignment is achieved, the degree of homology between the two sequences is determined by the formula:

$$\frac{\text{Total number of identical matches}}{[\text{length of the longer sequence plus the number of gaps introduced into the longer sequence in order to align the two sequences}]} \times 100$$

Determination of moderate to high stringency hybridization conditions in the context of identifying I-mf proteins will be evident to one skilled in the art and is generally well established in the literature (see, for example: Sambrook et al., *Molecular Cloning A Laboratory Manual*, Cold Spring Harbor Press, Cold Spring Harbor, N.Y., 1989; Hames and Higgins, eds, *Nucleic Acid Hybridization A Practical Approach*, IRL Press, Washington DC, 1985; Berger and Kimmel, eds, *Methods in Enzymology*, Vol. 52, *Guide to Molecular Cloning Techniques*, Academic Press Inc., New York, N.Y., 1987; and Bothwell, Yancopoulos and Alt, eds, Methods for *Cloning and Analysis of Eukaryotic Genes*, Jones and Bartlett Publishers, Boston, Mass., 1990, each of which are incorporated by reference herein in its entirety). Hybridization stringency can be altered by, for example, adjusting the temperature of hybridization, adjusting the percentage of helix-destabilizing agents such as formamide in the hybridization mix, and adjusting the temperature and salt concentration of the wash solutions. In general, the stringency of hybridization is adjusted during the post-hybridization washes by varying the salt concentration and/or the temperature. Stringency of hybridization may be reduced by reducing the percentage of formamide in the hybridization solution or by decreasing the temperature of the wash solution. As used herein, high stringency conditions involve, for example, high temperature hybridization (e.g., 65°14 68° C. in aqueous solution containing 4–6×SSC, or 42° C. in 50% formamide) combined with a high temperature (e.g., 5°14 25° C. below the $T_m$) wash and a low salt concentration (e.g., 0.1×SSC). Moderate stringency conditions involve, for example, hybridization at a temperature between 50° C. and 55° C. and washes in 0.1×SSC, 0.1% SDS at between 50° C. and 55° C., which should be sufficient to identify polynucleotide molecules encoding I-mf from other species or to isolate isoforms of I-mf. By contrast, low stringency conditions may involve lower hybridization temperatures (e.g., 35°–42° C. in 20–50% formamide) and intermediate temperature (e.g., 40°–60° C.) washes in a higher salt concentration (e.g., 2–6×SSC).

As used herein "biological activity of native I-mf" refers to a function or set of activities performed by a native I-mf protein in vivo or in vitro, including, but not limited to anti-myogenic activities of binding to a myogenic factor (e.g. a MyoD family transcription factor), inhibiting nuclear localization of a myogenic factor, inhibiting DNA binding of a myogenic factor, inhibiting transcriptional activation of muscle specific genes by a myogenic factor, and inhibiting myogenic differentiation of muscle phenotypes (e.g. expression of myosin heavy chain or myotube formation) in vertebrate cells, as well as non-myogenically related activities such as binding to antibodies, etc.

Within a preferred aspect of the invention, I-mf encoding polynucleotides encode three native I-mf proteins which share a common amino-terminal region. These same native I-mf proteins have distinct carboxyl termini. Exemplary proteins include the I-mf proteins shown in SEQ ID NOS:2, 4 and 6. These and other common and unique structural characteristics of the different native I-mf proteins disclosed herein render them particularly useful within the invention for identifying and characterizing allelic variants and interspecific homologs of I-mf, for identifying and characterizing as yet unknown myogenic factors that interact with I-mf, and for guiding successful efforts to generate I-mf analog-encoding polynucleotides to obtain useful I-mf protein analogs for these purposes, as is set forth in more detail below.

In related aspects of the invention, purified and isolated I-mf analog-encoding polynucleotides are provided that encode I-mf analogs. As used herein, "I-mf analog-encoding polynucleotide" refers to a genetically engineered, synthetic or otherwise artificially derived polynucleotide that hybridizes under moderate to high stringency conditions with one or more of the aforementioned native murine cDNAs (SEQ ID NOS:1, 3 and 5) encoding either native murine I-mfa, I-mfb or I-mfc (SEQ ID NOS:2, 4 and 6). As further defined herein, "I-mf analog-encoding polynucleotides" encode I-mf analogs having at least 80% amino acid identity with one or more of the native murine I-mf proteins I-mfa, I-mfb and I-mfc (SEQ ID NOS:2, 4 and 6), or with a corresponding functional domain or peptide fragment thereof, and exhibiting one or more detectable biological activities characteristic of native murine I-mfa, I-mfb or I-mfc, or of a corresponding functional domain or peptide fragment thereof. I-mf analogs include mutant I-mf proteins generated by recombinant or synthetic methods, peptide fragments of I-mf, fusion proteins and the like incorporating only a portion of a native I-mf protein, and up to a full length, native I-mf protein.

Preferred I-mf analog-encoding polynucleotides of the invention encode I-mf analogs possessing normally functional or hyperfunctional biological activity compared to a corresponding native I-mf protein, functional domain or peptide fragment. Alternative preferred embodiments within this aspect of the invention include mutant polynucleotides that encode hypofunctional or null analogs of I-mf proteins, or of selected functional domains of I-mf such as the I-mfa interactional domain. In preferred examples, I-mfa analog-encoding polynucleotides are provided that encode I-mf analogs having null or hypofunctional anti-myogenic activity compared to anti-myogenic activity observed for corresponding native I-mfa in in-vitro and in-vivo assays, which mutants are characterized by deletions of an I-mfa carboxyl terminal interactional domain ("I-mfa interactional domain"), necessary and sufficient to mediate interactions with MyoD family of myogenic factors.

Preferred methods to isolate and purify the polynucleotides of the invention encoding native I-mf and I-mf analogs employ a yeast two-hybrid screen to identify cDNAs encoding proteins capable of interacting with the MyoD family of proteins. Briefly, these screens are conducted generally according to the methods described by Fields and Song (*Nature* 340: 245, 1989; and U.S. Pat. No. 5,283,173, each of which are incorporated by reference herein in their entirety and modified as described herein). In one example, a "bait" construct is designed comprising a polynucleotide expression construct incorporating an expression vector operably coupled with a polynucleotide encoding a LexA-MyoD fusion protein. A murine embryonic cDNA fusion library containing random-primed mouse embryonic cDNA joined in-frame to a sequence encoding the VP16 activation domain is prepared as described by Hollenberg et al. (*Mol. Cell. Biol.* 15: 3813–3822, 1995; which is incorporated by reference herein in its entirety). The two-hybrid screen is further executed as described by Vojtek et al., *Cell* 74: 205–214, 1993; and Hollenberg et al., *Mol. Cell. Biol.* 15: 3813–3822, 1995 (each incorporated by reference herein in its entirety and modified as described herein). The yeast host strain containing multimerized LexA binding sites cloned upstream of two reporter genes, the HIS3 gene and the β-galactosidase gene each integrated into the genome is transformed with the LexA-MyoD bait construct and subsequently transformed with the fusion library. Transformants are selected and further analyzed to eliminate false positive clones and clones encoding members of the Id and E protein families, and the remaining VP16 fusions of 18 clones are identified and characterized further. To obtain the full length I-mf cDNAs a mouse embryonic library was screened using an I-mf cDNA fragment obtained from the two-hybrid screen as a probe. Each full-length cDNA encoding I-mfa, I-mfb or I-mfc was subcloned and sequenced using conventional methods and reagents. DNA sequencing and genomic mapping revealed that the I-mfa, I-mfb and I-mfc transcripts are generated through differential poly-(A) adenylation and alternative splicing.

The genomic organization of I-mf was analyzed from two overlapping genomic clones 11 and 12 covering 31.9 kb genomic sequences. Mapping demonstrated that the I-mf gene contains five exons, and that I-mfa, I-mfb and I-mfc are alternative splicing products of I-mf. conventional techniques including, for example, standard screening, subcloning and polymerase chain reactions according to the methods and using the reagents described in Sambrook et al., ibid.

Additional methods to isolate and purify polynucleotides of the invention encoding native I-mf and I-mf analogs utilize a variety of genomic or cDNA libraries known in the art. The polynucleotide sequences encoding native I-mf and I-mf analogs may be isolated from suitable vertebrate hosts including primate, ovine, caprine, bovine, canine, feline, avian, and the like. The techniques for isolating such polynucleotide sequences using probe-based methods are conventional (e.g., standard hybridization techniques are described, for example by, Sambrook et al. ibid., and Bothwell, Yancopoulos and Alt, ibid. and amplification of sequences using polymerase chain reaction (PCR) amplification is described by, for example, Loh et al. *Science* 243: 217–222, 1989; Frohman et al., *Proc. Natl. Acad. Sci. USA* 85: 8998–9002, 1988; and Erlich (ed.), *PCR Technology: Principles and Applications for DNA Amplification*, Stockton Press, 1989; which are incorporated by reference herein in their entirety). The choice of library and selection of probes for the isolation of such polynucleotide sequences is apparent from the disclosure and analysis of I-mf structure and function herein, and is within the level of ordinary skill in the art.

Within additional aspects of the invention, polynucleotide expression constructs encoding an I-mf protein or I-mf analog are provided. The polynucleotide expression constructs of the invention are introduced into suitable host cells to permit the expression of an I-mf protein or I-mf analog. These expression constructs include a polynucleotide expression vector operably coupled with a polynucleotide encoding an I-mf protein or I-mf analog to form an expression construct operable to direct expression of the I-mf protein or I-mf functional analog by the host cell following introduction of the expression construct into the cell. Exemplary I-mf based polynucleotide expression constructs of the invention incorporate one of the three aforementioned, full-length I-mf cDNA clones encoding native I-mfa, I-mfb or I-mfc. Additional examples incorporate I-mf analog-encoding polynucleotides that hybridize under moderate to high stringency conditions to one or more of the aforementioned cDNAs encoding native I-mfa, I-mfb or I-mfc.

Suitable vectors for use within the polynucleotide expression constructs of the invention include DNA plasmids, DNA viral expression vectors, RNA viral expression vectors and the like. Preferably, the expression vector includes one or more elements that facilitate or control expression of I-mf protein or I-mf functional analog, such as a transcriptional promoter and/or enhancer sequences, a sequence encoding a retroviral transacting factor or the like. It may be preferable to include suitable signal sequences to permit the secretion of the proteins and polypeptides of the invention. Additional vector sequences include heterologous reporter sequences and sequences encoding selectable markers. The selection of suitable promoters, enhancers, terminators and the like will be determined by the selected host cell and will be evident to one skilled in the art. A wide variety of suitable yeast vectors are known (see for example, Struhl et al., *Proc. Natl. Acad. Sci. USA* 76: 1035–1039, 1978; Broach et al., *Gene* 8: 121–133, 1979; and Beggs, *Nature* 275: 104–108, 1978, each of which is incorporated herein by reference in its entirety. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al. ibid.), URA3 (Botstein et al., *Gene* 8: 17, 1979), HIS3 (Struhl et al., ibid.) or POT1 (Kawasaki and Bell, EP 171,142). Other suitable selectable markers include the CAT gene, which confers chloramphenicol resistance on yeast cells.

In yet additional aspects of the invention, methods are provided for expressing an I-mf protein or I-mf analog in a eukaryotic host cell. A suitable host cell is selected, and a polynucleotide expression construct incorporating an I-mf based polynucleotide encoding an I-mf protein or I-mf analog is introduced into the host cell. The host cell transformed or transfected with the expression construct is incubated in a suitable medium under physiological conditions to promote expression of the I-mf protein or I-mf analog by the host cell. In related methods, the I-mf protein or I-mf analog is isolated from the host cell or conditioned medium after its expression by the cell. Within other related embodiments, I-mf based expression constructs are employed in methods for modulating (i.e. enhancing or inhibiting) expression or activity of endogenous MyoD family of myogenic proteins or I-mf proteins in host cells transformed or transfected with the construct, for example to induce ectopic expression of I-mfa or an I-mfa analog and thereby inhibit a myogenic activity of a MyoD family gene or its expression product.

Suitable host cells for use within these methods include a variety of known and readily available fungal, bacterial and mammalian cells routinely selectable to express the I-mf proteins and I-mf analogs of the invention. For expression in yeast, strains of the yeast *Saccharomyces cerevisiae* are preferred. Preferred expression vectors for use in yeast include pEMBLye30/2 (Banroques et al., *Cell* 46: 837–844, 1986, incorporated herein by reference in its entirety).

Preferred promoters for use in yeast include promoters from yeast glycolytic genes (Hitzeman et al., *J. Biol. Chem.* 255: 12073–12080, 1980; Alber and Kawasaki, *J. Mol. Appl. Genet.* 1: 419–434, 1982; Kawasaki, U.S. Pat. No. 4,599,311, each of which is incorporated herein by reference in its entirety) or alcohol dehydrogenase genes (Young et al., in *Genetic Engineering of Microorganisms for Chemicals*, Hollaender et al., (eds.), p. 355, Plenum, New York, 1982 and Ammerer, *Meth. Enzymol.* 101: 192–201, 1983, each of which is incorporated herein by reference in its entirety).

In addition to yeast, I-mf proteins and I-mf analogs of the present invention can also be expressed in filamentous fungi, for example, strains of the fungi Aspergillus (McKnight and Upshall, U.S. Pat. No. 4,935,349, which is incorporated herein by reference). Examples of useful promoters in these cells include those derived from *Aspergillus nidulans* glycolytic genes, such as the ADH3 promoter (McKnight et al., *EMBO J.* 4: 2093–2099, 1985) and the tpiA promoter. An example of a suitable terminator is the ADH3 terminator (McKnight et al., ibid.). The expression constructs utilizing such components are cloned into vectors that are capable of insertion into the chromosomal DNA of Aspergillus.

Techniques for transforming fungi are well known in the literature, and have been described, for instance, by Beggs (ibid.); Hinnen et al. (*Proc. Natl. Acad. Sci. USA* 75: 1929–1933, 1978); Yelton et al., (*Proc. Natl. Acad. Sci. USA* 81: 1740–1747, 1984); and Russell (*Nature* 301: 167–169, 1983), each incorporated herein by reference in its entirety. The genotype of the host cell will generally contain a genetic defect that is complemented by the selectable marker present on the expression vector. Choice of a particular host and selectable marker is well within the level of ordinary skill in the art.

In addition to fungal cells, cultured mammalian cells may be used as host cells within the present invention. Preferred cell lines include NIH3T3 cells, and C3H10T1/2 cells (C3H10T1/2; Accession No. CCL 226 American Type Culture Collection (ATCC), 12301 Parklawn Drive, Rockville, Md.). Also suitable as host cells are rodent cell lines, including p3X63Ag8 (ATCC TIB 9), FO (ATCC CRL 1646), NS-1 (ATCC TIB 18) and 210-RCY-Agl (Galfre et al., *Nature* 277: 131, 1979); COS-1 (ATCC CRL 1650); BHK, p363.Ag.8.653 (ATCC CRL 1580) Rat Hep I (ATCC CRL 1600), Rat Hep II (ATCC CRL 1548), TCMK (ATCC CCL 139), Human lung (ATCC CCL 75.1), Human hepatoma (ATCC HTB-52), 20 Hep G2 (ATCC HB 8065), Mouse liver (ATCC CC 29.1), 293 (ATCC CRL 1573; Graham et al., *J. Gen. Virol.* 36: 59–72, 1977) and DUKX cells (Urlaub and Chasin, *Proc. Natl. Acad. Sci USA* 77: 4216–4220, 1980).

Mammalian expression vectors for use in carrying out the present invention will include a promoter capable of directing the transcription of a cloned gene or cDNA. Preferred expression vectors include pEMSVscribe (Davis et al., *Cell* 51: 987–1000, 1987, incorporated herein by reference in its entirety) and pCS2 (Rupp et al., *Genes Dev.* 8: 1311–1323, 1994; Turner and Weintraub, *Genes Dev.* 8: 1434–1447, 1994, each incorporated herein by reference in its entirety). Preferred promoters include viral promoters and cellular promoters. Preferred viral promoters include the major late promoter from adenovirus 2 (Kaufman and Sharp, *Mol. Cell. Biol.* 2: 1304–13199, 1982, incorporated herein by reference in its entirety), the cytomegalovirus promoter (Boshart et al., *Cell* 41: 521–530, 1985, incorporated herein by reference in its entirety) and the SV40 promoter (Subramani et al., *Mol. Cell. Biol.* 1: 854–864, 1981, incorporated herein by reference in its entirety). Cellular promoters include the mouse metallothionein-1 promoter (Palmiter et al., *Science* 222: 809–814, 1983, incorporated herein by reference in its entirety). Also contained in the expression vectors is a transcription termination signal located downstream of the coding sequence of interest. Suitable transcription termination signals include the early or late polyadenylation signals from SV40 Kaufman and Sharp, *Mol. Cell. Biol.* 2: 1304–1319, 1982, incorporated herein by reference in its entirety), the polyadenylation signal from the Adenovirus 5 e1B region and the human growth hormone gene terminator (DeNoto et al., *Nucleic Acid. Res.* 9: 3719–3730, 1981, incorporated herein by reference in its entirety). Expression vectors for use within the invention may also contain a set of RNA splice sites located downstream from the promoter and upstream from the polynucleotide sequence encoding the peptide or protein of interest. Preferred RNA splice sites may be obtained from adenovirus and/or immunoglobulin genes. The expression vectors may also include a noncoding viral leader sequence, such as the adenovirus 2 tripartite leader, located between the promoter and the RNA splice sites, as well as enhancer sequences, such as the SV40 enhancer and the mouse mu enhancer (Gillies, *Cell* 33: 717–728, 1983, incorporated herein by reference in its entirety).

Mammalian cells can also be transduced with virus such as SV40, CMV and the like. In the case of viral vectors, cloned polynucleotide molecules may be introduced by infection of susceptible cells with viral particles. Retroviral vectors may be preferred for use in expressing I-mf in mammalian cells particularly if I-mf is used for gene therapy (for review, see Miller et al. *Methods in Enzmology* 217: 581–599, 1994, incorporated herein by reference in its entirety). Cloned polynucleotide sequences may be introduced into cultured mammalian cells by a number of methods including calcium phosphate precipitation (Wigler et al., *Cell* 14: 725, 1978; Corsaro and Pearson, *Somatic Cell Genetics* 7: 603, 1981; Graham and Van der Eb, *Virology* 52: 456, 1973; incorporated herein by reference in its entirety); lipofection, microinjection and electroporation (Neumann et al., *EMBO J.* 1: 841–845, 1982; incorporated herein by reference in its entirety).

To identify cells that have integrated the cloned polynucleotide, a selectable marker is generally introduced into the cells along with the polynucleotide of interest. Preferred selectable markers for use in cultured mammalian cells include genes that confer resistance to drugs, such as neomycin, hygromycin, and methotrexate. Selectable markers may also complement auxotrophies in the host cell. Yet other selectable markers provide detectable signals, such as beta-galactosidase to identify cells containing the cloned polynucleotide molecules. Selectable markers may be amplifiable. Such amplifiable selectable markers may be used to amplify the number of sequences integrated into the host genome. Amplifiable selectable markers include the DHFR gene and the DHFRr cDNA (Simonsen and Levinson, *Proc. Natl. Acad. Sci. USA* 80: 2495–2499, 1983, incorporated herein by reference in its entirety). Selectable markers are reviewed by Thilly (*Mammalian Cell Technology*. Butterworth Publishers, Stoneham, Mass., incorporated herein by reference in its entirety) and the choice of selectable markers is well within the level of ordinary skill in the art.

Selectable markers may be introduced into the cell on a separate plasmid at the same time as the polynucleotide of interest, or they may be introduced on the same plasmid. If on the same plasmid, the selectable marker and the polynucleotide of interest may be under the control of different promoters or the same promoter, the latter arrangement producing a dicistronic message. Constructs of this type are known in the art (for example, Levinson and Simonsen, U.S. Pat. No. 4,713,339, incorporated herein by reference in its entirety). It may also be advantageous to add additional DNA, known as "carrier DNA" to the mixture which is introduced into the cells.

Transfected host cells are allowed to grow for a period of time, typically 1–2 days, to begin expressing the polynucleotide sequence(s) of interest. Drug selection is then typically applied to select for growth of cells that are expressing the selectable marker in a stable fashion. For cells that have been transfected with an amplifiable selectable marker, the drug concentration may be increased in a stepwise manner to select for increased copy number of the cloned sequences, thereby increasing expression levels.

Host cells containing polynucleotide expression constructs of the present invention are grown in an appropriate or suitable medium. As used herein, the term "appropriate or suitable medium" means a medium containing nutrients required for the growth of cells. Nutrients required for cell growth may include a carbon source, a nitrogen source, essential amino acids, vitamins, minerals and growth factors. The medium will generally select for cells containing the polynucleotide expression construct by, for example, drug selection or deficiency in an essential nutrient which are complemented by the selectable marker on the polynucleotide expression construct or co-transfected with the construct. Yeast cells, for example, are preferably grown in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). It may also be desirable to provide an osmotic stabilizer in the medium. A preferred osmotic stabilizer is sorbitol supplemented into the medium at a concentration between 0.1M and 1.5M., preferably at 0.5M or 1.0M. Cultured mammalian cells are generally grown in commercially available serum-containing or serum-free media. Selection of a medium appropriate for the particular cell line used is within the level of ordinary skill in the art.

I-mf proteins, I-mf analogs and other subject expression products of the invention may be isolated from host cells grown under conditions that allow the expression and/or secretion of I-mf proteins and I-mf analogs by the host cells. The cell material (either whole cells in the case of a secreted protein or peptide or cell debris in the case of a intracellular protein or peptide) is typically separated from the conditioned medium, and the I-mf proteins, I-mf analogs or other subject expression products are isolated using separation and purification techniques known in the art. Suitable isolation techniques include separation, precipitation and fractionation using a chromatographic methods, including liquid chromatography, gradient centrifugation, gel electrophoresis, gel filtration, ion exchange chromatography and immunoaffinity chromatography, among others. Methods of protein purification are well known in the art (see generally, Scopes, R., *Protein Purification*, Springer-Verlag, N.Y., 1982, which is incorporated herein by reference) and may be applied to the purification of I-mf and other subject proteins and peptides described herein. According to these general methods, I-mf and other subject proteins and peptides are provided isolated from host cells or other biological samples, and substantially free of cellular debris, other proteins and like contaminants. For example, purified I-mfa proteins, I-mf analogs, I-mf functional domains and I-mf peptide fragments are provided in a substantially pure form of at least 50% homogeneity. Preferred compositions contain I-mfa proteins and other subject proteins and peptides purified to at least about 70–80% homogeneity, and more preferably to about 95–99% or more homogeneity.

A particularly preferred purification method is immunoaffinity chromatography using an antibody directed against an I-mf protein or an I-mf analog (e.g. an I-mf fusion protein such as HA-I-mfa, described below). The antibody is preferably immobilized or attached to a solid support, substrate or other medium, for example Protein A agarose. Conditioned medium or a sample from the host cells, such as a cell lysate, is then contacted with the bound antibody under conditions that allow formation of complexes between the antibody and I-mf proteins, I-mf analogs or other subject expression products. The complexes may be washed to remove unbound material, and the I-mf proteins, I-mf analogs or other subject expression products are released or eluted through the use of conditions unfavorable to complex formation. Particularly useful methods of elution include altering pH (wherein the immobilized antibody has a high affinity for the ligand at a first pH and a reduced affinity at a second, higher or lower, pH); changes in concentration of certain chaotropic agents; or through the use of detergents.

Within another related aspect of the invention, substantially pure (i.e. 70–80% or greater homogeneity) native I-mf proteins, including full length I-mfa, I-mfb and I-mfc, are provided. Also provided are substantially pure I-mf analogs, including mutant I-mf proteins generated by recombinant or synthetic methods, functional domains and peptide fragments derived from I-mf, fusion proteins and the like incorporating only a portion of a native I-mf protein and up to a full length, native I-mf protein. Within one aspect of the invention, three native I-mf proteins (SEQ ID NOS:2, 4 and 6) are provided which share a common amino-terminal region but have distinct carboxyl termini. The carboxyl termini of I-mfa and I-mfb (SEQ ID NOS:2 and 4, respectively) are approximately equal in size, and comprise approximately one-third of the full length polypeptide. In contrast, I-mfc (SEQ ID NO: 6) has a shorter unique carboxyl terminus. These common and unique structural characteristics of the different native I-mf proteins disclosed herein render them particularly useful within the invention for identifying and characterizing allelic variants and interspecific homologs of I-mf, for identifying and characterizing as yet unknown myogenic factors that interact with I-mf, and for guiding successful efforts to generate I-mf analog-encoding polynucleotides to obtain useful I-mf protein analogs for these purposes, as is set forth in more detail below.

Within other aspects of the invention, purified and isolated I-mf analogs are provided which are genetically engineered, synthetic or otherwise artificially derived proteins or peptides having at least 80% amino acid identity with one or more of the native murine I-mf proteins I-mfa, I-mfb and I-mfc (SEQ ID NOS:2, 4 and 6, respectively), or with a corresponding functional domain or peptide fragment thereof. Generally, determination of sequence identity values between I-mf analogs and their native I-mf counterparts will follow the conservative alignment and computational principles set forth above. For example, I-mf analogs having internal deletions are aligned with a native I-mf counterpart with gaps introduced into the longer sequence and counted in a denominator of the computational algorithm to effectively reduce the derived value of percent sequence identity for the analog. Likewise, when comparing alleles, isoforms, insertion mutants, and substitution mutants, any non-overlapping terminal sequences or introduced sequences are counted in the longer sequence and are included in the conservative computation to effectively reduce resultant sequence identity values. However, where an I-mf analog represents a fragment, fusion portion or other partial sequence derived or engineered to only include a fraction of a corresponding native I-mf (e.g. a highly truncated peptide analog of a parent peptide, or a fusion protein analog incorporating the I-mfa C-terminal interactional domain fused with a heterologous sequence) only those portions of the analog that "correspond" to the native I-mf on a gross structural level are included in determining the length of sequences for computational purposes. Accordingly, terminal portions of a truncated native I-mf "source" protein truncated in a peptide fragment, extensive internally deleted sequences, and heterologous sequences added in a fusion protein, for example, are not considered to correspond for the purpose of computing sequence identity of certain I-mf analogs.

In addition to having the specified minimum level of sequence similarity, the I-mf analogs of the invention exhibit one or more detectable biological activities characteristic of native I-mfa, I-mfb or I-mfc, or of a corresponding functional domain or peptide fragment thereof. For example, anti-myogenically active I-mf analogs, alone or joined with a heterologous sequence or agent in a fusion protein or protein-chemical conjugate, exhibit one or more detectable anti-myogenic biological activities of a native I-mf counterpart (e.g., binding to a myogenic factor, inhibiting nuclear localization of a myogenic factor, inhibiting DNA binding of a myogenic factor, inhibiting transcriptional activation of muscle specific genes by a myogenic factor, and/or inhibiting myogenic differentiation of muscle phenotypes in mammalian cells).

Preferred I-mf analogs of the invention possess normally functional or hyperfunctional biological activity compared to corresponding native I-mf proteins, functional domains or peptide fragments. Normally functional I-mf analogs exhibit approximately the same level of biological activity (e.g., an anti-myogenic activity, half-life, binding interactions with an anti-I-mf antibody, etc.) compared to a corresponding native I-mf protein, functional domain or peptide fragment, whereas the activity of hyperfunctional I-mf analogs is detectably increased relative to its native counterpart. Alternative preferred embodiments within this aspect of the invention include mutant polynucleotides that encode hypofunctional or null analogs (i.e., analogs having a detectably reduced or wholly abolished biological activity compared to a native I-mf counterpart) of I-mf proteins, or of selected functional domains of I-mf such as the I-mfa interactional domain. In specific examples, I-mfa analogs are provided that exhibit null or hypofunctional anti-myogenic activity compared to anti-myogenic activity observed for corresponding native I-mfa in in-vitro and/or in-vivo assays, which mutants are characterized by deletions of the I-mfa carboxyl terminal interactional domain necessary and sufficient to mediate interactions between I-mf and MyoD family of myogenic factors.

Particularly preferred I-mf analogs comprise discrete functional domains of a native I-mf protein, for example the I-mfa interactional domain. One example of an I-mf analog comprising an I-mfa interactional domain provided within the invention is provided in the form of a cDNA clone isolated from a murine library encoding a partial I-mfa peptide fragment (amino acids 1–183 of SEQ ID NO:2) which interacts specifically with MyoD in a yeast two-hybrid screen. Another example of an I-mf analog comprising an I-mfa interactional domain is a sequence identified by deletion mutant analysis to encode an even smaller I-mfa peptide fragment (amino acids 163–202 of SEQ ID NO:2), which binds with Myf5 and exhibits further detectable biological activity of inhibiting Myf5-mediated transcriptional activation and myodifferentiation. Yet another example of an I-mf analog comprising an I-mf functional domain is a sequence determined by deletion mutant expression analysis to encode an I-mfa peptide fragment corresponding to amino acids 87–163 of SEQ ID NO:2, capable of directing I-mfa self interaction.

Desirably, I-mf analogs of the invention will be as small as possible while still maintaining substantially all of the biological activity of a larger peptide. In this context, the subject peptides have an amino acid sequence encoded by a nucleic acid which hybridizes under high stringency conditions with an oligonucleotide of 15 or more contiguous nucleotides of SEQ ID NOS:1, 3, or 5. Particularly preferred I-mf analogs comprise minimal functional domains of a native I-mf protein, for example the I-mfa interactional domain. Minimal functional domains consist of the smallest amino acid sequence determined by deletion mutagenesis or like methods combined with functional assays, as disclosed herein, to have retain least 50% (preferably at least 55%, more preferably about 90% or greater, and most preferably a hyperfunctional activity level of greater than 100%) of normal biological activity compared to that of a fall-length I-mf counterpart (e.g., as determined by a CAT reporter assay such as described in Example 4 below to determine analog activity levels compared to full length I-mf activity levels in co-transfected cells, preferably including normalization of expression levels through Western blot analyses to control for differences in stability between the analog and full length I-mf counterpart in the assay).

Within the methods of the invention, an I-mf analog corresponding to a minimal functional domain (as determined by the specific deletion mutant analyses described herein in Example 4) is a small I-mfa peptide fragment (amino acids 163–202 of SEQ ID NO:2) which binds with Myf5 and exhibits at least 50% of normal biological activity of full length I-mfa of inhibiting Myf5-mediated transcriptional activation and myodifferentiation. Yet another example of an I-mf analog comprising an I-mf functional domain (as determined by the specific deletion mutant analyses described herein in Example 4) is a hyperfunctional I-mfa peptide fragment corresponding to amino acids 87–163 of SEQ ID NO:2, capable of directing I-mfa self interaction. It will be understood by those skilled in the art that the mutant analysis conducted to determine these minimal functional domains can be readily expanded to further narrow and characterize absolute minimal functional domains within the methods of the invention. Further refinement of the minimal functional domains described herein would require only routine extrapolation from the methods and results described herein and would be expected to yield only insubstantial differences in the nature of the result obtained.

It will be generally appreciated that amino acid deletions or non-conservative substitutions within I-mf polynucleotide sequences encoding the I-mfa carboxyl terminal interactional domain and other I-mf functional domains, including most preferably minimal I-mf functional domains, will likely yield I-mf analogs that possess either hyperfunctional or hypofunctional anti-myogenic activities compared to, for example, those of native I-mfa. Such mutants can be useful by themselves in various applications, or combined with other native or mutant peptide sequences, labels or other agents for more specific purposes. For example, an I-mf analog having a hypermorphic mutation in the carboxyl terminal interactional domain is predicted to exhibit enhanced anti-myogenic activity, such as increased binding to a MyoD transcriptional factor or increased inhibition of myodifferentiation is transformed or transfected into suitable cells to express such an analog. Such hyperfunctional I-mf C-terminal interactional domain mutants will be particularly useful as gene therapeutic agents to induce or enhance I-mf function in cells where I-mf expression or activity is impaired. It will be further understood that the proteins and peptides of the invention which have I-mf activity may be modified from a native I-mf sequence as necessary to provide other additional desired activities which may not have been present in a corresponding native I-mf source protein, e.g., novel or altered binding or inhibitory activities, improved adsorption to a solid phase, etc.). In one such detailed example, hyperfunctional I-mf interactional domain mutants can be operably joined to other peptide sequences, labels or chemical agents to achieve a particular therapeutic value. One such chimeric mutant is contemplated having a hyperfunctional I-mf C-terminal interactional domain mutation as well as a dominant negative mutation in the I-mfa self-interactive domain, which combined mutation will yield a combinatorial effect (either greater or lesser, or qualitatively distinct, activity compared to either single mutation). These and other I-mf analogs will provide useful tools in a variety of applications, for example to screen for agonists that replace or enhance I-mf activity, or as gene therapeutic agents capable of modulating endogenous I-mf expression or activity in cells exhibiting aberrant myogenesis, such as CCD affected cells or rhabdomyosarcoma cells.

The I-mf proteins, I-mf analogs and other subject proteins, fusion proteins and peptides of the invention are provided according to the assay and purification techniques, recombinant DNA methodologies and biosynthetic and peptide chemical techniques disclosed herein, as well as by additional methods described elsewhere and generally known in the art. Conventional chemical synthesis or modification methods, recombinant DNA technology and like methods for mutagenizing, synthesizing or deriving desired proteins and peptides are widely known and routinely practiced in the art. For instance, the proteins and peptides of the invention may be subjected to routine mutational changes, such as insertions, deletions, and substitutions, either conservative or non-conservative, where such changes predictably provide for certain advantages in their use. As used herein, conservative substitutions involve replacement of an amino acid residue with another which is biologically and/or chemically similar, e.g., one hydrophobic residue for another, or one polar residue for another. The substitutions include combinations such as Gly, Ala; Val, Ile, Leu; Asp, Glu; Gln; Ser, Thr; Lys, Arg; and Phe, Tyr. Usually, the sequence of the peptide will not differ by more than about 20% from the native I-mf sequence, except where additional amino acids may be added at either terminus for the purpose of modifying the physical or chemical properties of the peptide for, e.g., ease of linking or coupling, and the like.

Having identified different peptides of the invention, in some instances it may be desirable to join two or more peptides in a composition or admixture. The peptides in the composition can be identical or different, and together they should provide reduced, equivalent, greater or qualitatively different biological activity than either of the parent peptides alone. Because of their relatively small size, the peptides of the invention can also be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984); Tam et al., *J. Am. Chem. Soc.* 105: 6442 (1983); Merrifield, *Science* 232: 341–347 (1986); and Barany and Merrifield, *The Peptides*. Gross and Meienhofer, eds., Academic Press, New York, pp. 1–284 (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

Of particular interest within the methods of the invention are oligonucleotide-directed mutagenic techniques that can be routinely used to generate targeted mutations within specific regions or functional domains of I-mf based polynucleotides to yield I-mf analogs having predictable changes in activity compared to their native I-mf counterparts. Various methods for conducting site directed mutagenesis can be optionally employed with equal success, for example alternative one-primer and two-primer methods generally known in the art, as described generally in Sambrook et al., *Molecular Cloning*, A *Laboratory Manual*, ibid.; Ausubel et al., (ed.) *Current Protocols in Molecular Biology*, John Wiley and Sons, Inc., New York (1987), Zoller and Smith, DNA 3: 479–488, 1984 and U.S. Pat. Nos. 4,237,224, 4,273,875, 4,431,739, 4,363,877 and 4,428,941, each incorporated herein by reference in its entirety. Alternatively, mutagenesis may be accomplished using PCR-mediated mutagenesis using, for example, the polymerase chain reaction-mediated site-directed mutagenesis procedure described by Stappert et al. *Nucleic Acid. Res.* 20: 624, 1992; which is incorporated herein by reference in its entirety).

These methods, combined with the detailed teachings relating to structure-function relationships of I-mf encoding polynucleotides and I-mf proteins and analogs, provide clear and detailed guidance for the ordinarily skilled artisan to routinely create a broad range of targeted mutations in I-mf encoding polynucleotides, and to readily express such mutants and isolate their predicted products with a high expectation of success. For example, the teachings herein detail chemical and physical similarities and differences between I-mfa, I-mfb and I-mfc proteins based on extensive mutational analyses and structure-function assays. In addition, the invention provides powerful assays and reagents for further determining I-mf activity and evaluating the functional role of specific domains and residues of I-mf proteins. The principles for selecting targeted mutations based on such data and employing such tools are generally known and easily implemented, and the teachings of the present disclosure greatly narrow the scope of necessary investigation, and enhances the predictability of success, for conducting targeted mutational exercises within the invention.

To clarify and facilitate the objective of engineering I-mf analogs within the invention, the present disclosure further provides that I-mf analogs useful within the invention possess at least 80% amino acid identity with one or more of the native murine I-mf proteins I-mfa, I-mfb and I-mfc (SEQ ID NOS:2, 4 and 6), or with a corresponding (i.e. optimally sequence matched) functional domain or peptide fragment of I-mfa, I-mfb and/or I-mfc. In addition, the I-mf analogs of the invention are further characterized by exhibiting one or more detectable biological activities characteristic of native murine I-mfa, I-mfb or I-mfc, or of a corresponding functional domain or peptide fragment thereof These aforementioned structural similarities are readily determined using conventional sequence comparison protocol, at least to within a reasonable degree of precision achieved by applying a most conservative conventional analysis for conducting the sequence comparison and determining an 80% value estimate within a 5% margin of statistical error. Likewise, determining the presence and/or level of biological activity of an I-mf analog compared to its native I-mf counterpart is within the level of ordinary skill in the art, particularly considering the routine assay methods and powerful new assay tools provided herein for detecting I-mf, I-mf analogs, I-mf binding partners (e.g. anti-I-mf antibodies, or endogenous I-mf binding partners such as MyoD family transcription factors). Accordingly, the present disclosure provides more than sufficient direction and guidance to enable a skilled practitioner to make and use I-mf analogs having the specified structural characteristics, and to readily determine the modifications to produce such analogs likely to possess a predicted biological activity.

Within related aspects of the invention, the subject proteins, peptides and fusion proteins of the invention are used to identify and prepare immunoreagents including antibodies, antibody derivatives, chimeric antibodies and antibody conjugates that bind specifically to one or more of the native I-mf proteins and I-mf analogs disclosed herein. By "Specific binding" is meant that the immunoreagent binds to an I-mf protein and/or I-mf analog with a detectably greater binding affinity or quantitative level of binding than a standard, non-specific control antibody (e.g., anti-keyhole limpet hemocyanin antibody). Exemplary immunoreagents provided within the invention include labeled antibodies, antibody derivatives and chimeric antibodies that bind specifically to one or more of the native I-mf proteins and I-mf analogs disclosed herein, thereby providing useful probes to facilitate detection of antibody-I-mf complexes in a sample suspected of containing I-mf. The immunoreagents of the invention can be used within the methods of the invention as effective tools for detecting and/or quantifying the expression, localization and/or activity of I-mf proteins and I-mf analogs, and can be incorporated in a wide variety of assays and screening methods disclosed herein. In addition, anti-I-mf immunoreagents can themselves be used as agonists or antagonists of I-mf activity, for example by interfering with binding between I-mf and a myogenic factor such as MyoD, Myf5 or myogenin and thereby preventing or reducing anti-myogenic activity of I-mf in the presence of the antibody. Likewise, anti-I-mf antibody conjugates can be used as targeting agents for delivery of compounds of therapeutic interest. Particularly preferred immunoreagents provided and used within the invention include monoclonal antibodies, which provide the advantages of ease of production and lower antibody titers necessary to achieve a detectable or therapeutically effective level of antibody-target complex formation. However, in other aspects of the invention bi-functional antibodies and panels of antibodies are preferred which are designed or selected to have multiple specificities for a plurality of targets, wherein at least one of these targets is an I-mf protein or I-mf analog.

General methods for the production of non-human antisera or monoclonal antibodies (e.g., murine, lagomorpha, porcine, equine) are well known and may be accomplished by, for example, immunizing an animal with I-mf protein or I-mf based peptides. Within one example, for the production of monoclonal antibodies to I-mf, antibody producing cells are obtained from immunized animals, immortalized and screened, or screened first for the production of an antibody that binds to the I-mf protein or peptides and then immortalized. It may be desirable to transfer the antigen binding regions (i.e., F(ab')2 or hypervariable regions) of non-human antibodies into the framework of a human antibody by recombinant DNA techniques to produce a substantially human molecule. Methods for producing such "humanized" molecules are generally well known and described in, for example, U.S. Pat. No. 4,816,397; which is incorporated by reference herein in its entirety. Alternatively, a human monoclonal antibody or portions thereof may be identified by first screening a human B-cell cDNA library for DNA molecules that encode antibodies that specifically bind to I-mf according to the method generally set forth by Huse et al. (*Science* 246: 1275–1281, 1989, incorporated by reference herein in its entirety). The DNA molecule may then be cloned and amplified to obtain sequences that encode the antibody (or binding domain) of the desired specificity.

Anti-I-mf antibodies are particularly useful within the invention as labeled reagents to detect, image and/or quantify the presence or activity of I-mf, I-mf analog, or agonists or antagonists of I-mf activity in biological samples. In one exemplary assay format I-mf proteins or I-mf analogs are identified and/or quantified by using a labeled antibody probe, preferably monoclonal antibodies, which are contacted with biological samples, such as tissues, cells or extracts of cells, under conditions that permit formation antibody-I-mf complexes in the presence of I-mf or I-mf analog (e.g., as determined prior to or contemporaneously with the assay using a control sample having a known presence or level of I-mf). Following a sufficient incubation period, complex formation between the I-mf directed antibody and I-mf protein or I-mf analog in the biological sample are detected qualitatively or quantitatively, and any formation of complexes thus detected indicates the presence or quantity of I-mf protein or I-mf analog in the sample. In alternate assays, unlabeled primary antibody can be used in combination with labels that are reactive with the primary antibody to detect the I-mf protein of I-mf analog. For example, the primary antibody may be detected indirectly by a labeled secondary antibody selected to bind the primary antibody. A wide variety of labels may be employed, such as chemiluminescers, particles (e.g., gold, ferritin, paramagnetic particles), fluorophores, radionuclides, enzymes, enzyme substrates, enzyme inhibitors, ligands (particularly haptens), and the like to facilitate detection and/or quantitation of I-mf.

Immunoassays suitable for use in the present invention include, but are not limited to, enzyme4inked immunosorbant assays, immunoblots, inhibition or competition reactions, sandwich assays, radioimmunoprecipitation, and the like, as generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, NY, 1988, each incorporated by reference herein.

In addition, anti-I-mf antibodies may be used as targeting agents for the delivery of compounds of therapeutic interest. Such compounds include, but are not limited to, toxins, cytostatic compounds, or proenzymes whose potential function is to activate endogenous proenzymes, to activate proenzymes from exogenous sources, or to activate enzyme cleavage sites on prodrugs. Also contemplated within the invention are bifunctional antibodies having independent antigen binding sites on each immunoglobulin molecule (as disclosed for example in *Thromb. Res. Suppl.* X: 83, 1990, and in *The Second Annual IBC International Conference on Antibody Enpineering*, A. George ed., Dec. 16–18, 1991), as well as panels of antibodies having differing specificities. Bifunctional antibodies and antibody panels of particular use within the invention include antibodies and panels of antibodies that bind to both I-mf, or to multiple functional domains of the I-mf protein.

The subject proteins and peptides of the invention are also useful as reagents to detect, image and/or quantify the presence or activity of I-mf, or of agonists or antagonists of I-mf activity, in addition to their usefulness in the preparation of anti-I-mf and anti-I-mf antibodies. In this context a collection of I-mf proteins substantially purified are provided, including all of the I-mf isoforms disclosed herein. In addition to the immunoassays disclosed herein, the presence, quantity and/or activity of I-mf, I-mf analogs and other subject compounds (e.g. MyoD regulatory factors) of the invention can be determined using a variety of alternative methods and reagents, including for example ligand binding assays using immobilized I-mf proteins or fusion proteins. In one such method, PCR is used to generate polynucleotide fragments encoding amino acids corresponding to a selected or putative I-mf functional domain, for example amino acids 162–202 of I-mfa (SEQ ID NO:2) containing the I-mfa C-terminal interactional domain, or amino acids 87–163 of I-mfa containing a self- interacting functional domain of I-mf The polynucleotide fragments are then cloned into a suitable expression vector, and fusion proteins are prepared as disclosed below. The fusion proteins can be endogenously labeled, for example using a covalent radiolabel or other conventional marker, or alternately labeled using antibodies that bind to the fusion protein. In one ligand binding example disclosed herein, a maltose binding protein (P)-I-mf fusion protein is employed (see Example 3, below) and immobilized on a solid phase substrate. The bound fusion protein was then contacted with a biological sample containing labeled MyoD proteins to detect complex formation between the bound fusion protein and MyoD probe. I-mf mf fusion protein-MyoD complexes were detected using SDS polyacrylamide gel chromatography and autoradiography. These and other exemplary assays employing appropriate controls readily apparent to those skilled in the art demonstrate specific interactions between I-mf and MyoD regulatory factors, and can be directly applied and/or adapted to detect and/or quantify selected biological activities of I-mf (e.g. inhibition of DNA binding, transcriptional activation, nuclear localization and/or myogenic induction by MyoD factors). More specific examples, such as ligand overlay assays using peptides derived from MyoD family members (e.g. according to the methods of Chakraborty et al. *EMBO J.* 14: 1314–1321, 1995, incorporated herein by reference in its entirety) can further refine the accuracy and results of such assays, for example to closely map I-mf interactional domains or interactional domains of I-mf binding partners, including MyoD transcription factors.

Additional assays for detecting and/or quantifying the presence or activity of I-mf, I-mf analogs and other subject proteins and peptides of the invention may include Western transfer, protein blot, colony filter and a variety of other methods. Within preferred methods, I-mf, I-mf analogs or other subject molecules of the invention are immobilized or attached to a substrate or support material, such as polymeric tubes, beads, polysaccharide particulates, polysaccharide-containing materials, polyacrylamide or other water insoluble polymeric materials. Methods for immobilization are well known in the art (Mosbach et al., U.S. Pat. No. No. 4,415,665; Clarke et al., *Meth. Enzymology* 68: 436–442, 1979, incorporated herein by reference in its entirety). A common method of immobilization is CNBr activation. Activated substrates are commercially available from a number of suppliers, including Pharmacia (Piscataway, N.J.), Pierce Chemical Co. (Rockford, Ill.) and Bio-Rad Laboratories (Richmond, Calif.). A preferred substrate is CNBr-activated Sepharose (Pharmacia, Piscataway, N.J.). In a preferred embodiment, a substrate/I-mf complex will be in the form of a column, and a biological sample, such as a cell or tissue extract, is contacted with the column under conditions that allow binding to occur between I-mf and any I-mf binding partners present in the sample. The substrate with immobilized I-mf is first equilibrated with a buffer solution of a composition in which the I-mf has been previously found to bind its ligand. The sample, in the solution used for equilibration, is then applied to the substrate/I-mf complex. Where the substrate/I-mf complex is in the form of a column, it is preferred that the sample be passed over the column two or more times to permit full binding of I-mf binding partner to the substrate/I-mf complex. The substrate/I-mf complex is then washed with the same solution to elute unbound material. In addition, a second wash solution may be used to minize nonspecific binding. The bound material may then be released or eluted through the use of conditions unfavorable to complex formation. Particularly useful methods include changes in pH, wherein the immobilized I-mf has a high affinity for the I-mf binding partner at a first pH and a reduced affinity at a second (higher or lower) pH; changes in concentration of certain chaotropic agents; or application of detergents.

The activity of I-mf and I-mf analogs can be further evaluated and incorporated within the methods of the invention with the aid of protein crystallography. The basic protein expression methods of the invention provide for the production of sufficiently large amounts of pure I-mf protein to allow crystallographic analysis of I-mf bound and unbound to their various binding partners. These studies will further elucidate the complex structure and function of the I-mf proteins and will be of substantial value in the design of small molecule inhibitors of these proteins.

Within additional aspects of the invention, a variety of assay, screening, diagnostic and/or therapeutic methods and compositions are provided that employ one or more of the aforementioned inventive tools. In preferred screening and diagnostic methods of the invention, probes corresponding to I-mf proteins, I-mf analogs, anti-I-mf antibodies and the like are used to detect and or quantify expression and/or activity of I-mf in biological samples. In one such method, adapted for determining the presence or quantity of I-mf protein or I-mf analog in a biological sample (e.g. a mammalian cell lysate), the sample is contacted with an I-mf specific probe (e.g. an antibody that specifically binds to I-mf protein or I-mf analog, or another I-mf binding partner that detectably binds with I-mf, such as a MyoD family myogenic factor) under conditions that permit formation of detectable complexes between the probe and I-mf protein or I-mf analog in a suitable control sample (e.g. a control sample having a known amount of I-mf and contacted with the probe under the same conditions as the biological sample to demonstrate, and/or provide a standard value for quantifying, formation of detectable complexes). By detecting the presence and/or amount of complexes formed between the probe and I-mf protein or I-mf analog in the biological sample (e.g. by detecting a label bound to the probe or to a secondary antibody that binds the probe), it can be determined whether I-mf protein or I-mf analog is present in the biological sample and, if desired, at what level.

In related assay, screening and diagnostic methods, labeled I-mf or I-mf analogs are themselves used as probes to detect and/or quantify binding between the I-mf probe and a known or unknown I-mf binding partner, such as a MyoD family myogenic factor. In a comparable procedure to the above noted assay for detecting I-mf, a biological sample is contacted with an I-mf or I-mf analog probe under conditions that permit formation of detectable complexes between the probe and an I-mf binding partner in a suitable control sample containing the binding partner. The presence and/or amount of complexes formed between the I-mf probe and I-mf binding partner is then determined in the biological sample (e.g. by detecting a label bound directly to the I-mf probe or to a secondary, anti-I-mf antibody that specifically binds the I-mf probe), indicating whether an I-mf binding partner is present in the biological sample and, if desired, at what level. In this manner, unknown I-mf binding partners can also be detected and, if present, purified and isolated to determine its structure and activity.

The basic assay methods set forth above allow detection and quantification of I-mf and I-mf binding partners to assess the expression, location and activity of these factors during normal and abnormal development and myogenic differentiation. As such, these methods can be directly incorporated into methods to screen and diagnose abnormal developmental and disease conditions in mammals involving defective expression or activity of I-mf or one of its binding partners. Briefly, diagnostic samples are provided from a patient at risk for a developmental defect or disease involving aberrant expression or activity of I-mf or an I-mf binding partner, and the sample is assayed as above to detect and/or quantify I-mf or I-mf binding partner in the sample. Increased or decreased expression or activity of I-mf or I-mf binding partner in the biological sample (e.g. relative to a level of expression or activity established as a normal baseline in control patient samples) can then be determined as an indicator of the occurrence or risk of related developmental defects or diseases in the patient being diagnosed.

In additional related aspects of the invention, the foregoing assay methods provide the basis for a variety of methods to screen for modulators of I-mf or I-mf binding partner expression or activity. In preferred modulator screening methods, labeled I-mf proteins or I-mf analogs, anti-I-mf antibodies and the like are used as reagents to screen small molecule and peptide libraries to identify inhibitors of I-mf gene expression or I-mf protein activity. In one aspect, I-mf proteins or I-mf analogs are used as competitive probes (either labeled directly, e.g. covalently, or secondarily, e.g. using a labeled antibody to bind I-mf or a heterologous sequence bound to I-mf in a fusion protein). Alternatively, I-mf binding partners, such as an anti-I-mf antibody or a MyoD family myogenic factor, is used as a probe. In one such method, adapted for detecting modulators of I-mf protein levels in a test sample (e.g. a mammalian cell lysate to which a test substance has been added), the test sample containing a test substance is contacted with an I-mf specific probe (e.g. an antibody that specifically binds to I-mf protein or an I-mf binding partner that detectably binds I-mf such as a MyoD family myogenic factor) under conditions that permit formation of detectable complexes between the probe and I-mf protein in the absence of the test substance (e.g. in a control sample having a known amount of I-mf to which no test substance has been added, which is also contacted with the probe under the same conditions as the test sample to demonstrate, and/or provide, prior to the assay or contemporaneously therewith, a standard value for detecting and/or quantifying formation of complexes). Generally the test substance is added in the form of a purified agent, however it is also contemplated that test substances useful within the invention may include substances present throughout the handling of test sample components, for example host cell factors that are present in a cell lysate used for generating the test sample. Such endogenous factors may be segregated between the test and control samples for example by using different cell types for preparing lysates, where the cell type used for preparing the test sample expresses a putative test substance that is not expressed by the cell type used in preparing the control sample. A particularly useful set of test and control cell types in this context are cells that have and have not been induced to undergo myodifferentiation by transformation with a MyoD factor.

To complete the modulator screening assay, the presence and/or amount of complexes formed between I-mf and the I-mf specific probe is detected in the test sample (e.g. by determining the presence or amount of label bound directly to the probe or to a secondary antibody directed against the probe), indicating whether increased or decreased expression or activity of I-mf (i.e. compared to a level of expression or activity established as a relevant control value) resulted in the test sample due to the presence of the test substance.

More specific screening methods are also disclosed herein, including ligand overlay assays using peptides derived from I-mf binding partners as test substances (for example according to the methods of Chakraborty et al. *EMBO J.* 14: 1314–1321, 1995) in assay mixtures and under suitable conditions that permit binding of I-mf to the same or different binding partner in a control sample. In one example an overlapping library of chemically synthesized peptides is generated covering selected sequences of a known I-mf binding partner, preferably a MyoD family myogenic factor, and members of this library are screened as test substances using labeled I-mf, labeled anti-I-mf antibody or like probes according to the above methods. Such screens allow the identification of highly specific peptide inhibitors of I-mf binding activity, which can in turn provide useful reagents for mapping essential and non-essential portions of I-mf proteins necessary for binding and other biological activities.

In alternative screening methods, oligonucleotide probes corresponding to, or complementary to, portions of the I-mf gene are used to detect and/or quantify I-mf gene expression according to the general methods outlined above. By incorporating oligonucleotide probes into the forgoing assay and screening methods, the invention allows further identification and isolation of endogenous regulatory factors and exogenous substance that can modulate I-mf gene expression (e.g. by detecting and/or quantifying levels of I-mf mRNA transcripts in cells exposed to a test substance. I-mf oligonucleotide probes are also useful within diagnostic methods of the invention, for example to map the chromosomal location of I-mf and genes that may be regulated by I-mf, to detect and characterize I-mf alleles, and to identify and characterize genetic defects in I-mf genes present in cell populations or individuals. Further, in the same manner as the above assays employing I-mf protein or anti-I-mf antibodies are adaptable for use within diagnostic methods, assays employing I-mf oligonucleotide probes can be applied to detect and/or quantify expression of I-mf or related genes in diagnostic samples from patients to determine the presence or risk of myogenic diseases involving aberrant I-mf expression. Other reagents that can be used within this context include PCR primers designed to detect the presence of mutant I-mf or aberrant expression of I-mf in diagnostic samples.

Yet additional screening and diagnostic methods are provided within the invention which utilize host cells transformed or transfected with expression constructs incorporating I-mf-encoding, I-mf analog-encoding or I-mf binding partner encoding polynucleotides to provide an in vivo assay mixture. Alternatively, suitable host cells are microinjected or otherwise exposed intracellularly to I-mf, I-mf analog or I-mf binding partner to provide an in vivo assay mixture. Cells thus transformed, transfected or intracellularly exposed can be used, for example, in screens to detect endogenous factors that interact with I-mf or to identify therapeutic compounds capable of modulating I-mf function.

Preferred examples of in vivo screening methods employ recombinant cell lines, ova, transgenic embryos and animals manipulated to disrupt I-mf gene expression or to express native or mutant forms of I-mf, including dominant-negative and "knock-out" recombinants in which the activity of I-mf protein is down-regulated or eliminated. These subject cell lines and animals find uses in screening for candidate therapeutic agents capable of either blocking or substituting for a function performed by I-mf or correcting a cellular defect caused by I- mf The polynucleotide molecules of the present invention may be joined to reporter genes, such as β-galactosidase or luciferase, and inserted into the genome of a suitable host cell, such as an mouse embryonic stem cell by, for example, homologous recombination (for review, see Capecchi, *Trends in Genetics* 5: 70–76, 1989; which is incorporated by reference). Cells and cell lines expressing the subject molecules may then be obtained and used, for example, for screening for compounds that increase or decrease expression of the reporter gene. In one preferred example, discussed in more detail below, "knock-out" mice are generated by replacing the murine I-mf coding region with the neomycin resistance gene to assess the consequences of eliminating the murine I-mf protein. These "knock out" mice are useful for example as model systems for screening compounds that may developmentally, spatially and/or quantitatively alter the expression of the reporter gene. Such mice may be used to study methods to rescue homozygous mutants and as hosts to test transplant tissue for treating diseases or other conditions characterized by aberrant regulation of myogenic processes.

In addition to compound and genetic library screening methods and compositions, the invention provides a variety of disease diagnostic and therapeutic methods and compositions for evaluating and/or treating diseases and other conditions involving aberrant myogenic regulation. One potential target in this context is the human disease cleidocranial displasia (CCD). CCD occurs both as an autosomal dominant and a recessive mutation and results in the delayed ossification of bones. Patients with CCD have bone deformation and in some cases some level of mental retardation. By applying the genetic mapping tools of the invention, I-mf has been mapped to a murine chromosomal location syntenic with the human chromosomal map site 6p21, at which location mutations have been found to be associated with CCD (Nienhaus et al., *Am. J. Med. Genet.* 46: 630–631, 1993; Feldman et al., *Am. J. Med. Genet.* 56: 938–943, 1995 and Mundlos et al., *Hum. Mol. Genet.* 4: 71–75, 1995). This physical proximity between CCD related mutations and the J-mf map site suggests that aberrant I-mf expression and/or activity may well be a factor in CCD. The various methods and compositions of the invention provide a useful assemblage of tools to study and potentially treat this aberrant condition. Potential tools in this regard include the I-mf-encoding polynucleotides and expression constructs, I-mf transformed cells, I-mf based proteins and antibodies, oligonucleotides, as well as antisense polynucleotides and ribozymes that specifically target I-mf polynucleotides.

Other diseases targeted for diagnosis and treatment using the methods and compositions of the invention include rhabdomyosarcomas and other cancers affecting muscle tissue in mammals. Certain rhabdomyosarcoma cells express MyoD but paradoxically fail to differentiate into a myogenic phenotype; suggesting upon consideration of the present disclosure that I-mf may be overexpressed, or that the I-mf protein may be hyperactive, in these cells. Thus, inhibitors of I-mf disclosed herein which block or impair anti-myogenic activity of I-mf may alleviate or curtail aberrant myogenic regulation in rhabdomyosarcoma cells.

In preferred diagnostic methods of the invention, labeled I-mf proteins, I-mf analogs, and I-mf binding partners including anti-I-mf antibodies are employed to detect expression, localization and/or activity of I-mf in the context of normal and/or abnormal myogenic processes or conditions, or in association with specific molecular factors known to be involved in such processes. In one general diagnostic example, I-mf expression or activity is detected and/or quantified in a normal cell population or tissue from a human source, and these results are compared to I-mf expression or activity detected and/or quantified in a test cell population or tissue from a patient at risk for a myogenic disease (for example, a CCD patient or a patient presenting with rhabdomyosarcoma). Detection and/or quantification of I-mf expression, localization or activity can be accomplished by a variety of methods, such as by in situ hybridization using anti-I-mf antibodies, by Western blotting or immunoprecipitation using anti-I-mf antibodies in contact with cell or tissue lysates, or by affinity purification using anti-I-mf antibodies bound to a solid phase, among other methods. Comparable methods are disclosed herein, or are elsewhere disclosed and known in the art, for using non-antibody agents to detect and/or quantify expression or activity of targeted compounds such as I-mf Suitable non-antibody probes for use within these methods include, for example, oligonucleotide probes that hybridize to I-mf transcripts, labeled binding partners of I-mf, and synthetic or recombinant peptide analogs of I-mf, among other useful probe types disclosed herein. For example, I-mf cDNA and oligonucleotide probes may be useful in Northern, Southern, and dot-blot assays for identifying and quantifying the level of expression of I-mf in normal and diseased cells.

Differences that are detected and/or quantified between I-mf expression or activity between normal and test cell populations or tissues may be diagnostic of particular disease states or other conditions characterized by aberrant myogenesis, and may therefore be predictive of the risk or extent of disease, and the outcome of selected courses of treatment. Preferred diagnostic methods in this context rely on labeled polynucleotide probes to map the chromosomal locations of I-mf and related genes, to determine linkage of these genes relative to other genes, and to identify genetic defects in these genes among cell populations or individuals. Additional polynucleotide probes that are useful within the invention include I-mf probes corresponding to partial or complete nucleotide sequences generated from the cDNAs depicted in SEQ ID. NOS:1, 3 or 5 below, and degenerate oligonucleotides based on the amino acid sequences of SEQ ID NOS:2, 4 and 6.

DNA probes and PCR primers are designed as reagents for diagnostic assays for detecting the presence of I-mf or I-mf mutant sequences. The nature of the specific assay may depend on the type of mutational analysis to be carried out and the type of biological sample to be assayed. High molecular weight DNA may be obtained from suitable sources using commercially available kits. Commercially available kits include, the Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, La Jolla, Calif.), TurboGen Isolation Kit (Invitrogen, San Diego, Calif.), and the like. Use of these kits according to the manufacturer's instructions is generally acceptable for purification of DNA prior to practicing the methods of the present invention. PCR primers find used in the amplification of I-mf sequences from normal and diseased tissue. Such sequences may be analyzed by direct sequence analysis or by a variety of means to distinguish normal from mutant sequence. A comparison of fragment size and or comparison of sequences may be used to diagnose a number of diseases such as cancer. Within one example, I-mf-specific DNA probes are used in restriction fragment length polymorphism (RFLP) assays on DNA samples isolated from normal and diseased tissues to detect rearrangements and/or deletions of the I-mf locus. More subtle mutations may be detected by a variety of methods which include but are not restricted to single strand conformation polymorphism (SSCP) (Orita et al., *Proc. Natl. Acad. Sci. USA* 86: 2766–2770, 1989, incorporated by reference herein); dideoxy fingerprinting (ddf) (Orita et al., *Genomics* 5: 874–879, 1991 and Sarkar et al., *Genomics* 13: 441–443, 1992; incorporated by reference herein); restriction endonuclease fingerprinting (REF) (Liu and Sommer, *BioTechniques* 18: 470–477, 1995; incorporated by reference herein); PCR-based RNase protection assay Murthy et al, *DNA & Cell Biol.* 14: 87–94, 1994; incorporated by reference herein) and denaturing gradient gel electrophoresis (Fodde and Losekoot, *Hum. Mutat.* 3: 83–94, 1994, incorporated by reference herein). These methods rely on PCR amplification of coding regions within the genes of interest and use a variety of methods to distinguish between wild-type and mutant sequences. Within other methods, exhaustive analysis of genes is carried out by sequence analysis using primer sets designed for optimal sequencing (Pignon et al, *Hum. Mutat.* 3: 126–132, 1994, incorporated herein by reference in its entirety). The present invention provides methods by which any or all of these types of analyses may be used. As disclosed herein, the I-mf gene and three corresponding complete cDNAs have been cloned. Using these reagents, oligonucleotide primers may be designed to permit the amplification of sequences in the I-mf gene that may then be analyzed by either direct sequencing or other indirect methods such as SSCP to identify mutations within the I-mf gene. Particularly preferred regions for designing oligonucleotide primers include intron-exon junctions. Five exons have been mapped for I-mf. Intron-exon junctions are identified when the coding sequence is interrupted. Oligonucleotides for these assays are preferably designed from flanking intron sequences.

The diagnostic and screening methods of the invention employing DNA probes and PCR primers find use for individuals suspected of being at risk for developing a I-mf-associated disease such as CCD (e.g., family history of disease) or for patients in which such a screening is used to diagnose or eliminate I-mf-associated disease as a causative agent behind a patient's symptoms. In certain embodiments, methods for screening use a biological samples from a patient (e.g., tissue biopsy or amniotic fluid sample) which is screened for the presence of mutations in I-mf. Within these methods, a patient's I-mf gene is compared to normal I-mf DNA (i.e., wild-type I-mf) using a variety of methods, including RFLP analyses, SSCP, and the like, and mutations in I-mf are detected. An aberrant I-mf DNA size pattern, such as for RFLP analysis or SSCP analysis, aberrant I-mf protein and/or aberrant I-mf protein levels as determined by antibody assays would indicate that the patient has developed or is at risk to develop a I-mf-associated disease.

Prenatal diagnosis can be performed when desired, using a variety of methods to obtain fetal cells. These methods include, but are not limited to amniocentesis, chorionic villous sampling and fetoscopy. Prenatal analysis of the I-mf gene is carried out using SSCP, RFLP, DDF and the like.

In addition to the screening and diagnostic methods disclosed herein, the invention provides a range of therapeutic compositions and methods for preventing and/or treating diseases and other conditions involve aberrant myogenesis, for example CCD and rhabdomyosarcoma. Therapeutic methods of the invention variously utilize I-mf-encoding polynucleotides, I-mf proteins and analogs, I-mf binding antibodies and other binding partners, expression constructs incorporating I-mf-encoding polynucleotides, host cells transformed to express I-mf, and other therapeutic agents identified within the invention as modulators of I-mf expression and/or activity, including triplex forming oligonucleotides, antisense polynucleotides and ribozymes that specifically target I-mf encoding polynucleotides.

In preferred therapeutic methods directed to the treatment of myogenic disease, it is useful to employ agents that inhibit or enhance I-mf expression or activity and which thereby can eliminate or impair aberrant myogenic processes. Useful agents in this context generally include agents that impair or enhance I-mf binding to its partners or otherwise enhance I-mf expression or activity, for example mutant I-mf based expression constructs that induce or enhance I-mf expression or activity in targeted cells. Therapeutic substances which can serve as inhibitors or antagonists of I-mf include, but are not limited to, compounds capable of inhibiting the formation of I-mf-MyoD family member binding complexes, compounds that reduce or inhibit the activity of I-mf, and compounds that interfere with the expression of I-mf protein. Such agents may include chemical compound inhibitors of I-mf, protein, peptide or antibody I-mf antagonists, and molecules that inhibit the expression of I-mf such as triplex forming oligonucleotides, antisense polynucleotides, ribozymes, etc.

The use of antisense polynucleotides and their applications are described generally in, for example, Mol and Van der Krul, eds., *Antisense Nucleic Acids and Proteins Fundamentals and Applications*, New York, N.Y., 1992, incorporated by reference herein in its entirety. Suitable antisense oligonucleotides are at least 15 nucleotides in length and up to and including the upstream untranslated and associated coding sequences of I-mf. As will be evident to one skilled in the art, the optimal length of antisense oligonucleotides is dependent on the strength of the interaction between the antisense oligonucleotides and their complementary sequence on the mRNA, the temperature and ionic environment in which translation takes place, the base sequence of the antisense oligonucleotide, the presence of secondary and tertiary structure in the mRNA and/or in the antisense oligonucleotide and the preferred delivery mode. For example, soluble antisense oligonucleotides have been used to inhibit transcription/translation of a target gene (Ching et al., *Proc. Natl. Acad. Sci. USA* 86:10006–10010, 1989; Broder et al., *Ann. Int. Med.* 113: 604–618 (1990); Loreau et al., *FEBS Letters* 274:53–56 1990; Holcenberg et al., WO91/11535; U.S. Ser. No. 07/530,165 ("New human CRIPTO gene"); WO91/09865; WO91/04753; WO90/13641; and EP 386563, each incorporated herein by reference). Suitable target sequences for antisense polynucleotides include intron-exon junctions (to prevent proper splicing), regions in which DNA/RNA hybrids will prevent transport of mRNA from the nucleus to the cytoplasm, initiation factor binding sites, ribosome binding sites, and sites that interfere with ribosome progression. A particularly preferred target region for antisense polynucleotides is the 5' untranslated region of the gene of interest, for example the I-mf gene.

Antisense polynucleotides targeted to the I-mf gene may also be prepared by inserting a DNA molecule containing the target polynucleotide sequence into a suitable expression vector such that the DNA molecule is inserted downstream of a promoter in a reverse orientation as compared to the gene itself. The expression vector may then be transduced, transformed or transfected into a suitable cell resulting in the expression of antisense polynucleotides. Alternatively, antisense oligonucleotides may be synthesized using standard manual or automated synthesis techniques. Synthesized oligonucleotides may be introduced into suitable cells by a variety of means including electroporation (e.g., as described in Yang et al., *Nucl. Acids. Res.* 23: 2803–2810, 1995), calcium phosphate precipitation, microinjection, poly-L-ornithine/DMSO (Dong et al., *Nucl. Acids. Res.* 21: 771–772, 1993). The selection of a suitable antisense oligonucleotide administration method will be evident to one skilled in the art. With respect to synthesized oligonucleotides, the stability of antisense oligonucleotide-mRNA hybrids may be increased by the addition of stabilizing agents to the oligonucleotide. Stabilizing agents include intercalating agents that are covalently attached to either or both ends of the oligonucleotide. Oligonucleotides may be made resistant to nucleases by, for example, modifications to the phosphodiester backbone by the introduction of phosphotriesters, phosphonates, phosphorothioates, phosphoroselenoates, phosphoramidates or phosphorodithioates. Oligonucleotides may also be made nuclease resistant by the synthesis of the oligonucleotides with alpha-anomers of the deoxyribonucleotides, as generally described in Mol and Van der Krul (ibid.).

Within another embodiment, polynucleotide-based inhibitors of the present invention include the triplex forming oligonucleotides, sequence-specific DNA binding drugs that interfere with target gene transcription. Triplex-forming oligonucleotides are generally described in Maher, *Bioessays* 14: 807–815, 1992; Gee et al., *Gene* 149: 109–114, 1994; Noonberg et al., *Gene* 149: 123–126, 1994; Song et al., *Ann. NY Acad. Sci.* 761: 97–108, 1995; Westin et al., *Nuc. Acids. Res.* 23: 2184–2191, 1995; and Wand and Glazer, *J. Biol. Chem.* 207: 22595–22901, 1995, each incorporated herein by reference in its entirety. These oligonucleotides form triple helical complexes under physiological conditions on double-stranded DNA, selectively inhibiting gene transcription by physically blocking RNA polymerase or transcription factor access to the DNA template. See also, e.g., WO 95/25818; WO 95/20404; WO 94/15616; WO 94/04550; and WO 93/09788, each of which is incorporated herein by reference. The triplex forming oligonucleotides may contain either a nucleotide or non-nucleotide tail to enhance the inhibition of transcription factor binding. Within one example, the triplex forming oligonucleotides are targeted to the I-mf gene.

For polynucleotide-based inhibitors, the choice of a suitable sequence will be guided by, for example, the type of inhibitor (i.e., triplex forming oligonucleotide or antisense polynucleotide) and the species to be treated. It may be preferable to choose sequences that are conserved between species to permit use in readily available animal models.

The present invention also provides compositions and methods for using ribozyme inhibitors for inhibiting I-mf expression. The ribozymes can be administered in a variety of ways, including by gene therapy targeted to a desired cell. A ribozyme of the invention is a targets the RNA transcripts of the gene of interest in a sequence-specific manner. For example, ribozymes may be designed to specifically inhibit the transcription of the I-mf gene Each ribozyme molecule is designed to contain a catalytically active segment capable of cleaving I-mf RNA, and further comprises flanking sequences having a nucleotide sequence complementary to portions of the targeted RNA. The flanking sequences serve to anneal the ribozyme to the RNA in a site-specific manner. Absolute complimentarity of the flanking sequences to the target I-mf sequence is not necessary, however, as only an amount of complimentary sufficient to form a duplex with the target RNA and to allow the catalytically active segment of the ribozyme to cleave at the target sites is necessary. Thus, only sufficient complimentary to permit the ribozyme to be hybridizable with the target RNA under physiological conditions is required.

As used herein, the term "ribozyme" means an RNA molecule having an enzymatic activity that is able to cleave or splice other separate RNA molecules in a nucleotide base sequence specific manner. By reference to catalytic or enzymatic RNA molecule is meant an RNA molecule which has complementarity in a substrate binding region to a specific RNA target (e.g. I-mf RNA), and also has enzymatic activity that is active to cleave and/or splice RNA in that target, thereby altering the target molecule. In preferred embodiments of the present invention the enzymatic RNA molecule is formed in a hammerhead motif, but the ribozyme may also be formed in the motif of a hairpin, hepatitis delta virus, group I intron or RNAse P RNA (in association with an RNA guide sequence). Examples of hammerhead motifs are described by Rossi et al., *AIDS Res. Hum. Retrovir.* 8: 183, 1992, hairpin motifs are described by Hampel et al., Biochem. 28: 4929, 1989 and Hampel et al., *Nucl. Acids Res.* 18: 299, 1990, the hepatitis delta virus motif is exemplified in Perrotta and Been, *Biochem.* 31: 16, 1992, an RNAseP motif is described in Guerrier-Takada et al., *Cell* 35: 849, 1983, and examples of the group I intron motif are described in Cech et al., U.S. Pat. No. 4,987,071, each of the foregoing disclosures being incorporated herein by reference. These specific motifs are not limiting in the present invention and those of skill in the art will recognize that an enzymatic RNA molecule of the invention has a specific substrate binding site which is complementary to one or more of the target RNA regions and that it has nucleotide sequences within or surrounding that substrate binding site which impart an RNA cleaving activity to the molecule.

The flanking sequences upstream and downstream of the ribozyme catalytic site may comprise segments of any length that effectively imparts the desired degree of targeting specificity for the ribozyme. Preferably a flanking sequence comprises from about 4 to about 24 nucleotides, more preferably from about 6 to about 15 nucleotides, and typically about 9 to 12 nucleotides, and results in base pairing to the substrate sequence immediately upstream and downstream of the RNA sequences which comprise the cleavage site.

The I-mf modulating agents, including I-mf inhibitors and agonists, of the present invention may be used in a variety of therapeutic contexts, alone or in combination, and may be formulated for a variety of modes of administration. Administration of the inhibitor or agonist may include systemic, topical or local administration. Techniques and formulations are generally described in *Remington's Pharmaceutical Sciences*, Mack Publishing Co., Easton, Pa., latest edition, incorporated herein by reference in its entirety. The inhibitor or agonist is generally combined with a pharmaceutically acceptable carrier such as a diluent or excipient. Suitable carriers may include fillers, extenders, binders, wetting agents, disintegrants, surface-active agents or lubricants. The choice of such ingredients will depend on the mode of administration and dosage forms. Typical dosage forms include tablets, powders, liquid preparation including suspensions, emulsions, and solutions, granules, capsules and suppositories. Liquid preparation for injection are also typical and include liposome preparations.

Polynucleotide inhibitors, e.g., triplex forming oligonucleotides, antisense oligonucleotide, ribozyme, etc., or a combination of such inhibitors targeted to different portions of the target DNA or corresponding RNA can be delivered in a wide variety of ways to targeted cells to facilitate inhibition of the gene of interest. Within one example, multiple polynucleotide inhibitors of I-mf are combined and delivered to target cells to decrease the expression of I-mf, thus, for example, permitting an increase in the expression or activity of endogenous MyoD family proteins. The oligonucleotides can be administered as synthetic oligonucleotides or expressed from an expression vector. The oligonucleotide can be administered ex vivo, i.e., contacted with target cells that have been removed from an individual or other cell source, treated and returned, or the oligonucleotide molecule can be administered in vivo. When administered ex vivo typically the target cells are exposed to mitogens, e.g., serum mitogens (SCF, IL-3, EPO, TPO, etc.) or the like depending on the particular cell population.

Delivery of inhibitors or agonists to a targeted cell population can be via a wide range of available delivery vehicles, e.g., a liposome, a controlled release vehicle, by use of iontophoresis, electroporation or ion paired molecules, or covalently attached adducts, and other pharmacologically acceptable methods of delivery. Preferably a carrier provides a means to accumulate the inhibitor or agonist within or at a desired cell population. The delivery vehicle can be designed to serve as a slow release reservoir or to deliver its contents directly to the target cell. Examples of oligonucleotide delivery vehicles include liposomes, hydrogels, cyclodextrins, biodegradable nanocapsules, and microspheres. Liposomes can readily be targeted to the various tissues or cell populations.

For in vivo use, routes of administration for I-mf inhibitors and agonists include intramuscular, aerosol, intravenous, parenteral, intraperitoneal, etc. The specific delivery route for a selected inhibitor or agonist will depend on a variety of factors, such as the form of the inhibitor or agonist, the intended target, the condition being treated, etc. For example, while unmodified oligonucleotide is taken up by cells, modifications can be made to enhance cellular uptake, e.g., by reducing the oligonucleotide's charge to produce a molecule which is able to diffuse across the cell membrane. The structural requirements necessary to maintain oligonucleotide activity and activity of other classes of inhibitors or agonists are generally recognized in the art. Modifications to enhance cellular delivery can also be designed to reduce susceptibility to nuclease digestion or other types of degradation.

The dosage of inhibitor or agonist will also depend on a variety of factors, such as the form of the inhibitor or agonist, the route of administration, etc., and thus can vary widely. Generally the dosage of inhibitors will result in inhibition of I-mf activity or levels to a sufficient extent within the targeted cells sufficient to prevent formation of I-mf complexes with its binding partners. Establishment of effective levels of inhibitor within a targeted cell population depends upon, e.g., the rate of uptake (or expression by a particular vector), and rate at which the inhibitor is degraded. The duration of treatment may extend for a time sufficient to permit, e.g., transduction of a relatively high percentage of dividing cells compared to an untreated control cell population, but usually will be at least for about 2–4 days, sometimes 6–10 days, although longer durations may be necessary for quiescent or terminally differentiated cell populations. The number and timing of doses can vary considerably, depending on the factors discussed above and the efficacy of a particular inhibitor or mixture thereof, the delivery vehicle and route of administration, etc.

For oligonucleotide inhibitors of the present invention, for example I-mf antisense oligonucleotide inhibitors or I-mf-specific triplex forming oligonucleotides, it may be preferable to include an effective concentration of a lipid formulation with the oligonucleotide. Suitable lipid formulations and concentrations are those that enhance the uptake of the oligonucleotides by cells. Such lipids include cationic lipids used for lipofection such as N-[1-(2,3-dioleyloxy)propyl-N, N,N-trimethylammonium chloride (DOTMA) and dioleoyl phophatidylethanolamine (DOPE). One skilled in the art may determine the particular lipid formulation or concentration that will be effective for enhancing the uptake of the oligonucleotide.

Within the methods described in detail herein, I-mf inhibitors or agonists may be used in combination with other compounds that are useful, for example in chemotherapy or as antibiotics. These compounds include standard chemotherapeutic agents such as platin compounds (e.g. cisplatin) and antibiotics such as penicillin, tetracycline or antiviral agents such as protease inhibitors and the like.

Within additional aspects of the invention, the I-mf encoding polynucleotide expression constructs disclosed herein are employed in methods for modulating the expression of I-mf, disrupting I-mf expression or inducing ectopic expression of I-mf genes and related polynucleotide sequences in the context of gene therapeutic methods involving mammalian host cells. In preferred gene therapeutic methods of the invention, an I-mf analog is expressed in mammalian cells that functions to impair anti-myogenic activities of endogenous I-mf, thereby restoring myogenic differentiation under the direction of MyoD family members. Introduction of the subject nucleotide sequences into cells may be accomplished in vitro or in vivo using a suitable gene therapy vector delivery system (e.g., a retroviral vector), a microinjection technique (see, for example, Tam, *Basic Life Sciences* 37: 187–194, 1986, incorporated by reference herein in its entirety), or a transfection method (e.g., naked or liposome encapsulated DNA or RNA) (see, for example, *Trends in Genetics* 5: 138, 1989; Chen and Okayama, *Biotechniques* 6: 632–638, 1988; Mannino and Gould-Fogerite, *Biotechniques* 6: 682–690, 1988; Kojima et al., *Biochem. Biophys. Res. Comm.* 207: 8–12, 1995; each incorporated by reference herein in its entirety). Gene transfer vectors (e.g., retroviral vectors, and the like) may be constructed wherein a polynucleotide molecule of the invention is inserted into the vector under the control of a promoter. Gene therapy may be used to correct conditions involving defective myogenic processes. The introduction method may be chosen to achieve a transient expression of I-mf in the host cell, or it may be preferable to achieve constitutive, tissue specific, or inducible expression.

Also provided within the invention are kits and multicontainer units comprising reagents and components for practicing the assay, screening, diagnostic and therapeutic methods of the invention. Exemplary kits of the invention contain reagents for detecting I-mf, I-mf-analogs, I-mf binding partners or the like, preferably included with selected additional reagents (e.g. enzymatic reagents such as reverse transcriptase or polymerase; suitable buffers; nucleoside triphosphates; suitable labels for labeling the reagents for detecting I-mf and developing reagents for detecting the signal from the label). In alternate examples, kits of the invention include sequence-specific oligonucleotide primers for detecting polynucleotide molecules encoding I-mf. Such primers may be provided in separate containers or may be provided in combinations of one or more primer pairs in a series of containers. Within yet another example, kits contain antibodies useful for detecting I-mf (or mutants thereof) in a sample. The I-mf-specific antibodies may be labeled or may be detected by binding to a secondary antibody. The antibody reagents may be provided in a separate container or may be provided in combination in a series of containers. In addition to these components, the kits may also contain instructions for carrying out the assay and/or additional containers suitable for carrying out the reactions of the assay.

The I-mf proteins, I-mf analogs, anti-I-mf antibodies and other subject molecules of the invention may also be utilized within diagnostic kits. In a preferred diagnostic kit, I-mf or I-mf analogs are provided in a lyophilized form or immobilized onto the walls of a suitable container, either alone or in conjunction with antibodies capable of binding to the I-mf or I-mf analog. The antibodies, which may be conjugated to a label or unconjugated, are generally included in the kits with suitable buffers, such as phosphate, stabilizers, inert proteins or the like. Generally, these materials are present in less than about 5% weight based upon the amount of I-mf or I-mf analog, and are usually present in an amount of at least about 0.001% weight. It may also be desirable to include an inert excipient to dilute the active ingredients. Such an excipient may be present from about 1% to 99% weight of the total composition. In addition, the kits will typically include other standard reagents, instructions and, depending upon the nature of the label involved, reactants that are required to produce a detectable product. Where an antibody capable of binding to I-mf is employed, this antibody will usually be provided in a separate vial. The antibody is typically conjugated to a label and formulated in an analogous manner with the formulations briefly described above. The diagnostic kits, including the containers, may be produced and packaged using conventional kit manufacturing procedures. Various other kits, including therapeutic kits, are contemplated within the invention that consolidate materials and facilitate performance of the methods described herein. In addition to providing desired components, the kits may also contain instructions for carrying out the methods of the invention.

The following examples are offered by way of illustration, not by way of limitation.

EXAMPLE 1

Yeast Two Hybrid Assay and Screening Methods

Complementary DNAs encoding proteins capable of interacting with the MyoD family of proteins were isolated using the two hybrid screen method essentially described by Fields and Song (*Nature* 340: 245, 1989 and U.S. Pat. No. 5,283,173; which are incorporated by reference herein in their entirety and modified as described herein). Yeast two-hybrid screens are reviewed as disclosed in Fields and Sternglanz (*Trends in Genetics* 10: 286–292, 1994; which is incorporated herein by reference in its entirety). The "bait" construct contained an expression vector encoding a LexA-MyoD fusion protein. To construct the "bait" plasmid, pLexAMyoD57–166, the MyoD insert from pEMSVMyoDΔNΔC (Weintraub et al. *Genes Dev.* 5: 1377–1386, 1991; which is incorporated herein by reference in its entirety) was obtained by PCR. The amplified fragment encoding amino acids 57–166 of MyoD, encompassing the most conserved C/H rich and bHLH domains, was fused to the LexA DNA binding domain and used as a "bait" by ligation in-frame into the pBTM116 vector (Bartel et al., *BioTechniques* 14: 920–924, 1993; which is incorporated herein by reference in its entirety) to obtain a Polynucleotide sequence encoding a LexA-MyoD fusion wherein neither the amino nor the carboxyl terminal sequence of MyoD containing activation domains were included. Plasmid pBTM116 is a yeast 2 μm-bearing vector containing a LexA expression vector containing the *S. cerevisiae* ADH promoter, the LexA DNA binding domain a polylinker site and a terminator sequence containing a termination codon in all frames. The *S. cerevisiae* Ade2 gene was isolated as a Bam HI fragment from pL909 plasmid (obtained from Ralph L. Keil, The Milton S. Hershey Medical Center, Hershey, Pa.; Stots and Linder, *Gene* 95: 91–98, 1990; which is incorporated herein by reference in its entirety) and subcloned into the unique Pvu II site of the "bait" plasmid to serve as a color indicator when screening for yeast transformants that lose "bait" constructs.

A mouse embryo cDNA fusion library containing random-primed mouse embryonic (E9.5 and E10.5) cDNA and VP16 activation domain was prepared as described by Hollenberg et al. (*Mol. Cell. Biol.* 15: 3813–3822, 1995; which is incorporated by reference herein in its entirety). Briefly, total RNA was isolated from CD1 mouse embryos stages E9.5 and E10.5 by solubilization of embryos in guanidinium isothiocyanate followed by pelleting of the RNA through a cesium chloride gradient cushion. Poly(A)$^+$ RNA was enriched by double passage through an oligo d(T) cellulose column. First strand cDNA synthesis was achieved by reverse transcription of 100 ng of RNA at 42° C. in 20 μl (microliters) of 500 pmol phosphorylated random hexamer and 50 U of Moloney murine leukemia virus reverse transcriptase (New England Biolabs) according to the manufacturer's instructions. Second strand synthesis was carried out using *E. coil* DNA polymerase I, *E. coil* DNA ligase and RNaseH. The resulting cDNAs were blunt ended with T4 DNA polymerase and Pol I (Klenow). After enzyme inactivation and DNA precipitation, the cDNA was ligated overnight with Not I adapters. Complementary cDNAs in the range of 350 to 700 nucleotides were purified by agarose gel electrophoresis. The cDNAs were amplified by PCR using primers corresponding to the Not I adapter. The amplified cDNAs were digested with Not I, purified by agarose gel electrophoresis and ligated into dephosphorylated, Not I-linearized pVP16 (described by Hollenberg et al., ibid.). The VP16 expression cassette in plasmid pVP16 contains, in order, a 1.5 kb *S. cerevisiae* ADH1 promoter fragment, and SP6 promoter, an initiator ATG, a nuclear localization signal, a VP16 activation domain, a Bam HI-Kpn I-Not-I polylinker and termination codons in all frames, and *S. cerevisiae* ADH1 termination sequences.

The two-hybrid screen was performed as described previously (Vojtek et al., *Cell* 74: 205–214, 1993 and Hollenberg et al., *Mol. Cell. Biol.* 15: 3813–3822, 1995; which are incorporated by reference herein in their entirety) with some modifications. The *S. cerevisiae* strain L40 containing multimerized LexA binding sites cloned upstream of two reporter genes, the HIS3 gene and the β-galactosidase gene which were each integrated into the L40 genome was used as the host strain for the screen. The host strain was transformed with the pLexAMyoD57–166 and subsequently transformed with the fusion library. Transformants were selected in medium lacking histidine, and the histidine-positive cells were assayed for β-galactosidase activity. The His$^+$LacZ$^+$ clones were plated out in cloning density on synthetic plates lacking leucine and containing 0.01 g/l of adenine. A single colony carrying only library constructs, indicated by its uniform red color, was selected from each clone for further analysis. Selected yeast clones were mated with AMR70 strain carrying LexA fusions containing lamin, the bHLH of daughterless (Da) or Thing1(Th1) (Hollenberg et al., ibid.) to identify false positive clones and encoding Id or E protein family members, respectively. The clones encoding members of the Id and E protein families were further confirmed by sequence analysis. From approximately 8×10$^6$ clones screened, 550 clones were selected that showed specific interaction with the MyoD bait. From this collection, about 130 clones were identified as cDNA fragments encoding members of the E protein family and 100 clones encoding Id family members, both of which are known HLH partners of MyoD. From the remaining clones, one gene called I-mf, which represented 15 independent VP16 fusions of 18 clones, was identified and characterized further.

EXAMPLE 2

Identification and Analysis of Complementary DNAs for I-mf a, I-mfb and I-mfc

Full length I-mf cDNA clones were obtained by screening an E10 and an E16 mouse embryonic library (Novagen, Madison, Wis.) using an I-mf cDNA fragment isolated from the two-hybrid screen as probe. One clone was isolated from a screen of 1×10$^6$ plaques from the E10 library. This clone was termed I-mfa. From 2×10$^6$ plaques screened from the E16 library, two identical clones, designated I-mfb, and one I-mfc clone were isolated. Each full-length cDNA of I-mfa, I-mfb or I-mfc was subcloned into pBluescript (Stratagene Cloning Systems; La Jolla, Calif.) and sequenced using the dideoxy nucleotide method on a series of nested exonuclease III deletions generated using an ERAS-A-BASE kit (Promega Corporation, Madison, Wis.) according to the manufacturer's instructions.

DNA sequencing and genomic mapping revealed that these three different transcripts are generated through differential poly-(A) adenylation and alternative splicing. The genomic organization of I-mf was analyzed from two overlapping genomic clones λ1 and λ2 covering 31.9 kb genomic sequences. Mapping demonstrated that the I-mf gene contains five exons, and that I-mfa, I-mfb and I-mfc are alternative splicing products of I-mf (FIGURE). The nucleotide sequences and deduced amino acid sequences of I-mfa, I-mfb and I-mfc are shown in SEQ ID NOS:1 and 2, 3 and 4, and 5 and 6, respectively. The deduced amino acid sequences suggested that the three I-mf proteins share a common amino terminal region, but each has a different carboxyl terminus. The I-mfa and I-mfb carboxyl termini were approximately equal in size, and comprise one third of each polypeptide. The third polypeptide, I-mfc, had a shorter unique carboxyl terminus. GenBank Database searches of the sequences of I-mf cDNA and deduced I-mf amino acid sequences revealed no homology with any known cDNA or protein. A search of the EST database identified a human fetal-lung cDNA that had high sequence similarity. This EST (Accession Number D31342; Sudo et al., *Genomics* 24: 276–279, 1994) overlapped exon IV and part of Exon V but does not overlap with the domain that interacts with and inhibits the MyoD family. The sequences of all 15 clones isolated from a random-primed two-hybrid library were overlapping, and all contained the unique carboxyl terminus of I-mfa. This result indicated that the unique carboxyl terminus of I-mfa, which is characterized by its high content of cysteine residues, is involved in the interaction with MyoD.

The chromosomal location of the mouse I-mf gene was localized by genetic linkage analysis using the Jackson backcross hybrid mapping panel to a region of chromosome 17 shown to be syntenic to a human chromosomal position of 6p21. Mutations at this location have been shown to be associated with the disease cleidocranial dysplasia (CCD). CCD occurs both as an autosomal dominant and a recessive mutation, and results in the delayed ossification of bones. Patients with CCD have bone deformation and in some cases some level of mental retardation.

EXAMPLE 3

Interaction between I-mfa and MyoD family members

A modified yeast one-hybrid system employing a β-galactosidase reporter was used to determine whether the full length I-mf and MyoD family members interact. Constructs containing full length mouse MyoD, Myf5 and Myogenin cDNAs were constructed by cloning PCR amplified protein coding regions of mouse MyoD, Myf5 and Myogenin cDNA, respectively, into yeast expression vector pEMBLye30/2 (Banroques et al., *Cell* 46: 837–844, 1986; which is incorporated herein by reference in its entirety) to obtain plasmids pEMBLMyoD, pEMBLMyf5 and pEMBLMyogenin. Plasmid pEMBLMyoD containing full length MyoD with its own transactivation domain was co-transformed with constructs containing the LexA DNA binding domain fused to full length I-mfa, I-mfb or I-mfc (LexA-I-mfa, LexA-I-mfb, LexA-I-mfc, respectively) into yeast strain L40 by the standard lithium acetate method.

The deduced protein coding regions of I-mfa, I-mfb and I-mfc were amplified by polymerase chain reaction to prepare fragments suitable for subcloning. Briefly, the deduced protein coding region of I-mfa was amplified using the sense primer of SEQ ID NO: 7(ACGAATTCCC AGG CCG ATG TCC CAG) and the antisense primer of SEQ ID NO: 8 (GTGCTCGAG CAC CCC ATG GCA TCA GGG). The PCR product was digested with Eco RI and Xho I and subcloned into the polylinker site of the mammalian expression vectors pCS2 (Rupp et al., *Genes Dev.* 8: 1311–1323, 1994; Turner and Weintraub, *Genes Dev.* 8: 1434–1447, 1994; which are incorporated by reference in their entirety) and pCS2HA to generate pCS-I-mfa and pCSHA-I-mfa, respectively. Similarly, the coding region of I-mfb was amplified and subcloned as described using the sense primer of SEQ ID NO: 7 and the antisense primer of SEQ ID NO: 9 (GTCCTCGAG GAC AAC TTA TTG GAG TTA) to generate pCS-I-mfb and pCSHA-I-mfb, respectively. The coding region of I-mfc was amplified and subcloned as described using the sense primer of SEQ ID NO: 7 and the antisense primer of SEQ ID NO: 10 (TAGCTCGAG CTA ACT GGT TCT GTC CTA) to generate pCS-I-mfc and pCSHA-I-mfc, respectively. Plasmid pCS2HA is a derivative of pCS2 that contains a 99 base pair insert encoding two haemaglutinin epitopes at the Cla I site of pCS2. To obtain the LexA-I-mfa and LexA-I-mfb fusion constructs, plasmids pCS-I-mfa and pCS-I-mfb were each digested with Eco RI and Hind III to obtain the I-mf coding sequences. Each I-mf fragment was blunt ended. The I-mfa fragment was inserted into Bam HI-linearized, blunt-ended pBTM116. A plasmid containing the I-mfa in the correct orientation relative to the promoter was designated pLexA-I-mfa. The I-mfb fragment was inserted into Eco RI-linearized, blunt-ended pBTM116. A plasmid containing the I-mfb in the correct orientation relative to the promoter was designated pLexA-I-mfb. To obtain the LexA-I-mfc fusion construct, plasmid pCS-I-mfc was digested with Ppu MI and Hind HI to obtain the I-mfc coding sequence. The fragment was blunt-ended and inserted into Bam HI, blunt-ended pBTM116. A plasmid containing the I-mfc insert in the correct orientation relative to the promoter was designated pLexA-I-mfc.

β-galactosidase activities were determined quantitatively on exponential phase L40 yeast cells transformed with pEMBLMyoD, pEMBLMyf5 or pEMBLMyogenin and either pLexA, pLexA-I-mfa, pLexA-I-mfb, pLexA-I-mfc or pLexA-DA (encoding a fusion protein containing LexA and a bHLH domain of Daughterless, the Drosophila homologue of mammalian E proteins) using a method described by (Trawick et al., *J. Biol. Chem.* 264: 7005–7008, 1989; which is incorporated by reference herein in its entirety) and modified as described herein. Control transformants included L40 cells co-expressing T3 and either LexA, LexA-I-mfa, LexA-I-mfb, LexA-I-mfc or LexA-DA; L40 cells co-expressing E12 and either LexA, LexA--mfa, LexA-I-mfb, LexA-I-mfc or LexA-DA; L40 cells co-expressing MyoDΔN-VP16 (a fusion protein containing the MyoD deletion mutant in which the amino-terminal amino acids 3–56 are deleted and the VP16 activation domain; described by Weintraub et al., ibid., 1991) and either LexA, LexA-I-mfa, LexA-I-mfb, LexA-I-mfc or LexA-DA; and MyoDΔC-VP16 (a fusion protein containing the MyoD termination mutant in which the amino acids C-terminal to amino acid 167 are deleted and the VP16 activation domain; described by Weintraub et al., ibid., 1991).

Briefly, cell pellets from 2 ml overnight cultures of each yeast transformant were suspended in 1 ml of Z buffer (60 mM Na$_2$HPO$_4$, 40 mM NaH$_2$PO$_4$, 10 mM KCl, 1 mM MgSO$_4$, at pH 7.0) containing 3.5 μl of β-mercaptoethanol and the OD$_{600}$ was measured. Cells were disrupted by adding 10 μl of chloroform and 10 μl of 0.1% sodium dodecyl sulfate followed by vigorous vortexing for 15 minutes. After disruption, 0.2 ml of 4 mg/ml o-Nitrophenyl-β-D-galactoside (ONPG) was added, and the mixture was incubated at 30° C. The reaction was stopped by the addition of 0.3 ml 1M Na$_2$CO$_3$ when the mixture turned yellow, and the incubation time was recorded. The OD$_{420}$ was measured on supernatant after cell debris was spun out. The β-galactosidase units were calculated using the formula: (OD$_{420}$×1000)/(OD$_{600}$×reaction time in minutes).

All of the LexA fusion proteins of appropriate size were expressed at similar levels when assayed by Western blot. As shown in Table 1, L40 expressing LexA, LexA-I-mfa, LexA-I-mfb or LexA-I-mfc exhibited background levels of β-galactosidase activities ranging from 0.1 to 0.9 (arbitrary units). However, 13-galactosidase activity was 5-fold higher than the LexA-I-mfa control in the same yeast strain bearing LexA-I-mfa and MyoD. In contrast, L40 expressing MyoD and LexA-I-mfb or LexA-I-mfc exhibited only background levels of β-galactosidase activity, indicating that MyoD interacted specifically with I-mfa in this assay, but not with I-mfb or I-mfc. The transactivation potency of all bHLH activators tested was also comparable to each other as assayed by the interaction with LexA-DA.

TABLE 1

Interaction of the MyoD Family and Hybrid I-mf Proteins in Yeast Strain L40

| | β-galactosidase activities in L40 yeast strains | | | | |
|---|---|---|---|---|---|
| | LexA | LexA-I-mfa | LexA-I-mfa | LexA-I-mfc | LexA-DA |
| Vector | 0.5 | 0.9 | 0.1 | 0.1 | 0.1 |
| MyoD | 0.6 | 4.3 | 1.1 | 0.4 | 12.5 |
| Myf5 | 0.9 | 68.5 | 0.4 | 0.4 | 12.1 |
| Myogenin | 0.6 | 63.6 | 0.4 | 0.3 | 28.6 |
| T3 | 1.6 | 2.3 | 0.9 | 0.1 | 12.9 |
| E12 | 2.3 | 2.3 | 0.6 | 1.4 | 25.0 |
| MyoDΔN-VP16 | 0.9 | 96.4 | N.D. | N.D. | 54.3 |
| MyoDΔC-VP16 | 0.6 | 5.6 | N.D. | N.D. | 146.5 |

The MyoD sequence used in the original isolation of I-mf is conserved among myogenic factors suggesting that I-mf may interact with other MyoD family members. Thus, the interaction between I-mf and other MyoD family members was determined using the same one-hybrid system described above using pEMBLMyf5 and pEMBLMyogenin. Using this system an interaction between I-mf and MyoD family members was detectable. In yeast co-expressing LexA-I-mfa and full length Myf5 or myogenin, β-galactosidase activity was about 70- to 80-fold higher than in those expressing LexA-I-mfa alone. Consistent with the MyoD result, the interaction with Myf5 or Myogenin was also specific to I-mfa (Table 1). In contrast, no stimulation of the β-galactosidase reporter gene was observed in L40 co-expressing any LexA-I-mf and either full length E12 or Lethal of Scute (AS-C T3), two other bHLH transcriptional activators (Table 1). The failure to detect significant interaction between LexA-I-mfa and E12 or T3 indicated that I-mfa interacts specifically with the myogenic family of bHLH proteins in this assay.

Physical association of I-mf and myogenic factors was demonstrated in an in vitro co-precipitation assay. DNA constructs encoding Maltose Binding Protein (MPB)-I-mf fusion proteins were constructed. PCR-amplified fragments containing either the full length coding region or amino acids 163 to 246 of I-mfa were cloned in-frame into pMAL-c2 (New England Biolabs, Inc., Beverly, Mass.) to construct pMBP-I-mfa and pMBP-I-mfaΔN, respectively. A Ppu MI/Hind HI fragment of I-mfc cDNA encoding full length I-mfc was cloned in-frame into pMAL-c2 to generate pMBP-I-mfc. An Eco O109I fragment of I-mfb cDNA, which contains amino acids 164 to 251 of I-mfb was cloned in-frame into pMAL-c2 to generate pMBP-I-mfbΔN.

MBP-I-mf fusion proteins were purified using a bacterial expression system as described (Vojtek et al., ibid.). Briefly, bHLH proteins (Myf5, MyoD, Myogenin and E12) were synthesized in vitro using a TNT-coupled reticulocyte system (Promega Corporation, Madison, Wis.) and labeled with $^{35}$S-methionine, according to the instructions of the manufacturer. For the in vitro association assay, appropriate aliquots of $^{35}$S-methionine labeled bHLH proteins were mixed with 1 µg of each purified MBP-I-mf fusion protein in 30 µl of phosphate-buffered saline (PBS). The reaction mixtures were incubated for 1 hour at room temperature, after which, 25 µl of a 50% suspension of amylose resin (New England Biolabs, Inc., Beverly, Mass.) and 1 ml of TNM buffer (20 mM Tris-HCl (pH 7.4), 150 mM NaCl, 5 mM MgCl$_2$, 0.1% NP-40) were added. The reactions were incubated for 30 minute at room temperature. The bound protein complex and resin were then washed five times with TNM buffer. Prior to analysis on SDS-polyacrylamide gel and detection by autoradiography, the bound proteins were eluted from the resin with 20 mM maltose in PBS.

Analysis of autoradiographs demonstrated that $^{35}$S-labeled in vitro translated Myf5, MyoD, and Myogenin were co-precipitated by the maltose binding protein-I-mfa fusion protein, MBP-I-mfa. In contrast, these myogenic factors were not co-precipitated in the presence of MBP-I-mfc. No significant association between E protein and I-mfa was detectable above background levels, indicating that I-mfa interacts specifically with MyoD family members in this assay.

To determine if the association between I-mfa and myogenic regulatory factors occurs in mammalian cells, an immunoprecipitation assay was performed on extracts from cells transiently co-transfected with pEMSVMyoD and an expression vector encoding haemaglutinin either (HA) epitope-tagged I-mfa (HA-I-mfa), HA-I-mfb or HA-I-mfc.

Expression vectors containing full length MyoD, Myf5 and Myogenin were constructed by subcloning the PCR amplified protein coding region of MyoD, Myf5 or Myogenin into the mammalian expression vector pEMSVscribe (Davis et al., *Cell* 51: 987–1000, 1987; which is incorporated herein by reference in its entirety) to create pEMSVMyoD, pEMSVMyf5 or pEMSVMyogenin. Briefly, NIH3T3 cells were co-transfected with pEMSVMyoD and either pCSHA-I-mfa, pCSHA-I-mfb, or pCSHA-I-mfc. Cell extracts were made 40 hours post transfection by sonication in TNM buffer containing 50 µg/ml of Pefabloc (Boehringer Mannheim; Indianapolis, Ind.), 2 µg/ml of Leupeptin, 1 µg/ml of Aprotinin. After sonication, either 5 µl of MyoD antiserum 5.8A (Tapscott et al., *Science* 242: 405–411, 1988; which is incorporated herein by reference in its entirety) or anti-HA epitope antibody 12CA5 (Boehringer Mannheim; Indianapolis, Ind.) and 25 µl of a 50% suspension of protein A agarose were added to the appropriate aliquot of cell extract in 1 ml TNM buffer containing the same proteinase inhibitors. The protein A agarose complexes were washed 5-times with TNM buffer after a 1.5 hour incubation at 4° C. Protein complexes were eluted with SDS protein sample buffer prior to analysis by Western blotting using peroxidase conjugated anti-HA (12CA5) antibody (Boehringer Mannheim, Indianapolis, Ind.) and the ECL detection system (Amersham Life Science, Arlington Heights, Ill).

Western analysis demonstrated that HA-I-mfa, but not HA-I-mfb or HA-I-mfc, was co-precipitated by MyoD antiserum in the presence of MyoD protein. Similar results were obtained with Myf5 antiserum in extracts from cells expressing Myf5 and either HA-I-mfa, HA-I-mfb or HA-I-mfc. These results demonstrated that I-mfa and MyoD family members are specific binding partners in vivo.

EXAMPLE 4

Interaction with Specific Domains of MyoD

To further map the detailed I-mfa-interactional domain from MyoD, LexA fusion constructs containing a series of MyoD deletions were made by cloning the PCR products of MyoD mutants from their corresponding pEMSV plasmids (Weintraub et al., *Genes Dev.* 5: 1377–1386, 1991; which is incorporated herein by reference. Briefly, MyoD deletion mutant sequences in DM3-56/TM167, DM3-74/TM167, DM3-92/TM167, DM4-101/TM167 and DM4-140/TM167 were amplified using oligonucleotide primers of SEQ ID NO: 11 (CTGAATTCC AGG AAC TGG GAT ATG) and of SEQ ID NO: 12 (GTTGGATCC TCA AAG CAC CTG ATA AAT CG), which hybridized to flanking sequence common to all the plasmids. The PCR products were cloned in-frame into plasmid pBTM116. The Pml I/Stu I, Pml I/Sty I, Pml I/Nar I or Pml/Mlu I fragments were cloned in-frame into pBTM116 to generate LexA-MyoD:dDM53/127, dDMD53/146, dDM53/173 and dDM53/199 respectively. Table 2 shows the LexA-MyoD mutant fusion proteins and the amino acids of MyoD that are deleted.

TABLE 2

| Fusion Construct | Amino Acids Deleted from MyoD |
|---|---|
| LexA-MyoD:DM3-56/TM167 | Amino Acids 3–56 and 168–318 |
| LexA-MyoD:DM3-74/TM167 | Amino Acids 3–74 and 168–318 |
| LexA-MyoD:DM3-92/TM167 | Amino Acids 3–92 and 168–318 |
| LexA-MyoD:DM4-101/TM167 | Amino Acids 4–101 and 168–318 |
| LexA-MyoD:DM4-140/TM167 | Amino Acids 4–140 and 168–318 |
| LexA-MyoD:dDM53/127 | Amino Acids 1–53 and 128–318 |
| LexA-MyoD:dDM53/146 | Amino Acids 1–53 and 147–318 |
| LexA-MyoD:dDM53/173 | Amino Acids 1–53 and 174–318 |
| LexA-MyoD:dDM53/199 | Amino Acids 1–53 and 200–318 |

The mutant constructs described above were each co-expressed with the VP16 fusion proteins containing the full length I-mfa in the L40 yeast strain. β-Galactosidase levels were determined to measure the interaction between I-mfa and the MyoD mutants. This analysis demonstrated that MyoD amino acids 93–101, containing a partial C/H (cysteine/histidine) rich region, and amino acids 128–146, containing the Helix 1 and loop regions, were required for specific interaction with I-mfa. Helix 2 of MyoD was dispensable for this interaction; however it was required for dimerization with bHLH proteins. The bHLH domain of MyoD was sufficient for dimerization with bHLH proteins; however, it was not sufficient for interaction with I-mfa. This was shown by the low level of β-Galactosidase expressed in cells co-expressing LexA-MyoD:MD4-140/TM167 (the bHLH domain) and I-mfa-VP16 relative to the high level of β-Galactosidase expressed in cells co-expressing LexA-MyoD:MD4-140/TM167 and Myf5. These results suggested that the I-mfa-interactional domain from MyoD was located in amino acids 93–146, which encompasses the C/H rich, basic, Helix I and loop regions. This region overlaps, but is not identical to, the domains required for interactions between bHLH proteins.

To further determine whether the unique carboxyl terminal domain of I-mfa is sufficient for interaction with MyoD, a series of LexA fusion constructs were prepared containing deletion mutants of I-mfa. The deletion mutant fusions were constructed by cloning the corresponding PCR products of I-mfa in-frame into pBTM116. Oligonucleotide primers of SEQ ID NO: 13 (ACGGAT CCC AGG CCG ATG TCC CAG) and of SEQ ID NO: 14 (CTCTCGAGTCA GCA GCA GCA GAG GCA GGA G) were used to amplify the region encoding I-mfa amino acids 1–202. The resulting fragment was subcloned in-frame into pBTM116 such that the resulting vector encodes a LexA-I-mf fusion or in-frame into pCS2HA such that the resulting vector encodes an HA-I-mf. Oligonucleotide primers of SEQ ID NO: 15 (ACGGAT CCC CAG ACC ATG TCC CTC CTC) and of SEQ ID NO: 16 (GTGCTCGAG CAC CCC ATG GCA TCA GGA) were used to amplify the region encoding I-mfa amino acids 29–246, and the PCR product was subcloned into pBTM116 and pCS2HA as described above. Oligonucleotide primers of SEQ ID NO: 17 (CAGAATTCA CAG CCT CAA GGG AAC CCC) and of SEQ ID NO: 16 were used to amplify the region encoding I-mfa amino acids 87–246, and the PCR product was subcloned into pBTM1 16 and pCS2HA as described above. Oligonucleotide primers of SEQ ID NO: 18 (GTGAATTCA GAT TGC TGC GTC CAC TGC) and of SEQ ID NO: 16 were used to amplify the region encoding I-mfa amino acids 163–246, and the PCR product was subcloned into pBTM1 16 and pCS2HA as described above. Oligonucleotide primers of SEQ ID NO: 19 (GTGAATTCC TGC TGT GGG TCC GGC GAG) and of SEQ ID NO: 16 were used to amplify the region encoding I-mfa amino acids The LexA-I-mfa fusion mutants were also co-expressed with VP16-I-mfa, VP16-I-mfb, or VP16-I-mfc. The results the O-Galactosidase activities suggested that I-mfa was able to interact with I-mfa itself, but not with I-mfb or I-mfc. The domain required for this self-interaction was located in the same region required for interaction with myogenic factors. However, unlike the Myf5-interactional domain, amino acids 87–163 of SEQ ID NO: 2 from the common region of I-mfa was able to enhance the self-interaction as determined by comparing the results of cells co-expressing VP16-I-mfa and LexA-I-mfa(87–246) or LexA-I-mfa(163–246) and of cells co-expressing VP16-I-mfa and LexA-I-mfa(87–202) or LexA-I-mfa(163–202) (Table 3).

TABLE 3

Analysis of the I-mfa Domain Required for Interacting with Myf5 or I-mfa Itself

| | β-Galactosidase activities in L40 yeast strains | | | | |
|---|---|---|---|---|---|
| | Myf5 | VP16-I-mfa | VP16-I-mfb | VP16-I-mfc | VP16 |
| LexA-I-mfa (1-246) | 66.0 ± 0.9 | 6.4 ± 0.1 | 0.7 ± 0.2 | 0.5 ± 0.2 | 0.5 ± 0.3 |
| LexA-I-mfb | <0.1 | 0.2 | <0.1 | <0.1 | <0.1 |
| LexA-I-mfc | <0.1 | <0.1 | <0.1 | <0.1 | <0.1 |
| LexA-I-mfa (1-202) | 34.5 ± 1.2 | 95 ± 0.2 | <0.1 | <0.1 | <0.1 |
| LexA-I-mfa (29-246) | 84.7 ± 3.1 | 10.1 ± 2.5 | 0.7 ± 0.2 | 0.8 ± 0.1 | 0.8 ± 0.3 |
| LexA-I-mfa (87-246) | 74.3 ± 1.1 | 12.5 ± 1.0 | 0.6 ± 0.2 | 0.7 ± 0.1 | 0.8 ± 0.5 |
| Lex-I-mfa (163-246) | 71.3 ± 12.5 | 3.8 ± 1.2 | 0.6 ± 0.2 | 0.2 | 0.3 |
| LexA-I-mfa (203-246) | 57.2 ± 23.1 | 95.2 ± 34.9 | 39.2 ± 5.0 | 52.3 ± 8.1 | 45.8 ± 30.7 |
| LexA-I-mfa (87-202) | 27.6 ± 0.1 | 9.3 ± 0.6 | 0.2 | <0.1 | <0.1 |
| LexA-I-mfa (87-202) | 57.1 ± 0.2 | 4.3 ± 1.8 | 0.2 | <0.1 | <0.1 |

203–246, and the PCR product was subcloned into pBTM1 16 and pCS2HA as described above. Oligonucleotide primers of SEQ ID NO: 17 and of SEQ ID NO: 14 were used to amplify the region encoding I-mfa amino acids 87–202, and the PCR product was subcloned into pBTM116 and pCS2HA as described above. Oligonucleotide primers of SEQ ID NO: 18 and of SEQ ID NO: 14 were used to amplify the region encoding I-mfa amino acids 163–202, and the PCR product was subcloned into pBTM1 16 and pCS2HA as described above.

The LexA-I-mfa fusion mutants were co-transformed with pEMBLMyf5 into the yeast strain L40. The interaction between each fusion mutant and Myf5 was indicated by β-Galactosidase activity which was assayed as described herein. The region of I-mfa common to all three I-mf proteins (amino acids 1–162 of SEQ ID NOS: 2, 4, and 6) was not required for interaction with Myf5 as suggested by the high level of β-Galactosidase expressed in cells co-expressing Myf5 and LexA-I-mfa(163–246). The carboxyl-terminal half of the domain unique to I-mfa was also dispensable for this interaction, as deduced from the level of β-Galactosidase in cells co-expressing Myf5 and LexA-I-mfa(1–202). The smallest interactional domain that retained activity among those deletion mutants tested was located in a 40 amino acid segment (from amino acids 163–202 of SEQ ID NO: 2) encompassing the amino-terminal half of the unique domain of I-mfa.

To determine if the minimal interactional domain of I-mfa is responsible for I-mfa repression activity, the deletion mutants cloned into the mammalian expression vector pCS2HA were co-expressed with pEMSVMyf5 and the p4R-TK-CAT reporter in NIH3T3 cells. Plasmid p4R-TK-CAT is a modification of the plasmid TK-CAT in which four oligomerized MyoD binding sites are inserted upstream of TK. CAT activity levels were determined for the transfected cells as described above (Gorman et al., Mol. Cell. Biol. 2: 1044–1051, 1982; which is incorporated herein by reference in its entirety). The CAT activities were normalized to the value from Myf5 or E12 co-transfected with pCS2HA, which were set to 100 (Table 4). By CAT assay, the minimal interactional domain of I-mfa (amino acids 163–202 of SEQ ID NO: 2) repressed 55% of the Myf5 transactivation activity. The larger polypeptide (amino acids 87–202 of SEQ ID NO: 2) demonstrated 93% inhibition. Western blot analysis demonstrated that the minimal interactional domain of I-mfa (amino acids 163–202 of SEQ ID NO: 2) was less stable than the larger polypeptide (amino acids 87–202 of SEQ ID NO:2). This explained the weaker repression activity of the minimal interactional domain of I-mfa. Consistent with the transactivation analysis, Myf5-mediated muscle conversion, assayed by MyHC expression (described in more detail below) was also repressed in a similar way by the deletion mutants. These results indicated that the minimal interactional domain of I-mfa possesses a range of anti-myogenic activities that regulate MyoD transcription factor activities.

TABLE 4

Analysis of the I-mf Domain Required for the Inhibition of Myf5 Activity

| I-mf | CAT (%) +Myf5 | CAT (%) +E12 | muscle conversion | Interaction with Myf5 |
|---|---|---|---|---|
| Vector | 100 | 100 | +++ | – |
| Imfa (1-246) | 2 ± 1 | — | — | + |
| I-mfb | 74.5 ± 15 | 100 | +++ | – |
| I-mfc | 65 ± 10 | 99 | +++ | – |
| I-mfa (1-202) | 5 ± 2 | 113 | – | + |
| I-mfa (29-246) | 4 ± 2 | 81 | – | + |
| I-mfa (87-246) | 2 ± 1 | 53 | – | + |
| I-mfa (163-246) | 2± 1 | 18 | – | + |
| I-mfa (203-246) | 78 ± 11 | 93 | +++ | N.D. |
| I-mfa (87-202) | 7 ± 2 | 89 | + | + |
| I-mfa (103-202) | 44 ± 4 | 98 | ++ | – |

In the yeast assay system, I-mfa interacts with MyoD more weakly than with Myf5 or Myogenin (Table 1); analysis of various MyoD-deletion constructs suggests this weak interaction between MyoD and I-mfa is likely due to interference from the amino terminus of MyoD (Table 1). However, it is unclear if I-mfa associates more weakly with MyoD than with other myogenic regulatory factors in mouse embryos. I-mfa also had slightly weaker effects on MyoD than on the other myogenic factors tested in both transactivation repression and cytoplasmic retention assays.

EXAMPLE 5

I-mfa Function in Myogenesis

To investigate the possible function of J-mf in embryonic myogenesis, the expression pattern of I-mfa during mouse embryogenesis was determined by in situ hybridization as generally described by Lee et al. (in commonly assigned, co-pending international patent application WO 95/30693; and *Science* 268: 835–844, 1995; which are incorporated herein by reference in their entirety) and Hurlin et al. (*EMBO J.* 14: 5646–5659, 1995; which is incorporated herein by reference in its entirety). Briefly, mouse embryos at E11.5 from inbred strain BL/6 were collected for RNA in situ hybridization. The embryos were staged such that the day of the vaginal plug was considered as embryonic day 0.5 (E0.5). The embryos were fixed, paraffin embedded and sectioned before hybridization.

Digoxygenin labeled antisense RNA corresponding to full length cDNA of murine MyoD (1.8 kb), murine Myf5 (from the 424 bp Dra I restriction fragment of the 5' untranslated region), and I-mfa (SEQ ID NO: 2; from amino acid 71 to 34 bp downstream of its stop codon (560 bp)) were used as probes for hybridization. Parasagittal sections of the E11.5 embryos were examined by in situ hybridization with the antisense probes. As a comparison, sections adjacent to those examined for I-mfa expression were hybridized with the MyoD antisense riboprobe.

I-mfa transcripts were highly expressed in the sclerotome. However, the expression of MyoD was concentrated in the myotome. No specific hybridization was found when the corresponding I-mfa sense riboprobe was used in control in situ hybridization. The transverse sections of caudal somites of the same stage embryos showed high level of I-mfa expression in the sclerotome, the ventral subdomain of the somites, while Myf5 was detected exclusively in the myotome part of dermomyotome, the dorsal subdomain of somites. A similar expression pattern of I-mfa was also observed in newly formed somites of E8.5 mouse embryos. These results demonstrated a mutually exclusive pattern of high level expression of I-mfa and the MyoD family members in mouse somites.

In addition to its expression in somites, I-mfa was also shown to be expressed in the notochord and at lower levels in the neural tube as well as in limb buds, heart, branchial arches, head mesenchyme and various other parts of the mouse embryo. Moreover, analysis of RNA from various mouse tissues revealed that I-mfa was most highly expressed in skeletal tissue, but was expressed at lower levels in almost every other tissue analyzed. Early in development I-mfa was highly expressed in the sclerotomal domain of somites. In contrast, myogenic factors were detected in the dermomyotomal domain of somites.

EXAMPLE 6

I-mfa Inhibits the MyoD Family-Dependent Transcriptional Activation

The accumulation of I-mfa transcripts and the transcripts of members of the MyoD family in a mutually exclusive fashion in differentiating somites suggested that I-mfa plays an important role in regulating the expression/function of the MyoD family. The ability of MyoD family members to transactivate an E box-driven reporter construct was assayed in the presence or absence of I-mf to determine if I-mf influences the activity of myogenic factors. Transactivation was assessed by using the E box-driven reporter construct, p4R-TK-CAT (Weintraub et al., *Genes Dev.* 5: 1377–1386, 1991) which contained a chloramphenicol acetyltransferase (CAT) reporter gene controlled by four copies of the E box sequences. Expression vectors containing full length Myf5 were constructed by subcloning the PCR amplified protein coding region of Myf5 into the mammalian expression vector pCS2NLS (Rupp et al., ibid., 1994) to create pCSNLSMyf5.

NIH3T3 cells were grown in Dulbecco's modified Eagle's medium (DMEM) supplemented with 10% fetal calf serum on 10 cm dishes. The cells were transfected using the calcium phosphate precipitation method (Davis et al., *Cell* 60: 733–746, 1990; which is incorporated herein by reference) with 5 µg of the p4R-TK-CAT reporter construct and each possible combination of 5 µg of pEMSVMyf5 or pEMSVMyogenin and 5 µg of either pCSHA-I-mfa, pCSHA-I-mfb, or pCSHA-I-mfc. In addition, every combination of 3 µg of each I-mf vector and 3 µg of each myogenic expression plasmid were transfected into cells on 6 cm plates using the calcium phosphate precipitation method. The following day, the cells were rinsed with PBS and incubated for 10 hours in DMEM plus 10% calf serum. After the incubation, the cells were switched into differentiation medium, DMEM plus 2% horse serum, for an additional 40 hours. Cells were harvested and CAT assays were performed as described above or fixed for indirect immunofluorescence staining.

Indirect immunofluorescence staining was carried out on transfected cells that were fixed in PBS with 4% paraformaldehyde for three minutes and permeabilized in PBS with 0.25% Triton X-100 for three minutes. The fixed cells were stained with anti-Myf5 polyclonal antibody (Santa Cruz Biotechnology, Santa Cruz, Calif.), and anti-myosin heavy chain monoclonal antibody MF20 (Boehringer Mannheim, Indianapolis, Ind.) or anti-HA monoclonal antibody, 12CA5

(Boehringer Mannheim, Indianapolis, Ind.). Fluorescein (DTAF)-conjugated donkey anti-rabbit Ig and Rhodamine (TRITC)-conjugated goat anti-mouse Ig (Jackson ImmunoResearch Laboratories, West Grove, Pa.) were subsequently used for indirect fluorescence detection.

Analysis showed that I-mfa reduced the transactivation activity of all three myogenic factors tested to 10 to 23% of the control level (Table 5). In contrast, I-mfb and I-mfc showed no significant effect on the myogenic factor-dependent reporter activation. Moreover, I-mfa did not significantly inhibit the transactivation activity of E12, when pCS-I-mfa and an analogous E12 construct were co-transfected with the p4R-TK-CAT reporter construct (Table 5). The relative value of 100% in MyoD, Myf5, Myogenin and E12 plus control vector transfected cells represented absolute CAT values of 55,400, 53,070, 17,430 and 53,570, respectively. Comparable expression levels and appropriate size I-mfa, I-mfb and I-mfc were confirmed by Western blot analysis. These results demonstrated that I-mfa was not a general repressor of bHLH transcriptional activators.

TABLE 5

The Effects of I-mf on the Transactivation Activities of the MyoD Family

| | Relative CAT Activity (%) | | | |
|---|---|---|---|---|
| | MyoD | Myf5 | Myogenin | E12 |
| Vector | 100 | 100 | 100 | 100 |
| I-mfa | 10.6 ± 2.3 | 0.9 ± 0.1 | 1.5 ± 0.1 | 76.3 ± 10.9 |
| I-mfb | 96.5 ± 1.7 | 94.8 ± 0.8 | 82.7 ± 10.2 | 98.7 ± 1.6 |
| I-mfc | 96.1 ± 0.4 | 96.4 ± 0.9 | 68.0 ± 5.6 | 93.8 ± 4.7 |

Transient transfections of NIH3T3 fibroblasts with mixtures of p4R-TK-CAT (5 µg) plus MyoD or Myf5 expression vectors (2 µg) in the presence of increasing amounts of I-mfa expression vectors were assayed for relative CAT activity level. To normalize the DNA mass, the total amount of DNA in each precipitate per 10 cm recipient plate was brought to 15 µg with the expression vector pCS2. CAT activity in each experiment was normalized to the zero I-mfa data point to permit direct comparison of I-mfa dose. The results demonstrated that I-mfa activity of repressing myogenic regulatory factor activity occurs in a dose-dependent manner.

MyoD and Myf5 were each transiently co-expressed with either I-mfa, I-mfb or I-mfc in mouse C3H10T1/2 cells (C3H/10T1/2; Accession No. CCL 226, American Type Culture Collection, 12301 Parklawn Drive, Rockville, Md. 20852) containing p4R-TK-CAT. The CAT activity from the co-transfections were normalized to the value from each co-transfection with empty vector to allow direct comparison of I-mf activity associated with each myogenic factor. The 100% value in MyoD and Myf5 plus control vector transfected C3H10T1/2 cells were 89,453 and 109,657, respectively. The results demonstrated that I-mfa anti-myogenic activity occurred in C3H10T1/2 cells cultured in either growth medium or differentiation medium (Table 6).

TABLE 6

I-mf Inhibits Transactivation Activities of Myogenic Factors on Different Reporter Constructs and in Different Cell Lines Relative CAT Activity (%)

| | MCK-CAT (NIH3T3 cells) | | | 4RCAT (10T/2 cells) | |
|---|---|---|---|---|---|
| | MyoD | Myf5 | Myogenin | MyoD | Myf5 |
| Vector | 100 | 100 | 100 | 100 | 100 |
| I-mfa | 27 | 9 | 2 | 56 | 13 |
| I-mfb | 87 | 132 | 101 | 95 | 105 |
| I-mfc | 100 | 106 | 111 | 100 | 101 |

MyoD, Myf5 and Myogenin were each transiently co-expressed with either I-mfa, I-mfb or I-mfc in NH3T3 cells containing p4R-TK-CAT. The CAT activity was normalized as described previously. The 100% value in MyoD, Myf5 and Myogenin plus control vector transfected NIH3T3 cells were 37,168, 79,532 and 32,968, respectively. The results demonstrated that I-mfa repression of myogenic regulatory factor activity occurred when assayed on a CAT reporter driven by 3.3 kb of the muscle-specific MCK promoter (Table 6). Taken together, these results indicated that I-mfa acts to repress the transactivation activity of the MyoD family independent of cell type, culture conditions and reporter constructs used.

EXAMPLE 7

I-mfa Inhibits the Myf5-Mediated Muscle Differentiation

To investigate whether I-mf can inhibit MyoD family-dependent myogenesis, I-mfa and Myf5 were co-expressed transiently in NIH3T3 fibroblasts as described above, and muscle differentiation was assayed by the appearance of the specific muscle marker myosin heavy chain (MyHC), as well as by cellular morphology. The cells were co-transfected with pEMSVMyf5 and either the control vector pCS2, pCS-I-mfa, pCS-I-mfb or pCS-I-mfc. Twenty-four hours after transfection, cells were grown in differentiation medium for an additional 40 hours before staining. After incubation in the differentiation medium, the cells were fixed in PBS with 4% of paraformaldehyde for 3 minutes and permeabilized in PBS with 0.25% Triton X-100 for 3 minutes. The fixed cells were double stained with a Myf5 antiserum (Santa Cruz Biotechnology, Santa Cruz, Calif.) and the anti-myosin heavy chain monoclonal antibody, MF20 followed by incubation with fluorescein (DTAF)-conjugated donkey anti-rabbit Ig and Rhodamine (TRITC)-conjugated goat anti-mouse Ig (Jackson ImmunoResearch Laboratories, West Grove, Pa.). The images of the labeled cells were superimposed.

When co-transfected with Myf5 and different control vectors, about 80% of the Myf5 positive cells expressed MyHC and differentiated into elongated myotubes. However, consistent with the repressor activity of I-mfa, cells expressing both I-mfa and Myf5 demonstrated no MyHC expression and repression of muscle differentiation (retention of fibroblast morphology); about 80% of the cells expressing both Myf5 and I-mfa showed no MyHC expression and retained their fibroblast morphology. I-mfa also inhibited MyoD and Myogenin-mediated muscle differentiation. These results indicated that I-mfa anti-myogenic activities include inhibition of MyoD family-mediated muscle differentiation in tissue culture cells.

EXAMPLE 8

I-mfa Retains MyoD Family Members in the Cytoplasm by Masking their Nuclear Localization Signals To determine whether the cytoplasm-expressed Myf5 was co-localized with I-mfa, NIH3T3 cells were co-transfected with pEMSVMyf5 and either pCSHA-I-mfa, pCSHA-I-mfb or pCSHA-I-mfc. Indirect immunofluorescence staining was performed as described above using an anti-Myf5 polyclonal (Santa Cruz Biotechnology, Santa Cruz, Calif.) and the anti-HA monoclonal 12CA5 (Boehringer Mannheim, Indianapolis, Ind.) antibodies. Analysis of stained cells demonstrated that I-mfa protein was distributed primarily throughout the cytoplasm, although weak staining was detectable in the nucleus. This subcellular localization did not change in the presence of Myf5. In the absence or in the presence of I-mfb or I-mfc, Myf5 was localized exclusively in the nucleus. In contrast, when co-expressed with I-mfa, Myf5 protein co-localized with I-mfa in the cytoplasm.

Co-localization assays were also carried out on cells co-expressing I-mfa and MyoD, Myogenin or Myc-epitope-tagged E47. NHDT3 cells were transiently transfected with pCSHA-I-mfa and either pEMSVMyoD, pEMSVMyogenin or pEMSVE47. Forty hours after transfection, the corresponding cells were immunostained with polyclonal MyoD antiserum, Myogenin monoclonal antibody, F5D (obtained from Dr. Wood Wright, University of Texas Southwestern Medical Center, Dallas, Tex.; Cusella-DeAngelis et al., Cell Biol. 116: 1243–1255, 1992) or the Myc epitope monoclonal antibody, 9E10 (Evan et al., Mol. Cell. Biol. 5: 3610–3616, 1985; which is incorporated herein by reference in its entirety) as described above. These assays revealed that I-mfa retained Myogenin equally well in the cytoplasm, but it retained MyoD to a lesser degree. The I-mfa-mediated cytoplasmic retention is considered specific to myogenic factors, since the nuclear localization of E protein remained unchanged when co-expressed with I-mfa. These results indicated a correlation among the binding, repression and cytoplasmic retention of the MyoD family by I-mfa.

MyoD has two nuclear localization signals (NLS), one in the basic region and one in the helix 1 domain (Vandromme et al., Proc. Natl. Acad. Sci. USA 92: 4646–4650, 1995). The location of these NLS overlaps with the I-mf interaction region, raising the possibility that I-mfa may simply mask the NLS of the MyoD family members, resulting in their cytoplasmic retention. If this masking hypothesis were correct, adding a presumably unmasked NLS outside of the C/H rich and bBLH regions of myogenic regulatory factors should restore their nuclear localization. To test this hypothesis, an expression plasmid was constructed containing one SV40 T antigen NLS added to the amino terminus of Myf5, designated pCS2NLSMyf5. This construct was co-transfected with pCSHA-I-mfa and visualized by indirect immunostaining as described previously. When co-expressed with I-mfa in NIH3T3 cells, NLSMyf5 localized exclusively in the nucleus. A similar "nuclear rescue" was observed when plasmids pCS2NLSMyogenin and pCS2NLSMyoD (constructed by inserting the PCR amplified coding regions of Myogenin or MyoD into pCS2NLS to add the SV40 T antigen NLS to the amino terminal coding region of Myogenin or MyoD) were co-transfected with pCSHA-I-mfa.

The in vitro binding of I-mfa to NLSMyogenic factors was assessed. Briefly, plasmids pEMSVMyf5, pEMSVMyogenin, pEMSVMyoD, pCS2NLSMyf5 and pCS2NLSMyogenin were in vitro translated as described previously. The labeled proteins were divided and one portion was subjected to co-precipitation with amylose resin following incubation with the purified Maltose Binding Protein-I-mf fusion, MBP-I-mfaΔN, which contains amino acids 163 to 246 of I-mfa as previously described. SDS-polyacrylamide gel electrophoresis on the in vitro and co-precipitated samples demonstrated that I-mfa associates as a binding partner equally well with NLSMyf5 and Myf5.

Gel shifting assays were performed as described (Davis et al., Cell 60: 733–746, 1990; which is incorporated herein by reference in its entirety). In brief, in vitro translated myogenic factors (both full length Myf5 and NLSMyf5) were mixed with purified bacterially expressed MBP-I-mfaΔN. The samples were incubated for 10 minutes at 37° C. Prior to their analysis by gel electrophoresis in 0.5× TBE, the mixtures were incubated for 10 minutes with cocktails containing buffer, dIdC and $^{32}$P-labeled B1/B2 probe (Davis et al., ibid., 1990), containing E box sequences from the MCK promoter. As with the co-precipitation assay, the gel-shifting assay demonstrated that I-mfa associates equally well with NLSMyf5 and Myf5. These results indicated that it was unlikely that the nuclear rescue was due to a failure in association between NLSMyf5 and I-mfa. Thus, the rescue of nuclear localization of Myf5 by the SV40 NLS indicated that I-mfa sequesters myogenic regulatory factors in the cytoplasm through direct protein interaction with MyoD family binding partners which masks the NLS of these myogenic factors.

EXAMPLE 9

I-mfa Interferes with the DNA Binding Activity of the Mod Family Members

To determine if the rescue of nuclear localization was sufficient to restore Myf5-mediated myogenesis in the presence of I-mfa, the expression of MyHC in NIH3T3 cells transiently transfected with Myf5 and I-mf constructs were examined. NIH3T3 were transiently transfected with pCS2NLSMyf5 and either pCSHA-I-mfa or pCSHA-I-mfc as described previously. Twenty-four hours post-transfection, cells were grown in differentiation medium for an additional 40 hours before they were stained with antibodies. Double immunostaining was performed with Myf5 antiserum (Santa Cruz, Santa Cruz, Calif.) and the anti-MyHC monoclonal antibody, MF20 (Boehringer Mannheim), followed by staining with Fluorescein conjugated anti-rabbit Ig antibody and Rhodamine conjugated anti-mouse Ig antibody, respectively. The staining images were superimposed. Expression of NLSMyf5 alone induced MyHC expression in transfected NIH3T3 cells to a similar extent as wild type Myf5. In contrast, when co-expressed with I-mfa, most NLSMyf5-expressing cells did not express detectable MyHC protein, similar to what was observed with Myf5 in the presence of I-mfa. This result indicated that the nuclear NLSMyf5 was functionally impaired in the presence of I-mfa. In a parallel experiment, the transactivation activity of NLSMyf5 was also repressed by I-mfa using the CAT activities determined as described previously (Table 7). These results implied that the sequestration of myogenic regulatory factors in the cytoplasm was not the sole mechanism by which I-mfa inhibits the activities of the MyoD family members.

TABLE 7

The Effect of I-mf on the Transactivation Activities of NLSMyf5 and NLSMyogenin

| | Relative CAT Activity (%) | | | |
|---|---|---|---|---|
| | Myf5 | Myogenin | NLSMyf5 | NLSMyogenin |
| Vector | 100 | 100 | 100 | 100 |
| I-mfa | 0.1 | 0.6 | 3.7 | 7.5 |

To determine if the I-mfa interacting region of myogenic regulatory factors overlaps with the DNA binding and dimerization domains of these proteins, gel shift assays with an E box containing probe (B1/B2) were performed. In vitro translated Myogenin prepared as described previously was incubated with either no protein, increasing molar ratios (by a factor of 2) of purified MBP-I-mfaΔN proteins (from a 1:5 fold to a 48 fold molar excess), or a 48-fold molar excess of MBP-I-mfbΔN or MBP-I-mfc for 10 minutes at 37° C. In vitro translated E47N (Sun et al., Cell 66: 423, 1991) was also incubated with either no protein or with a 192 fold molar excess of either MBP-I-mfaΔN, MBP-I-mfbΔN, or MBP-I-mfc for 10 minutes at 37° C. The samples were then incubated for 10 minutes with cocktails containing buffer, dIdC and $^{32}$P-labeled B1/B2 probe (Davis et al., ibid., 1990), containing E box sequences from the MCK promoter. The samples were electrophoresed in 0.5× TBE and subjected to autoradiography.

The analysis showed that homodimers of in vitro translated Myogenin bound the B1/B2 probe and formed a low mobility complex. The MBP-I-mfaΔN fusion protein containing the unique I-mfa domain from amino acid 163 to 246 of SEQ ID NO:2, competed with this complex formation in a dose-dependent manner. Fifty percent interference was observed when MBP-I-mfaΔN was present in 3 to 5 fold molar excess. The MBP fusion proteins containing either the unique carboxyl domain of I-mfb (amino acid 164 to 251 of SEQ ID NO:4) or full length I-mfc showed no effect on Myogenin DNA binding, even when present in 48-fold molar excess. In addition, the DNA binding activity of E47 was not affected by I-mfaΔN even when present in a 192 fold molar excess, indicating that I-mfa interferes specifically with DNA binding of myogenic factors.

In vitro translated Myogenin, MyoD, Myf5 and NLSMyf5 were each incubated with in vitro translated E12 either with no MBP fusion protein or with an increasing molar excess (by a factor of 2) of MBP-I-mfaΔN (from a 48 to 192 fold molar excess relative to Myogenin or from a 160 to 640 fold molar excess relative to MyoD, Myf5, and NLSMyf5). Gel electrophoresis was conducted essentially as described above.

Autoradiography demonstrated that MBP-I-mfaDN also interfered with the DNA binding activities of E12/Myogenin, E12/MyoD, E12/Myf5 and E12/NLSMyf5 heterodimers. However, up to 60–120 fold molar excess of MBP-I-mfaDN was required for 50% inhibition of the DNA binding activity of these heterodimers. These results indicated that I-mfa anti-myogenic activities include inhibition of the activities of myogenic factors by interfering with their binding to DNA target sites.

EXAMPLE 10

Construction of Knock out I-mf Mice

Knock-out mice in which parts of the murine I-mf coding sequence was replaced with the neomycin resistance gene (neo) were generated to assess the consequences of eliminating the murine I-mf protein during mouse development. Genomic I-mf sequences used for these knock-out mice were obtained from the 129/Sv mice so the homologous recombination could take place in a congenic background in 129/Sv mouse embryonic stem cells. I-mf genomic clones were isolated from a genomic library prepared from 129/Sv mice (Zhuang et al., Cell 79: 875–884, 1994; which is incorporated herein by reference in its entirety) using a random-primed I-mfa cDNA probe. Plasmid pPNT (Tybulewicz et al., Cell 65: 1153–1163, 1991; which is incorporated herein by reference in its entirety) provided the vector backbone for the targeting construct. Plasmid pPNT contains the Herpes simplex virus thymidine kinase gene (hsv-tk, a negative selection marker) under the control of the PGK promoter neomycin resistance gene (neo; a positive selection marker) under the control of the PGK promoter such that the PGK-neo expression cassette is in the opposite orientation relative to the PGK-TK expression cassette. To construct pPNT-ΔI-mfa, a 2.7 kb Pst I-Kpn I 5' I-mf genomic fragment containing 5' intron sequences and a portion of the coding region of exon IV was cloned between the PGK-TK and the PGK-Neo cassettes and a 3.2 kb Mlu I-Kpn I 3' I-mf genomic fragment containing a portion of the coding region of exon V and 3' non-coding sequences was inserted downstream of the PGK-neo cassette. The resulting plasmid, pPNT-ΔI-mfa, contained a replacement of a 5 kb region of the I-mf gene with the PGK-neo expression cassette.

The targeting construct was linearized at a unique restriction site in the vector backbone and was transfected by electroporation into mouse embryonic stem (ES) cells. A 129/Sv derived ES cell line, AK-7 described by Zhuang et al. (ibid.) was used for electroporation. These ES cells were routinely cultured on mitomycin C-treated (Sigma) SNL 76/7 cells (feeder cells) as described by McMahon and Bradley (Cell 62: 1073–1085, 1990; which is incorporated herein by reference in its entirety) in culture medium containing high glucose DMEM supplemented with 15% fetal bovine serum (Hyclone Laboratories, Inc., Logan, Utah) and 0.1 μM (micromolar) β-mercaptoethanol. To prepare the targeting construct for transfection, 25 μg (micrograms) of the targeting construct was linearized by digestion with Not I, phenol-chloroform extracted, and ethanol precipitated. The linearized vector was then electroporated into 1–2×10$^7$ AK-7 (ES)cells. The electroporated cells were seeded onto five 10-cm plates. After 24 hours, G418 was added to each of the plates to a final concentration of 200 μg/ml (micrograms per milliliter). After three days gancyclovir was added to four of the plates to a final concentration of 2 μg/ml (micrograms per milliliter). This selection enriches the population of ES cells that have undergone homologous recombination by eliminating ES cell clones that have randomly integrated the targeting construct. In correctly targeted constructs the PGK-TK is not expressed and thus the cells are not susceptible to gancyclovir selection. This counter-selection for gancyclovir-resistant colonies in the presence of G418 allowed 10-fold fewer ES colonies to survive as compared to ES colonies that received only G418 selection. The culture medium for each plate was changed every day for the first few days, and then changed as needed after selection had occurred.

After 10 days of selection, a portion of each colony was picked microscopically with a drawn micropipette, and was directly analyzed by PCR as described by Joyner et al. (Nature 338: 153–156, 1989; which is incorporated herein by reference in its entirety). Briefly, PCR amplification was performed as described (Kogan et al., New England J. Med. 317: 985–990, 1987; which is incorporated herein by reference in its entirety) using 40 cycles of 93° C. for 30 seconds, 57° C. for 30 seconds, and 65° C. for 3 minutes. To detect the wild-type allele, primers NK2 and AC48 (CATCTAGGAATGAAGTAAGCAGGA (SEQ ID NO:20) and GCAAGTTGGTGATOCTGTCTGTCTGTGGATGCG (SEQ ID NO:21), respectively) were used in the PCR reaction. To detect the mutant I-mf allele, primers NK3rev and YZ29 (AATCAATGTGCCTCCTAGATCTCTAGCC (SEQ ID NO:22) and TCGCAGCGCATCGCCTTCCTA (SEQ ID NO:23), respectively) were used in the PCR reaction. Positive colonies, identified by PCR, were subcloned into 4-well plates, expanded into 60 mm plates and frozen into 2–3 ampules. Among the clones that were selected for both G418-resistance (positive selection for neo gene expression) and gancyclovir-resistance (negative selection) 10% of the population contained correctly targeted integration of the vector into the murine I-mf locus.

To generate chimeric mice, each positive clone was thawed and passaged once on feeder cells. The transfected cells were trypsinized into single cells, and blastocysts obtained from C57BL/6J mice were injected with approximately 15 cells. The injected blastocysts were then implanted into pseudopregnant mice (C57BL/6J×CBA). Five male and 6 female chimeras arose from the injected blastocysts. One male chimera and one female chimera gave germ-line transmission at a high rate as determined by the frequency of agouti coat color transmission to their offspring (F1) in a cross with C57BL/6J female mice. Since 50% of the agouti coat color offspring (F1) should represent heterozygous mutants, their genotypes were determined by Southern blot analysis. Briefly, genomic DNA prepared from tail biopsies was digested with Hind III and Xba I and probed with probe specific to exon III of I-mf. This probe detects a 17 kb fragment from the wild-type allele and a 7 kb fragment from the mutant allele. Therefore, a Southern analysis would show a single 13 kb band for a wild-type mouse, 13 kb and 7 kb fragments for a heterozygous mouse, and a single 7 kb band for a homozygous mutant mouse. The resulting offspring (F1), heterozygous (±) mice, were mated with sibling heterozygous mice to give rise to the homozygous (−/−) mutant mice. Heterologous (±) mice were kept on a hybrid C57BL/6J×129 background, were back-crossed once to give inbred 129 mice or were back-crossed multiple times into a C57BL/6J background. The majority of homozygous mutant mice in the C57BL/6J background die during embryogenesis.

Those with ordinary skill in the art will appreciate that other embodiments and variations of the invention are possible which employ the same inventive concepts described above. Therefore, the invention is not to be limited except by the above description, but is to be determined in scope by the claims which follow.

We claim:

1. A purified and isolated polynucleotide selected from the group consisting of (A) a polynucleotide of SEQ ID NO:1 from nucleotide 31 to nucleotide 768 encoding I-mfa; (B) a polynucleotide of SEQ ID NO:3 from nucleotide 29 to nucleotide 781 encoding I-mfb; (C) a polynucleotide of SEQ ID NO:5 from nucleotide 211 to nucleotide 699 encoding I-mfc; (D) a polynucleotide that hybridizes under moderate to high stringency conditions to the polynucleotide of (A); (E) a polynucleotide that hybridizes under moderate to high stringency conditions to the polynucleotide of (B); and (F) a polynucleotide that hybridizes under moderate to high stringency conditions to the polynucleotide of (C), wherein said polynucleotide (D), (E) and (F), or a complement thereof, encodes a functional I-mf protein.

2. A polynucleotide expression construct for transforming a host cell to express an I-mf protein, comprising:

a polynucleotide expression vector;

a purified and isolated polynucleotide selected from the group consisting of (A) a polynucleotide of SEQ ID NO:1 from nucleotide 31 to nucleotide 768 encoding I-mfa; (B) a polynucleotide of SEQ ID NO:3 from nucleotide 29 to nucleotide 781 encoding I-mfb; (C) a polynucleotide of SEQ ID NO:5 from nucleotide 211 to nucleotide 699 encoding I-mfc; (D) a polynucleotide that hybridizes under moderate to high stringency conditions to the polynucleotide of (A); (E) a polynucleotide that hybridizes under moderate to high stringency conditions to the polynucleotide of (B); and (F) a polynucleotide that hybridizes under moderate to high stringency conditions to the polynucleotide of (C), wherein said polynucleotide (D), (E) and (F), or a complement thereof, encodes a functional I-mf protein, and said I-mf encoding polynucleotide operably coupled to said expression vector to form an expression construct operable to direct expression of said I-mf protein by said host cell following introduction of said expression construct into said host cell.

3. A polynucleotide expression construct according to claim 2, wherein said expression vector is selected from the group consisting of (A) a DNA plasmid, (B) a DNA viral expression vector, and (C) an RNA viral expression vector.

4. A method for expressing an I-mf protein in a host cell, comprising the steps of:

introducing into said host cell a polynucleotide expression construct incorporating a DNA polynucleotide selected from the group consisting of (A) a polynucleotide of SEQ ID NO:1 from nucleotide 31 to nucleotide 768 encoding I-mfa; (B) a polynucleotide of SEQ ID NO:3 from nucleotide 29 to nucleotide 781 encoding I-mfb; (C) a polynucleotide of SEQ ID NO:5 from nucleotide 211 to nucleotide 699 encoding I-mfc; (D) a polynucleotide that hybridizes under moderate to high stringency conditions to the polynucleotide of (A); (E) a polynucleotide that hybridizes under moderate to high stringency conditions to the polynucleotide of (B); and (F) a polynucleotide that hybridizes under moderate to high stringency conditions to the polynucleotide of (C), wherein said polynucleotide (D), (E) and (F), or a complement thereof, encodes a functional I-mf protein, and wherein said expression construct is operable to transform said host cell to direct expression of said DNA polynucleotide by said host cell; and incubating said host cell transformed by introduction of said expression construct in an appropriate incubation medium under appropriate growth conditions to promote growth and permit expression by said host cells of said I-mf protein.

5. A method according to claim 4, further comprising the step of isolating said I-mf protein or I-mf analog expressed by said host cell.

6. A method according to claim 4, wherein said expression construct incorporates a polynucleotide expression vector selected from the group consisting of (A) a DNA plasmid, (B) a DNA viral expression vector, and (C) an RNA viral expression vector.

7. A host cell transfected with a polynucleotide expression construct incorporating a DNA polynucleotide selected from the group consisting of (A) a polynucleotide of SEQ ID NO:1 from nucleotide 31 to nucleotide 768 encoding I-mfa; (B) a polynucleotide of SEQ ID NO:3 from nucleotide 29 to nucleotide 781 encoding I-mfb; (C) a polynucleotide of SEQ ID NO:5 from nucleotide 211 to nucleotide 699 encoding I-mfc; (D) a polynucleotide that hybridizes under moderate to high stringency conditions to the polynucleotide of (A); (E) a polynucleotide that hybridizes under moderate to high stringency conditions to the polynucleotide of (B); and (F) a polynucleotide that hybridizes under moderate to high stringency conditions to the polynucleotide of (C), wherein said polynucleotide (D), (E) and (F), or a complement thereof, encodes a functional I-mf protein, and wherein said expression construct is operable to transform said host cell to direct expression of said DNA polynucleotide by said host cell.

8. A host cell according to claim 7, wherein said host cell is a yeast cell.

9. A host cell according to claim 7, wherein said host cell is a mammalian cell.

\* \* \* \* \*